(12) United States Patent
Tao et al.

(10) Patent No.: US 11,207,340 B2
(45) Date of Patent: Dec. 28, 2021

(54) TUMOR SUPPRESSOR TET1 AND USES THEREOF

(71) Applicant: The Chinese University of Hong Kong, Hong Kong (CN)

(72) Inventors: Qian Tao, Hong Kong (CN); Lili Li, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 15/988,619

(22) Filed: May 24, 2018

(65) Prior Publication Data

US 2019/0167708 A1   Jun. 6, 2019

Related U.S. Application Data

(60) Provisional application No. 62/511,630, filed on May 26, 2017.

(51) Int. Cl.
| | | |
|---|---|---|
| *A61K 31/711* | (2006.01) | |
| *A61K 31/713* | (2006.01) | |
| *A61K 48/00* | (2006.01) | |
| *C12Q 1/6827* | (2018.01) | |
| *C12Q 1/6886* | (2018.01) | |

(52) U.S. Cl.
CPC .......... *A61K 31/711* (2013.01); *A61K 31/713* (2013.01); *A61K 48/0016* (2013.01); *A61K 48/0058* (2013.01); *A61K 48/0066* (2013.01); *C12Q 1/6827* (2013.01); *C12Q 1/6886* (2013.01); *C12Q 2600/154* (2013.01)

(58) Field of Classification Search
None
See application file for complete search history.

(56) References Cited

U.S. PATENT DOCUMENTS 10,679,730 B2 * 6/2020 Rosner ................. A61K 31/706

OTHER PUBLICATIONS

Zhao, et al. (2015) "Tubulin structure-based drug design for the development of novel 4B-sulfur substituted podophyllum tubulin inhibitors with anti-tumor activity", Nature, Scientific Reports, 5: Article 10172 (11 pages). (Year: 2015).*
Cimmino, et al. (2015) "TET1 is a tumor suppressor of hematopoietic malignancy", Nature Immunology, 16(6): 653-66. (Year: 2015).*
Bachman, et al. "5-Hydroxymethylcytosine is a predominantly stable DNA modification." Nature chemistry 6, No. 12 (2014): 1049.
Baylin, et al. "Epigenetic gene silencing in cancer—a mechanism for early oncogenic pathway addiction?." Nature Reviews Cancer 6, No. 2 (2006): 107.
Ciccarone, et al. "Poly (ADP-ribosyl) ation is involved in the epigenetic control of TET1 gene transcription." Oncotarget 5, No. 21 (2014): 10356.
Cimmino, et al. "TET1 is a tumor suppressor of hematopoietic malignancy." Nature immunology 16, No. 6 (2015): 653.
Dawlaty, et al. "Tet1 is dispensable for maintaining pluripotency and its loss is compatible with embryonic and postnatal development." Cell stem cell 9, No. 2 (2011): 166-175.
Delhommeau, et al. "Mutation in TET2 in myeloid cancers." New England Journal of Medicine 360, No. 22 (2009): 2289-2301.
Fan, et al. "Restored expression levels of TET1 decrease the proliferation and migration of renal carcinoma cells." Molecular medicine reports 12, No. 4 (2015) 4837-4842.
Gambichler, et al. "Decreased expression of ten-eleven translocation 2 protein is associated with progressive disease and death in patients with mycosis fungoides." British Journal of Dermatology 174, No. 3 (2016): 652-653.
Ghoshal, et al. "Inhibitors of histone deacetylase and DNA methyltransferase synergistically activate the methylated metallothionein I promoter by activating the transcription factor MTF-1 and forming an open chromatin structure." Molecular and cellular biology 22, No. 23 (2002): 8302-8319.
Guo, et al. "Hydroxylation of 5-methylcytosine by TET1 promotes active DNA demethylation in the adult brain." Cell 145, No. 3 (2011): 423-434.
Haffner, et al. "Global 5-hydroxymethylcytosine content is significantly reduced in tissue stem/progenitor cell compartments and in human cancers." Oncotarget 2, No. 8 (2011): 627.
Hamidi, et al. "Genetic alterations of DNA methylation machinery in human diseases." Epigenomics 7, No. 2 (2015): 247-265.
Hsu, et al. "TET1 suppresses cancer invasion by activating the tissue inhibitors of metalloproteinases." Cell reports 2, No. 3 (2012): 568-579.
Huang, et al. "Connections between TET proteins and aberrant DNA modification in cancer." Trends in Genetics 30, No. 10 (2014): 464-474.
Huang, et al. "Loss of nuclear localization of TET2 in colorectal cancer." Clinical epigenetics 8, No. 1 (2016): 9.
Ichimura, et al. "Aberrant TET1 methylation closely associated with CpG island methylator phenotype in colorectal cancer." Cancer Prevention Research (2015) canprevres-0306.
Ito, et al. "Role of Tet proteins in 5mC to 5hmC conversion, ES-cell self-renewal and inner cell mass specification." nature 466, No. 7310 (2010): 1129.
Jin, et al. "Epigenetic silencing of a Ca2+-regulated Ras GTPase-activating protein RASAL defines a new mechanism of Ras activation in human cancers." Proceedings of the National Academy of Sciences 104, No. 30 (2007): 12353-12358.
Jin, et al. "5-Hydroxymethylcytosine is strongly depleted in human cancers but its levels do not correlate with IDH1 mutations." Cancer research (2011): canres-2023.
Jones, et al. "The epigenomics of cancer." Cell 128, No. 4 (2007): 683-692.

(Continued)

*Primary Examiner* — Robert M Kelly
(74) *Attorney, Agent, or Firm* — Kilpatrick Townsend & Stockton LLP

(57) ABSTRACT

The present invention provides a method for assessing the risk of cancer in a subject by detecting elevated methylation level in the genomic sequence of the TET1 gene, which leads to suppressed expression of this gene. A kit and device useful for practicing such a method are also provided.

9 Claims, 11 Drawing Sheets
(10 of 11 Drawing Sheet(s) Filed in Color)
Specification includes a Sequence Listing.

(56) References Cited

OTHER PUBLICATIONS

Konstandin, et al. "Genomic 5-hydroxymethylcytosine levels correlate with TET2 mutations and a distinct global gene expression pattern in secondary acute myeloid leukemia." Leukemia 25, No. 10 (2011): 1649.
Kudo, et al. "Loss of 5-hydroxymethylcytosine is accompanied with malignant cellular transformation." Cancer science 103, No. 4 (2012): 670-676.
Li, et al. "Epigenetic changes in virus-associated human cancers." Cell research 15, No. 4 (2005): 262.
Li, et al. "Characterization of the nasopharyngeal carcinoma methylome identifies aberrant disruption of key signaling pathways and methylated tumor suppressor genes." Epigenomics 0 (2015): 155-173.
Li, et al. "Epigenetic identification of receptor tyrosine kinase-like orphan receptor 2 as a functional tumor suppressor inhibiting β-catenin and AKT signaling but frequently methylated in common carcinomas." Cellular and molecular life sciences 71, No. 11 (2014): 2179-2192.
Li, et al. "The human cadherin 11 is a pro-apoptotic tumor suppressor modulating cell stemness through Wnt/β-catenin signaling and silenced in common carcinomas." Oncogene 31, No. 34 (2012): 3901.
Lian, et al. "Loss of 5-hydroxymethylcytosine is an epigenetic hallmark of melanoma." Cell 150, No. 6 (2012): 1135-1146.
Moran-Crusio, et al. "Tet2 loss leads to increased hematopoietic stem cell self-renewal and myeloid transformation." Cancer cell 20, No. 1 (2011): 11-24.
Müller, et al. "Nuclear exclusion of TET1 is associated with loss of 5-hydroxymethylcytosine in IDH1 wild-type gliomas." The American journal of pathology 181, No. 2 (2012): 675-683.
Murray, et al. "Epigenetic silencing of a proapoptotic cell adhesion molecule, the immunoglobulin superfamily member IGSF4, by promoter CpG methylation protects Hodgkin lymphoma cells from apoptosis." The American journal of pathology 177, No. 3 (2010): 1480-1490.
Neri, et al. "Genome-wide analysis identifies a functional association of Tet1 and Polycomb repressive complex 2 in mouse embryonic stem cells." Genome biology 14, No. 8 (2013): R91.
Neri, et al. "TET1 is a tumour suppressor that inhibits colon cancer growth by derepressing inhibitors of the WNT pathway." Oncogene 34, No. 32 (2015): 4168.
Neri, et al. "TET1 is controlled by pluripotency-associated factors in ESCs and downmodulated by PRC2 in differentiated cells and tissues." Nucleic acids research 43, No. 14 (2015): 6814-6826.
Okashita, et al. "PRDM14 promotes active DNA demethylation through the ten-eleven translocation (TET)-mediated base excision repair pathway in embryonic stem cells." Development (2012): dev-099622.
Park, et al. "Decrease of 5hmC in gastric cancers is associated with TET1 silencing due to with DNA methylation and bivalent histone marks at TET1 CpG island 3'-shore." Oncotarget 6, No. 35 (2015): 37647.
Rawłuszko-Wieczorek, et al. "Clinical significance of DNA methylation mRNA Tevels of TET family members in colorectal cancer." Journal of cancer research and clinical oncology 141, No. 8 (2015): 1379-1392.
Schübeler, "Function and information content of DNA methylation." Nature 517, No. 7534 (2015): 321.
Song, et al. "MicroRNA-antagonism regulates breast cancer stemness and metastasis via TET-family-dependent chromatin remodeling." Cell 154, No. 2 (2013): 311-324.
Spruijt, et al. "Dynamic readers for 5-(hydroxy) methylcytosine and its oxidized derivatives." Cell 152, No. 5 (2013): 1146-1159.
Sun et al. "HMGA2/TET1/HOXA9 signaling pathway regulates breast cancer growth and metastasis." Proceedings of the National Academy of Sciences 110, No. 24 (2013): 9920-9925.
Tahiliani, et al. "Conversion of 5-methylcytosine to 5-hydroxymethylcytosine in mammalian DNA by MLL partner TET1." Science 324, No. 5929 (2009): 930-935.
Tan, et al. "Tet family proteins and 5-hydroxymethylcytosine in development and disease." Development 139, No. 11 (2012): 1895-1902.
Tao, "Cancer research in an era when epigenetics is no longer "epi"—challenges and opportunities." Chinese journal of cancer 32, No. 1 (2013): 1.
Tao, et al. "Defective de novo methylation of viral and cellular DNA sequences in ICF syndrome cells." Human molecular genetics 11, No. 18 (2002): 2091-2102.
Tao, et al. "Methylation status of the Epstein-Barr virus major latent promoter C in iatrogenic B cell lymphoproliferative disease: application of PCR-based analysis." The American journal of pathology 155, No. 2 (1999): 619-625.
Tsai, et al. "The Epstein-Barr virus oncogene product, latent membrane protein 1, induces the downregulation of E-cadherin gene expression via activation of DNA methyltransferases." Proceedings of the National Academy of Sciences 99, No. 15 (2002): 10084-10089.
Tsai, et al. "Reduction of global 5-hydroxymethylcytosine is a poor prognostic factor in breast cancer patients, especially for an ER/PR-negative subtype." Breast cancer research and treatment 153, No. 1 (2015): 219-234.
Vogelstein, et al. "Cancer genome landscapes." science 339, No. 6127 (2013) 1546-1558.
Wang, et al. "Regulation of TET protein stability by calpains." Cell reports 6, No. 2 (2014): 278-284.
Wang, et al. "Epigenetic silencing of the 3p22 tumor suppressor DLEC1 by promoter CpG methylation in non-Hodgkin and Hodgkin lymphomas." Journal of translational medicine 10, No. 1 (2012): 209.
Williams, et al. "TET1 and hydroxymethylcytosine in transcription and DNA methylation fidelity." Nature 473, No. 7347 (2011): 343.
Wu, et al. "Suppression of TET1-dependent DNA demethylation is essential for KRAS-mediated transformation." Cell reports 9, No. 5 (2014): 1827-1840.
Wu, et al. "Dual functions of Tet1 in transcriptional regulation in mouse embryonic stem cells." Nature 473, No. 7347 (2011): 389.
Yamaguchi, et al. "Role of Tet1 in erasure of genomic imprinting." Nature 504, No. 7480 (2013): 460.
Yang, et al. "Tumor development is associated with decrease of TET gene expression and 5-methylcytosine hydroxylation." Oncogene 32, No. 5 (2013): 663.
Yildirim, et al. "Mbd3/NURD complex regulates expression of 5-hydroxymethylcytosine marked genes in embryonic stem cells." cell 147, No. 7 (2011): 1498-1510.
Ying, et al. "Functional epigenetics identifies a protocadherin PCDH10 as a candidate tumor suppressor for nasopharyngeal, esophageal and multiple other carcinomas with frequent methylation." Oncogene 25, No. 7 (2006): 1070.
You, et al. "Cancer genetics and epigenetics: two sides of the same coin?" Cancer cell 22, 9-20, doi:10.1016/j.ccr.2012.06.008 (2012).

* cited by examiner

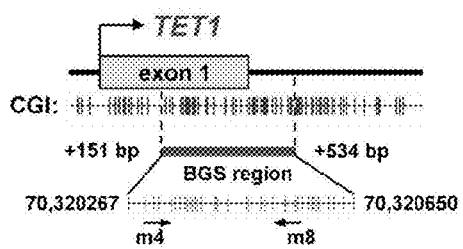
FIGURE 2A
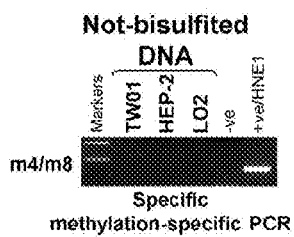
FIGURE 2B
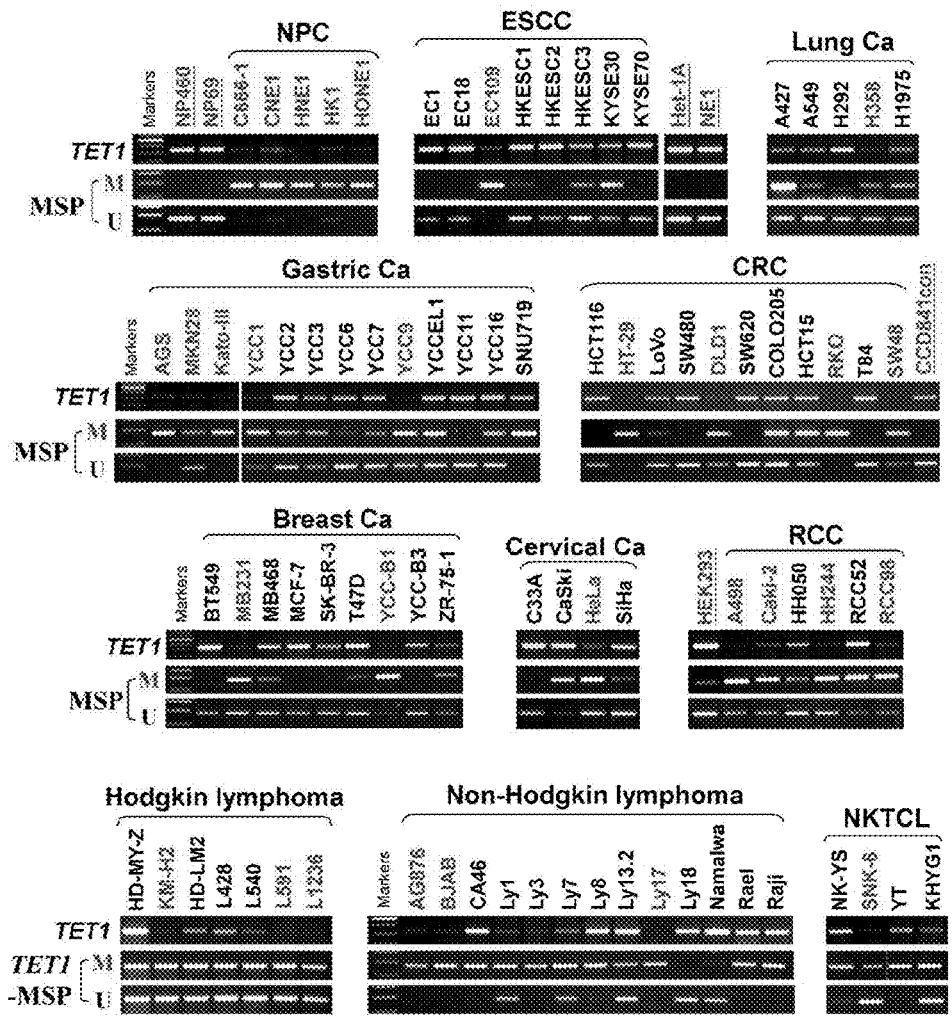
FIGURE 2C
FIGURE 2D
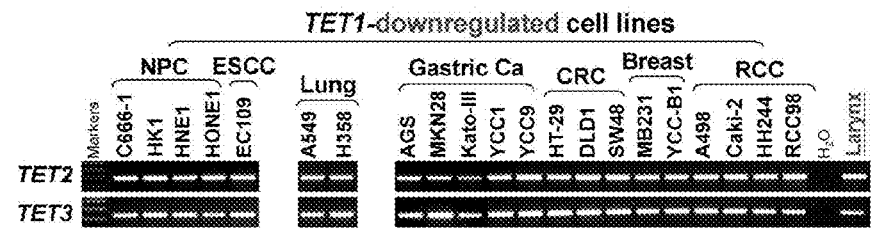
FIGURE 2E FIGURE 4A
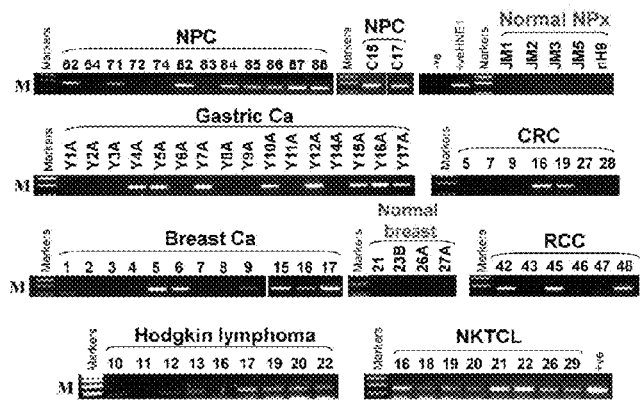
FIGURE 4B
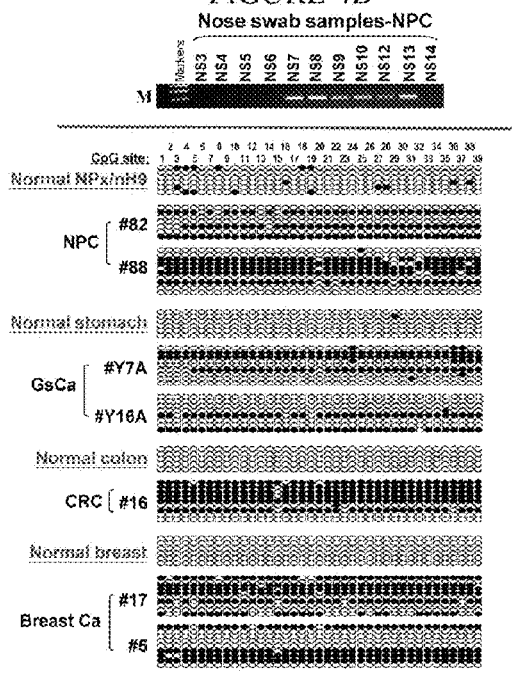
FIGURE 4C
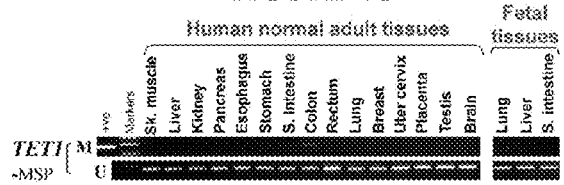
FIGURE 4D
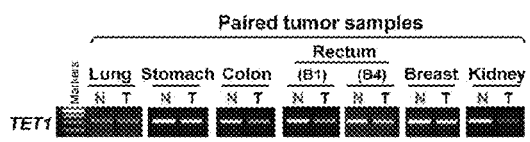
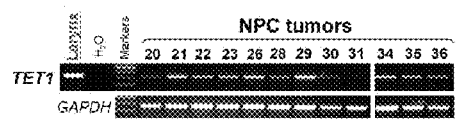
FIGURE 4E FIGURE 5A
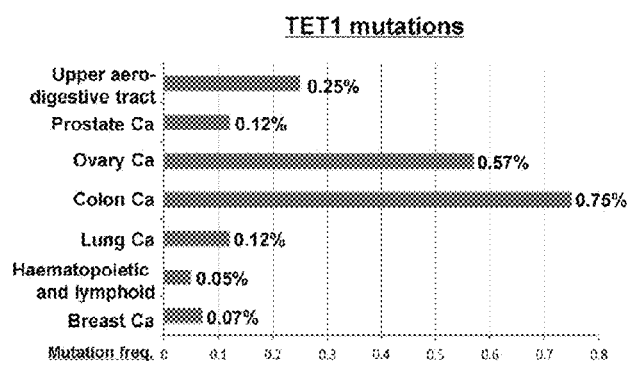
FIGURE 5B
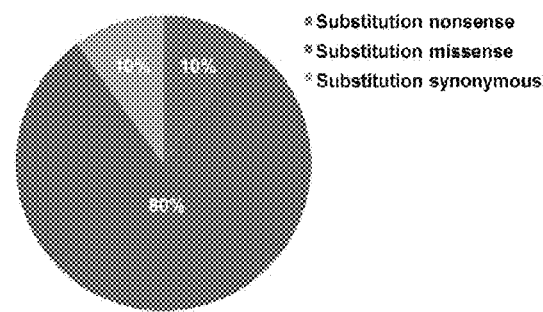
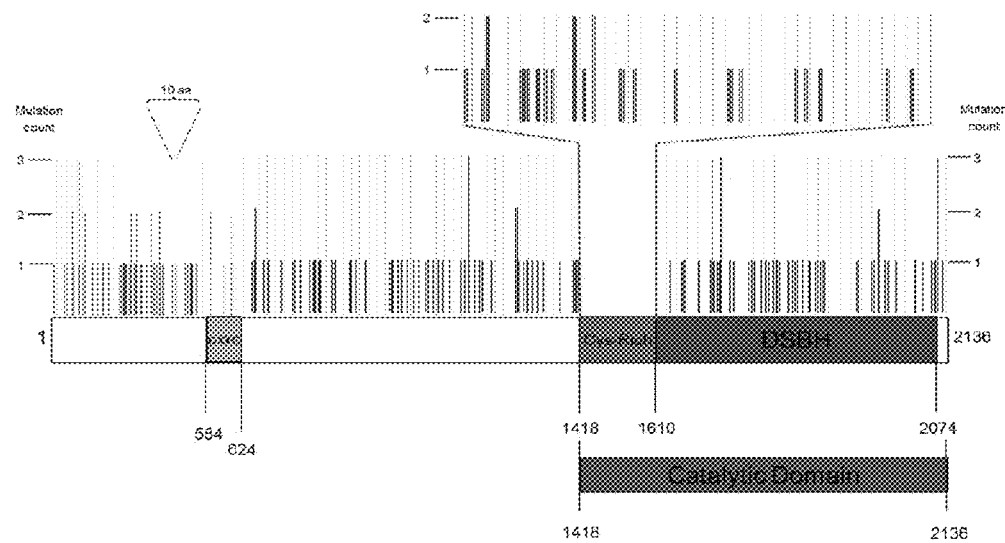
FIGURE 5C FIGURE 8A
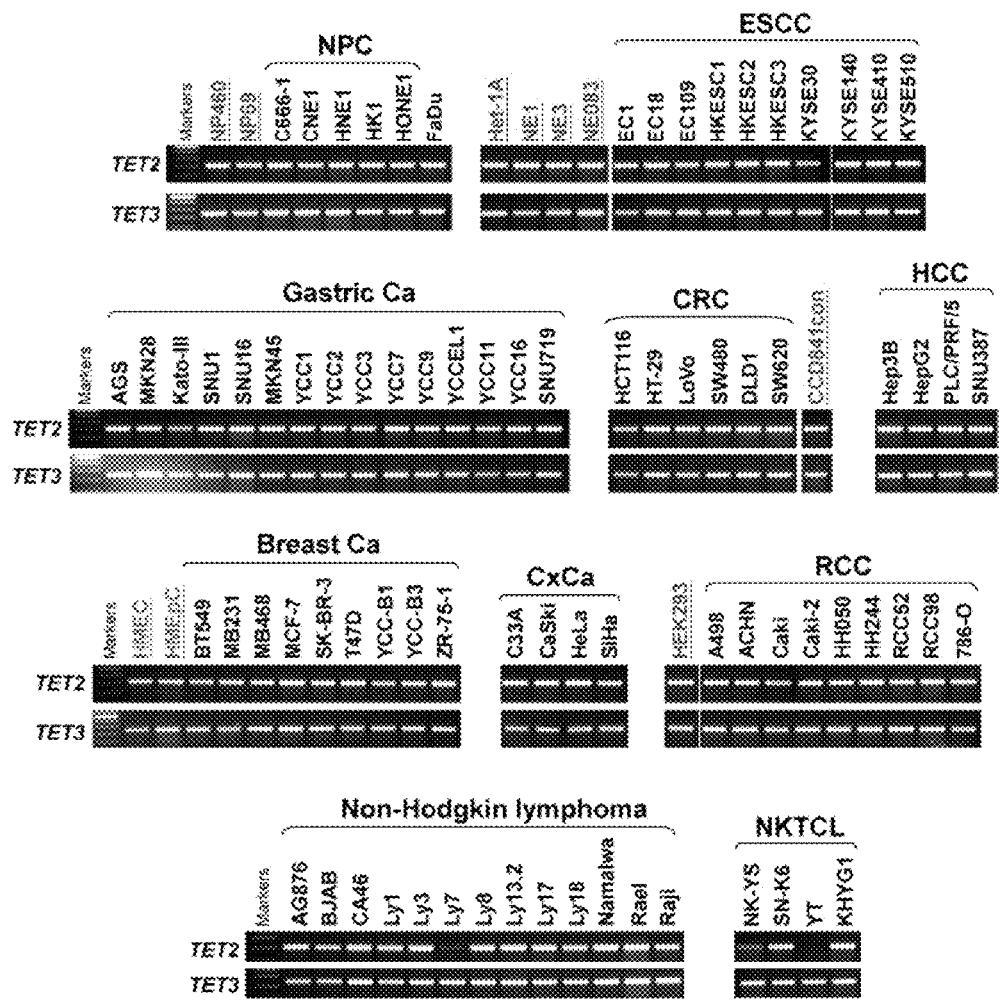
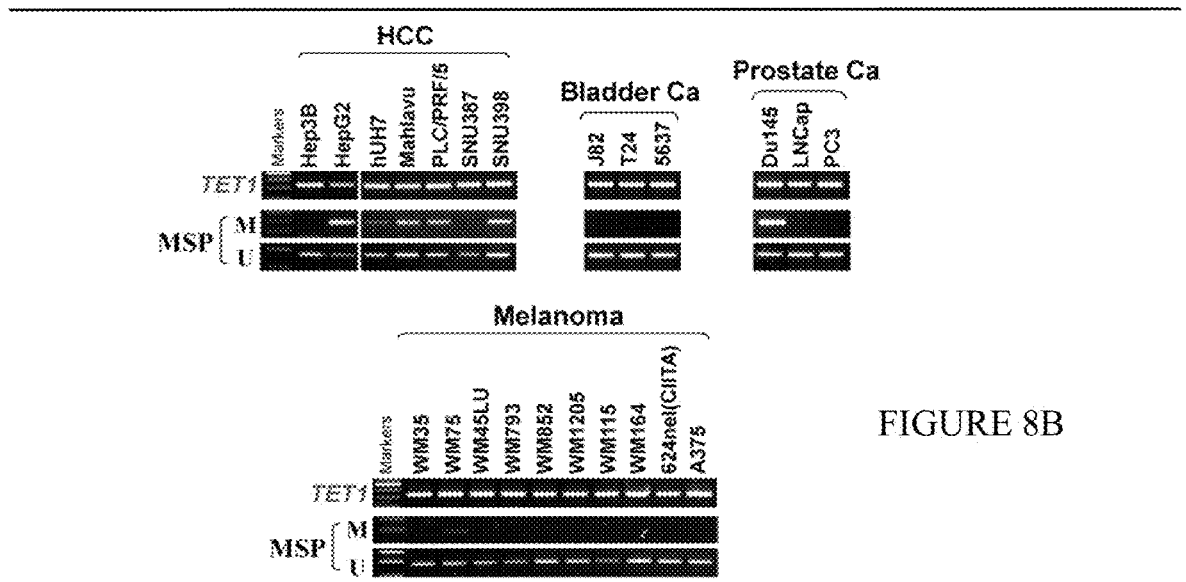
FIGURE 8B

TET1 DNA copy number changes

SEQUENCE LISTING

<160> NUMBER OF SEQ ID NOS: 51

<210> SEQ ID NO 1
<211> LENGTH: 384
<212> TYPE: DNA
<213> ORGANISM: Homo sapiens

<400> SEQUENCE: 1

```
tgcctctcca ctgtggacct ttgggaaccg actcctcacc tcggggctc gggccttgac      60 tgtgctggga gccggtaggc gtcctccgcg acccgcccgc gcccctcgcg cccgccgggg     120
ccccgggctc caaagttgtg gggaccggcg cgagttggaa agtttgcccg agggctggtg    180
caggcttgga gctgggggcc gtgcgctgcc ctgggaatgt gacccggcca gcggtgagtt    240
ggggccgggg cagagggcag gggtgcgggg agcgaggact ccgacgccga ggcccgaggg    300
gggtccggga ggcggcgctc ggcgcgggct ggatgtggcc ggggctctgc gtccttggct    360
ctcccgctgc ctcaggggtg ggct                                           384
```

<210> SEQ ID NO 2
<211> LENGTH: 173
<212> TYPE: DNA
<213> ORGANISM: Homo sapiens

<400> SEQUENCE: 2

```
gccggtaggc gtcctccgcg acccgcccgc gcccctcgcg cccgccgggg ccccgggctc      60
caaagttgtg gggaccggcg cgagttggaa agtttgcccg agggctggtg caggcttgga     120
gctgggggcc gtgcgctgcc ctgggaatgt gacccggcca gcggtgagtt ggg           173
```

<210> SEQ ID NO 3
<211> LENGTH: 9601
<212> TYPE: DNA
<213> ORGANISM: Homo sapiens

<400> SEQUENCE: 3

```
agacactgct gctccggggg gctgacctgg cggggagtgg ccgcgcagtc tgctccggcg      60
ccgctttgtg cgcgcagccg ctggcccctc tactcccggg tctgcccccc gggacacccc     120
tctgcctcgc ccaagtcatg cagccctacc tgcctctcca ctgtggacct ttgggaaccg    180
actcctcacc tcggggctc gggccttgac tgtgctggga gccggtaggc gtcctccgcg    240
acccgcccgc gcccctcgcg cccgccgggg ccccgggctc caaagttgtg gggaccggcg    300
cgagttggaa agtttgcccg agggctggtg caggcttgga gctgggggcc gtgcgctgcc    360
ctgggaatgt gacccggcca gcgaccaaaa ccttgtgtga ctgagctgaa gagcagtgca    420
tccagattct cctcagaagt gagactttcc aaaggaccaa tgactctgtt tcctgcgccc    480
```

```
tttcatttt  tcctactctg  tagctatgtc  tcgatcccgc  catgcaaggc  cttccagatt    540
agtcaggaag  gaagatgtaa  acaaaaaaaa  gaaaaacagc  caactacgaa  agacaaccaa    600
gggagccaac  aaaaatgtgg  catcagtcaa  gactttaagc  cctggaaaat  taaagcaatt    660
aattcaagaa  agagatgtta  agaaaaaaac  agaacctaaa  ccacccgtgc  cagtcagaag    720
ccttctgaca  agagctggag  cagcacgcat  gaatttggat  aggactgagg  ttcttttttca    780
gaacccagag  tccttaacct  gcaatgggtt  tacaatggcg  ctacgaagca  cctctcttag    840
caggcgactc  tcccaacccc  cactggtcgt  agccaaatcc  aaaaaggttc  cactttctaa    900
gggtttagaa  aagcaacatg  attgtgatta  taagatactc  cctgctttgg  gagtaaagca    960
ctcagaaaat  gattcggttc  caatgcaaga  cacccaagtc  cttcctgata  tagagactct   1020
aattggtgta  caaaatccct  ctttacttaa  aggtaagagc  caagagacaa  ctcagttttg   1080
gtcccaaaga  gttgaggatt  ccaagatcaa  tatccctacc  cacagtggcc  ctgcagctga   1140
gatccttcct  gggccactgg  aagggacacg  ctgtggtgaa  ggactattct  ctgaagagac   1200
attgaatgat  accagtggtt  ccccaaaaat  gtttgctcag  gacacagtgt  gtgctccttt   1260
tccccaaaga  gcaaccccca  aagttacctc  tcaaggaaac  cccagcattc  agttagaaga   1320
gttgggttca  cgagtagaat  ctcttaagtt  atctgattct  tacctggatc  ccattaaaag   1380
tgaacatgat  tgctaccca   cctccagtct  taataaggtt  atacctgact  gaaccttag    1440
aaactgcttg  gctcttggtg  ggtctacgtc  tcctacctct  gtaataaaat  tcctcttggc   1500
aggctcaaaa  caagcgaccc  ttggtgctaa  accagatcat  caagaggcct  tcgaagctac   1560
tgcaaatcaa  caggaagttt  ctgataccac  ctctttccta  ggacaggcct  ttggtgctat   1620
cccacatcaa  tgggaacttc  ctggtgctga  cccagttcat  ggtgaggccc  tgggtgagac   1680
cccagatcta  ccagagattc  ctggtgctat  tccagtccaa  ggagaggtct  ttggtactat   1740
tttagaccaa  caagaaactc  ttggtatgag  tgggagtgtt  gtcccagact  tgcctgtctt   1800
ccttcctgtt  cctccaaatc  caattgctac  ctttaatgct  ccttccaaat  ggcctgagcc   1860
ccaaagcact  gtctcatatg  gacttgcagt  ccagggtgct  atacagattt  tgcctttggg   1920
ctcaggacac  actcctcaat  catcatcaaa  ctcagagaaa  aattcattac  ctccagtaat   1980
ggctataagc  aatgtagaaa  atgagaagca  ggttcatata  agcttcctgc  cagctaacac   2040
tcaggggttc  ccattagccc  ctgagagagg  actcttccat  gcttcactgg  gtatagccca   2100
actctctcag  gctggtccta  gcaaatcaga  cagagggagc  tcccaggtca  gtgtaaccag   2160
cacagttcat  gttgtcaaca  ccacagtggt  gactatgcca  gtgccaatgg  tcagtacctc   2220
ctcttcttcc  tataccactt  tgctaccgac  tttggaaaag  aagaaagaa   agcgatgtgg   2280
ggtctgtgaa  ccctgccagc  agaagaccaa  ctgtggtgaa  tgcacttact  gcaagaacag   2340
aaagaacagc  catcagatct  gtaagaaaag  aaaatgtgag  gagctgaaaa  agaaaccatc   2400
tgttgttgtg  cctctggagg  ttataaagga  aacaagagg   ccccagaggg  aaagaagcc    2460
caaagtttta  aaggcagatt  ttgacaacaa  accagtaaat  ggccccaagt  cagaatccat   2520
ggactacagt  agatgtggtc  atggggaaga  acaaaaattg  gaattgaacc  cacatactgt   2580
tgaaaatgta  actaaaaatg  aagacagcat  gacaggcatc  gaggtggaga  agtggacaca   2640
aaacaagaaa  tcacagttaa  ctgatcacgt  gaaaggagat  tttagtgcta  atgtcccaga   2700
agctgaaaaa  tcgaaaaact  ctgaagttga  caagaaacga  accaaatctc  caaaattgtt   2760
tgtacaaacc  gtaagaaatg  gcattaaaca  tgtcacactgt  ttaccagctg  aaacaaatgt   2820
```

```
ttcatttaaa aaattcaata ttgaagaatt cggcaagaca ttggaaaaca attcttataa    2880
attcctaaaa gacactgcaa accataaaaa cgctatgagc tctgttgcta ctgatatgag    2940
ttgtgatcat ctcaagggga gaagtaacgt tttagtattc cagcagcctg gctttaactg    3000
cagttccatt ccacattctt cacactccat cataaatcat catgctagta tacacaatga    3060
aggtgatcaa ccaaaaactc ctgagaatat accaagtaaa gaaccaaaag atggatctcc    3120
cgttcaacca agtctcttat cgttaatgaa agataggaga ttaacattgg agcaagtggt    3180
agccatagag gccctgactc aactctcaga agccccatca gagaattcct ccccatcaaa    3240
gtcagagaag gatgaggaat cagagcgag aacagccagt ttgcttaata gctgcaaagc    3300
tatcctctac actgtaagaa aagacctcca agacccaaac ttacagggag agccaccaaa    3360
acttaatcac tgtccatctt tggaaaaaca aagttcatgc aacacggtgg ttttcaatgg    3420
gcaaactact acccttccca actcacatat caactcagct actaaccaag catccacaaa    3480
gtcacatgaa tattcaaaag tcacaaattc attatctctt tttataccaa aatcaaattc    3540
atccaagatt gacaccaata aaagtattgc tcaagggata attactcttg acaattgttc    3600
caatgatttg catcagttgc caccaagaaa taatgaagtg gagtattgca accagttact    3660
ggacagcagc aaaaaattgg actcagatga tctatcatgt caggatgcaa cccatacccc a    3720
aattgaggaa gatgttgcaa cacagttgac acaacttgct tcgataatta agatcaatta    3780
tataaaccca gaggacaaaa aagttgaaag tacaccaaca agccttgtca catgtaatgt    3840
acagcaaaaa tacaatcagg agaagggcac aatacaacag aaaccacctt caagtgtaca    3900
caataatcat ggttcatcat taacaaaaca aagaaaccca acccagaaaa agacaaaatc    3960
caccccatca agagatcggc ggaaaaagaa gcccacagtt gtaagttatc aagaaaatga    4020
tcggcagaag tgggaaaagt tgtcctatat gtatggcaca atatgcgaca tttggatagc    4080
atcgaaattt caaaattttg gcaattttg tccacatgat tttcctactg tatttgggaa    4140
aattctcttc tcgaccaaaa tatggaaacc actggctcaa acgaggtcca ttatgcaacc    4200
caaaacagta tttccaccac tcactcagat aaaattacag agatatcctg aatcagcaga    4260
ggaaaaggtg aaggttgaac cattggattc actcagctta tttcatctta aaacggaatc    4320
caacgggaag gcattcactg ataaagctta taattctcag gtacagttaa cggtgaatgc    4380
caatcagaaa gcccatccct tgacccagcc ctcctctcca cctaaccagt gtgctaacgt    4440
gatggcaggc gatgaccaaa tacggtttca gcaggttgtt aaggagcaac tcatgcatca    4500
gagactgcca acattgcctg gtatctctca tgaaacaccc ttaccggagt cagcactaac    4560
tctcaggaat gtaaatgtag tgtgttcagg tggaattaca gtggtttcta ccaaaagtga    4620
agaggaagtc tgttcatcca gttttggaac atcagaattt tccacagtgg acagtgcaca    4680
gaaaaatttt aatgattatg ccatgaactt ctttactaac cctacaaaaa acctagtgtc    4740
tataactaaa gattctgaac tgcccacctg cagctgtctt gatcgagtta tacaaaaaga    4800
caaaggccca tattatacac accttgggc aggaccaagt gttgctgctg tcagggaaat    4860
catggagaat aggtatggtc aaaaaggaaa cgcaataagg atagaaatag tagtgtacac    4920
cggtaaagaa gggaaaagct ctcatggggtg tccaattgct aagtgggttt taagaagaag    4980
cagtgatgaa gaaaaagttc tttgtttggt ccggcagcgt acaggccacc actgtccaac    5040
tgctgtgatg gtggtgctca tcatggtgtg ggatggcatc cctcttccaa tggccgaccg    5100
gctatacaca gagctcacag agaatctaaa gtcatacaat gggcaccccta ccgacagaag    5160
atgcaccctc aatgaaaatc gtacctgtac atgtcaagga attgatccag agacttgtgg    5220
```

```
agcttcattc tcttttggct gttcatggag tatgtacttt aatggctgta agtttggtag    5280
aagcccaagc cccagaagat ttagaattga tccaagctct cccttacatg aaaaaaacct    5340
tgaagataac ttacagagtt tggctacacg attagctcca atttataagc agtatgctcc    5400
agtagcttac caaaatcagg tggaatatga aaatgttgcc cgagaatgtc ggcttggcag    5460
caaggaaggt cgtcccttct ctggggtcac tgcttgcctg gacttctgtg ctcatcccca    5520
cagggacatt cacaacatga ataatggaag cactgtggtt tgtaccttaa ctcgagaaga    5580
taaccgctct ttgggtgtta ttcctcaaga tgagcagctc catgtgctac ctctttataa    5640
gctttcagac acagatgagt ttggctccaa ggaaggaatg gaagccaaga tcaaatctgg    5700
ggccatcgag gtcctggcac cccgccgcaa aaaagaacg tgtttcactc agcctgttcc    5760
ccgttctgga aagaagaggg ctgcgatgat gacagaggtt cttgcacata agataagggc    5820
agtggaaaag aaacctattc cccgaatcaa gcggaagaat aactcaacaa caacaaacaa    5880
cagtaagcct tcgtcactgc aaccttagg gagtaacact gagaccgtgc aacctgaagt    5940
aaaaagtgaa accgaacccc attttatctt aaaaagttca gacaacacta aaacttattc    6000
gctgatgcca tccgctcctc acccagtgaa agaggcatct ccaggcttct cctggtcccc    6060
gaagactgct tcagccacac cagctccact gaagaatgac gcaacagcct catgcgggtt    6120
ttcagaaaga agcagcactc cccactgtac gatgccttcg ggaagactca gtggtgccaa    6180
tgcagctgct gctgatggcc ctggcatttc acagcttggc gaagtggctc ctctccccac    6240
cctgtctgct cctgtgatgg agcccctcat taattctgag ccttccactg gtgtgactga    6300
gccgctaacg cctcatcagc caaaccacca gccctccttc ctcacctctc ctcaagacct    6360
tgcctcttct ccaatggaag aagatgagca gcattctgaa gcagatgagc ctccatcaga    6420
cgaaccccta tctgatgacc ccctgtcacc tgctgaggag aaattgcccc acattgatga    6480
gtattggtca gacagtgagc acatctttttt ggatgcaaat attggtgggg tggccatcgc    6540
acctgctcac ggctcggttt tgattgagtg tgcccggcga gagctgcacg ctaccactcc    6600
tgttgagcac cccaaccgta atcatccaac ccgcctctcc cttgtctttt accagcacaa    6660
aaacctaaat aagccccaac atggttttga actaaacaag attaagtttg aggctaaaga    6720
agctaagaat aagaaaatga aggcctcaga gcaaaaagac caggcagcta atgaaggtcc    6780
agaacagtcc tctgaagtaa atgaattgaa ccaaattcct tctcataaag cattaacatt    6840
aacccatgac aatgttgtca ccgtgtcccc ttatgctctc acacacgttg cggggcccta    6900
taaccattgg gtctgaaggc ttttctcccc ctcttaatgc ctttgctagt gcagtgtatt    6960
ttttcaaggt gctgttaaaa gaaagtcatg ttgtcgttta ctatcttcat ctcacccatt    7020
tcaagtctga ggtaaaaaaa taataatgat aacaaaacgg ggtgggtatt cttaactgtg    7080
actatatttt gacaattggt agaaggtgca cattttaagc aaaaataaaa gttttatagt    7140
tttaaataca taaagaaatg tttcagttag gcattaacct tgatagaatc actcagtttg    7200
gtgctttaaa ttaagtctgt ttactatgaa acaagagtca ttttagagg attttaacag    7260
gttcatgttc tatgatgtaa aatcaagaca cacagtgtta actctacaca gcttctggtg    7320
cttaaccaca tccacacagt taaaataag ctgaattatt atttcatggt gccattgttc    7380
caacatcttc caatcattgc tagaaaattg gcatattcct ttgaaataaa cttatgaaat    7440
gttttctctc ttaaaatatt tctcctgtgt aaaataaatc attgttgtta gtaatggttg    7500
gaggctgttc ataaattgta aatatatatt ttaaaagcac tttctatttt taaaagtaac    7560
```

| | |
|---|---|
| ttgaaataat atagtataag aatcctattg tctattgttt gtgcatattt gcatacaaga | 7620 |
| gaaatcattt atccttgctg tgtagagttc catcttgtta actgcagtat gtattctaat | 7680 |
| catgtatatg gtttgtgttc ttttactgtg tcctctcaca ttcaagtatt agcaacttgc | 7740 |
| agtatataaa atagttagat aatgagaagt tgttaattat ctctaaaatt ggaattagga | 7800 |
| agcatatcac caatactgat taacattctc tttggaacta ggtaagagtg gtctcttctt | 7860 |
| attgaacaac ctcaatttag tttcatccca cctttctcag tataatccat gagaggtgtt | 7920 |
| tccaaaagga gatgagggaa caggataggt ttcagaagag tcaaatgctt ctaatgtctc | 7980 |
| aaggtgataa aatacaaaaa ctaagtagac agatatttgt actgaagtct gatacagaat | 8040 |
| tagaaaaaaa aaattcttgt tgaaatattt tgaaacaaa ttccctacta tcatcacatg | 8100 |
| cctccccaac cccaagtcaa aaacaagagg aatggtacta caaacatggc tttgtccatt | 8160 |
| aagagctaat tcatttgttt atcttagcat actagatttg ggaaaatgat aactcatctt | 8220 |
| ttctgataat tgcctatgtt ctaggtaaca ggaaaacagg cattaagttt attttagtct | 8280 |
| tcccattttc ttcctattac tttattgact catttattg caaaacaaaa aggattaccc | 8340 |
| aaacaacatg tttcgaacaa ggagaatttt caatgaaata cttgattctg ttaaaatgca | 8400 |
| gaggtgctat aacattcaaa gtgtcagatt ccttgggagt atggaaaacc taatggtgct | 8460 |
| tctcccttgg aaatgccata ggaagcccac aaccgctaac acttacaatt ttggtgcaaa | 8520 |
| agcaaacagt tccagcaggc tctctaaaga aaaactcatt gtaacttatt aaaataatat | 8580 |
| ctggtgcaaa gtatctgttt tgagcttttg actaatccaa gtaaaggaat atgaagggat | 8640 |
| tgtaaaaaac aaaatgtcca ttgatagacc atcgtgtaca agtagatttc tgcttgttga | 8700 |
| atatgtaaaa tagggtaatt cattgacttg ttttagtatt ttgtgtgcct tagatttccg | 8760 |
| ttttaagaca tgtatatttt tgtgagccta aggtttctta tatacatata agtatataaa | 8820 |
| taagtgattg tttattgctt cagctgcttc aacaagatat ttactagtat tagactatca | 8880 |
| ggaatacacc cttgcgagat tatgttttag attttaggcc ttagctccca ctagaaatta | 8940 |
| tttcttcacc agatttaatg gataaagttt tatggctctt tatgcatcca ctcatctact | 9000 |
| cattcttcga gtctacactt attgaatgcc tgcaaaatct aagtatcact tttattttc | 9060 |
| tttggatcac cacctatgac atagtaaact tgaagaataa aaactaccct cagaaatatt | 9120 |
| tttaaaagaa gtagcaaatt atcttcagta taatccatgg taatgtatgc agtaattcaa | 9180 |
| attgatctct ctctcaatag gtttcttaac aatctaaact tgaaacatca atgttaattt | 9240 |
| ttggaactat tgggatttgt gacgcttgtt gcagtttacc aaaacaagta tttgaaaata | 9300 |
| tatagtatca actgaaatgt ttccattccg ttgttgtagt taacatcatg aatggacttc | 9360 |
| ttaagctgat tacccactg tgggaaccaa attggattcc tactttgttg gactctcttt | 9420 |
| cctgatttta acaatttacc atcccattct ctgccctgtg atttttttta aaagcttatt | 9480 |
| caatgttctg cagcattgtg attgtatgct ggctacactg cttttagaat gctctttctc | 9540 |
| atgaagcaag gaaataaatt tgtttgaaat gacattttct ctcaaaaaaa aaaaaaaaa | 9600 |
| a | 9601 |

<210> SEQ ID NO 4
<211> LENGTH: 6411
<212> TYPE: DNA
<213> ORGANISM: Homo sapiens

<400> SEQUENCE: 4

| | |
|---|---|
| atgtctcgat cccgccatgc aaggccttcc agattagtca ggaaggaaga tgtaaacaaa | 60 |

```
aaaaagaaaa acagccaact acgaaagaca accaagggag ccaacaaaaa tgtggcatca    120
gtcaagactt taagccctgg aaaattaaag caattaattc aagaaagaga tgttaagaaa    180
aaaacagaac ctaaaccacc cgtgccagtc agaagccttc tgacaagagc tggagcagca    240
cgcatgaatt tggataggac tgaggttctt tttcagaacc cagagtcctt aacctgcaat    300
gggtttacaa tggcgctacg aagcacctct cttagcaggc gactctccca accccccactg    360 gtcgtagcca aatccaaaaa ggttccactt tctaagggtt tagaaaagca acatgattgt    420
gattataaga tactccctgc tttgggagta aagcactcag aaaatgattc ggttccaatg    480
caagacaccc aagtccttcc tgatatagag actctaattg gtgtacaaaa tccctcttta    540
cttaaaggta agagccaaga gacaactcag ttttggtccc aaagagttga ggattccaag    600
atcaatatcc ctacccacag tggccctgca gctgagatcc ttcctgggcc actggaaggg    660
acacgctgtg gtgaaggact attctctgaa gagacattga atgataccag tggttcccca    720
aaaatgtttg ctcaggacac agtgtgtgct ccttttcccc aaagagcaac ccccaaagtt    780
acctctcaag gaaaccccag cattcagtta aagagttgg gttcacgagt agaatctctt    840
aagttatctg attcttacct ggatcccatt aaaagtgaac atgattgcta ccccaccctcc    900 agtcttaata aggttatacc tgacttgaac cttagaaact gcttggctct tggtgggtct    960
acgtctccta cctctgtaat aaaattcctc ttggcaggct caaaacaagc gacccttggt    1020
gctaaaccag atcatcaaga ggccttcgaa gctactgcaa atcaacagga agtttctgat    1080
accacctctt tcctaggaca ggcctttggt gctatcccac atcaatggga acttcctggt    1140
gctgacccag ttcatggtga ggccctgggt gagaccccag atctaccaga gattcctggt    1200
gctattccag tccaaggaga ggtctttggt actattttag accaacaaga aactcttggt    1260
atgagtggga gtgttgtccc agacttgcct gtcttccttc ctgttcctcc aaatccaatt    1320 gctacctta tgctccttc caaatggcct gagccccaaa gcactgtctc atatggactt    1380
gcagtccagg gtgctataca gattttgcct ttgggctcag gacacactcc tcaatcatca    1440
tcaaactcag agaaaaattc attacctcca gtaatggcta taagcaatgt agaaaatgag    1500
aagcaggttc atataagctt cctgccagct aacactcagg ggttcccatt agcccctgag    1560
agaggactct tccatgcttc actgggtata gcccaactct ctcaggctgg tcctagcaaa    1620
tcagacagag ggagctccca ggtcagtgta accagcacag ttcatgttgt caacaccaca    1680
gtggtgacta tgccagtgcc aatggtcagt acctcctctt cttcctatac cactttgcta    1740
ccgactttgg aaaagaagaa aagaaagcga tgtggggtct gtgaaccctg ccagcagaag    1800
accaactgtg gtgaatgcac ttactgcaag aacagaaaga acagccatca gatctgtaag    1860
aaaagaaaat gtgaggagct gaaaagaaaa ccatctgttg ttgtgcctct ggaggttata    1920
aaggaaaaca agaggcccca gagggaaaag aagcccaaag ttttaaaggc agattttgac    1980
aacaaaccag taaatggccc caagtcagaa tccatggact acagtagatg tggtcatggg    2040
gaagaacaaa aattggaatt gaacccacat actgttgaaa atgtaactaa aaatgaagac    2100
agcatgacag gcatcgaggt ggagaagtgg acacaaaaca gaaatcaca gttaactgat    2160 cacgtgaaag gagattttag tgctaatgtc ccagaagctg aaaaatcgaa aaactctgaa    2220
gttgacaaga aacgaaccaa atctccaaaa ttgtttgtac aaaccgtaag aaatggcatt    2280
aaacatgtac actgtttacc agctgaaaca aatgtttcat ttaaaaaatt caatattgaa    2340
gaattcggca agacattgga aaacaattct tataaattcc taaaagacac tgcaaaccat    2400
```

```
aaaaacgcta tgagctctgt tgctactgat atgagttgtg atcatctcaa ggggagaagt    2460
aacgttttag tattccagca gcctggcttt aactgcagtt ccattccaca ttcttcacac    2520
tccatcataa atcatcatgc tagtatacac aatgaaggtg atcaaccaaa aactcctgag    2580
aatataccaa gtaaagaacc aaaagatgga tctcccgttc aaccaagtct cttatcgtta    2640
atgaaagata ggagattaac attggagcaa gtggtagcca tagaggccct gactcaactc    2700
tcagaagccc catcagagaa ttcctcccca tcaaagtcag agaaggatga ggaatcagag    2760
cagagaacag ccagtttgct taatagctgc aaagctatcc tctacactgt aagaaaagac    2820
ctccaagacc caaacttaca gggagagcca ccaaaactta atcactgtcc atctttggaa    2880
aaacaaagtt catgcaacac ggtggttttc aatgggcaaa ctactaccct ttccaactca    2940
catatcaact cagctactaa ccaagcatcc acaaagtcac atgaatattc aaaagtcaca    3000
aattcattat ctcttttat accaaaatca aattcatcca agattgacac aataaaagt    3060 attgctcaag ggataattac tcttgacaat tgttccaatg atttgcatca gttgccacca    3120
agaaataatg aagtggagta ttgcaaccag ttactggaca gcagcaaaaa attggactca    3180
gatgatctat catgtcagga tgcaacccat acccaaattg aggaagatgt tgcaacacag    3240
ttgacacaac ttgcttcgat aattaagatc aattatataa aaccgagga caaaaaagtt    3300 gaaagtacac caacaagcct tgtcacatgt aatgtacagc aaaaatacaa tcaggagaag    3360
ggcacaatac aacagaaacc accttcaagt gtacacaata atcatggttc atcattaaca    3420
aaacaaaaga acccaacccca gaaaagaca aaatccaccc catcaagaga tcggcggaaa    3480
aagaagccca cagttgtaag ttatcaagaa atgatcggc agaagtggga aaagttgtcc    3540
tatatgtatg gcacaatatg cgacatttgg atagcatcga aatttcaaaa ttttgggcaa    3600
ttttgtccac atgatttttcc tactgtattt gggaaaattt cttcctcgac caaaatatgg    3660
aaaccactgg ctcaaacgag gtccattatg caacccaaaa cagtatttcc accactcact    3720
cagataaaat tacagagata tcctgaatca gcagaggaaa aggtgaaggt tgaaccattg    3780
gattcactca gcttatttca tcttaaaacg gaatccaacg ggaaggcatt cactgataaa    3840
gcttataatt ctcaggtaca gttaacggtg aatgccaatc agaaagccca tccttttgacc    3900 cagccctcct ctccacctaa ccagtgtgct aacgtgatgg caggcgatga ccaaatacgg    3960
tttcagcagg ttgttaagga gcaactcatg catcagagac tgccaacatt gcctggtatc    4020
tctcatgaaa caccccttacc ggagtcagca ctaactctca ggaatgtaaa tgtagtgtgt    4080
tcaggtggaa ttacagtggt ttctaccaaa agtgaagagg aagtctgttc atccagtttt    4140
ggaacatcag aattttccac agtggacagt gcacagaaaa attttaatga ttatgccatg    4200 aacttctttta ctaaccctac aaaaaaccta gtgtctataa ctaaagattc tgaactgccc    4260
acctgcagct gtcttgatcg agttatacaa aaagacaaag gcccatatta tacacacctt    4320
ggggcaggac caagtgttgc tgctgtcagg gaaatcatgg agaataggta tggtcaaaaa    4380
ggaaacgcaa taaggataga aatagtagtg tacaccggta agaaagggaa aagctctcat    4440
gggtgtccaa ttgctaagtg ggttttaaga agaagcagtg atgaagaaaa agttctttgt    4500
ttggtccggc agcgtacagg ccaccactgt ccaactgctg tgatggtggt gctcatcatg    4560
gtgtgggatg gcatccctct tccaatggcc gaccggctat acacagagct cacagagaat    4620
ctaaagtcat acaatgggca ccctaccgac agaagatgca ccctcaatga aaatcgtacc    4680
tgtacatgtc aaggaattga tccagagact tgtggagctt cattctcttt tggctgttca    4740
tggagtatgt actttaatgg ctgtaagttt ggtagaagcc caagccccag aagatttaga    4800
```

-continued

```
attgatccaa gctctccctt acatgaaaaa aaccttgaag ataacttaca gagtttggct   4860
acacgattag ctccaattta taagcagtat gctccagtag cttaccaaaa tcaggtggaa   4920
tatgaaaatg ttgcccgaga atgtcggctt ggcagcaagg aaggtcgtcc cttctctggg   4980
gtcactgctt gcctggactt ctgtgctcat ccccacaggg acattcacaa catgaataat   5040
ggaagcactg tggtttgtac cttaactcga gaagataacc gctctttggg tgttattcct   5100
caagatgagc agctccatgt gctacctctt tataagcttt cagacacaga tgagtttggc   5160
tccaaggaag gaatggaagc caagatcaaa tctggggcca tcgaggtcct ggcaccccgc   5220
cgcaaaaaaa gaacgtgttt cactcagcct gttccccgtt ctggaaagaa gagggctgcg   5280
atgatgacag aggttcttgc acataagata agggcagtgg aaaagaaacc tattccccga   5340
atcaagcgga agaataactc aacaacaaca aacaacagta agccttcgtc actgccaacc   5400
ttagggagta acactgagac cgtgcaacct gaagtaaaaa gtgaaaccga accccatttt   5460
atcttaaaaa gttcagacaa cactaaaact tattcgctga tgccatccgc tcctcaccca   5520
gtgaaagagg catctccagg cttctcctgg tccccgaaga ctgcttcagc cacaccagct   5580
ccactgaaga atgacgcaac agcctcatgc gggttttcag aaagaagcag cactccccac   5640
tgtacgatgc cttcgggaag actcagtggt gccaatgcag ctgctgctga tggccctggc   5700
atttcacagc ttggcgaagt ggctcctctc cccaccctgt ctgctcctgt gatggagccc   5760
ctcattaatt ctgagccttc cactggtgtg actgagccgc taacgcctca tcagccaaac   5820
caccagccct ccttcctcac ctctcctcaa gaccttgcct cttctccaat ggaagaagat   5880
gagcagcatt ctgaagcaga tgagcctcca tcagacgaac ccctatctga tgacccctg    5940 tcacctgctg aggagaaatt gccccacatt gatgagtatt ggtcagacag tgagcacatc   6000
tttttggatg caaatattgg tggggtggcc atcgcacctg ctcacggctc ggttttgatt   6060
gagtgtgccc ggcgagagct gcacgctacc actcctgttg agcacccaa ccgtaatcat    6120 ccaacccgcc tctcccttgt cttttaccag cacaaaaacc taaataagcc caacatggt    6180 tttgaactaa acaagattaa gtttgaggct aaagaagcta agaataagaa aatgaaggcc   6240
tcagagcaaa agaccaggc agctaatgaa ggtccagaac agtcctctga agtaaatgaa    6300
ttgaaccaaa ttccttctca taaagcatta acattaaccc atgacaatgt tgtcaccgtg   6360 tcccctttatg ctctcacaca cgttgcgggg ccctataacc attgggtctg a            6411
```

<210> SEQ ID NO 5
<211> LENGTH: 2136
<212> TYPE: PRT
<213> ORGANISM: Homo sapiens

<400> SEQUENCE: 5

```
Met Ser Arg Ser Arg His Ala Arg Pro Ser Arg Leu Val Arg Lys Glu
1               5                   10                  15

Asp Val Asn Lys Lys Lys Asn Ser Gln Leu Arg Lys Thr Thr Lys
            20                  25                  30

Gly Ala Asn Lys Asn Val Ala Ser Val Lys Thr Leu Ser Pro Gly Lys
        35                  40                  45

Leu Lys Gln Leu Ile Gln Glu Arg Asp Val Lys Lys Thr Glu Pro
    50                  55                  60

Lys Pro Pro Val Pro Val Arg Ser Leu Leu Thr Arg Ala Gly Ala Ala
65                  70                  75                  80

Arg Met Asn Leu Asp Arg Thr Glu Val Leu Phe Gln Asn Pro Glu Ser
```

```
                    85                  90                  95
Leu Thr Cys Asn Gly Phe Thr Met Ala Leu Arg Ser Thr Ser Leu Ser
            100                 105                 110
Arg Arg Leu Ser Gln Pro Pro Leu Val Val Ala Lys Ser Lys Lys Val
            115                 120                 125
Pro Leu Ser Lys Gly Leu Glu Lys Gln His Asp Cys Asp Tyr Lys Ile
            130                 135                 140
Leu Pro Ala Leu Gly Val Lys His Ser Glu Asn Asp Ser Val Pro Met
145                 150                 155                 160
Gln Asp Thr Gln Val Leu Pro Asp Ile Glu Thr Leu Ile Gly Val Gln
                    165                 170                 175
Asn Pro Ser Leu Leu Lys Gly Lys Ser Gln Glu Thr Thr Gln Phe Trp
                    180                 185                 190
Ser Gln Arg Val Glu Asp Ser Lys Ile Asn Ile Pro Thr His Ser Gly
            195                 200                 205
Pro Ala Ala Glu Ile Leu Pro Gly Pro Leu Glu Gly Thr Arg Cys Gly
            210                 215                 220
Glu Gly Leu Phe Ser Glu Glu Thr Leu Asn Asp Thr Ser Gly Ser Pro
225                 230                 235                 240
Lys Met Phe Ala Gln Asp Thr Val Cys Ala Pro Phe Pro Gln Arg Ala
                    245                 250                 255
Thr Pro Lys Val Thr Ser Gln Gly Asn Pro Ser Ile Gln Leu Glu Glu
            260                 265                 270
Leu Gly Ser Arg Val Glu Ser Leu Lys Leu Ser Asp Ser Tyr Leu Asp
            275                 280                 285
Pro Ile Lys Ser Glu His Asp Cys Tyr Pro Thr Ser Ser Leu Asn Lys
            290                 295                 300
Val Ile Pro Asp Leu Asn Leu Arg Asn Cys Leu Ala Leu Gly Gly Ser
305                 310                 315                 320
Thr Ser Pro Thr Ser Val Ile Lys Phe Leu Leu Ala Gly Ser Lys Gln
                    325                 330                 335
Ala Thr Leu Gly Ala Lys Pro Asp His Gln Glu Ala Phe Glu Ala Thr
            340                 345                 350
Ala Asn Gln Gln Glu Val Ser Asp Thr Thr Ser Phe Leu Gly Gln Ala
            355                 360                 365
Phe Gly Ala Ile Pro His Gln Trp Glu Leu Pro Gly Ala Asp Pro Val
            370                 375                 380
His Gly Glu Ala Leu Gly Glu Thr Pro Asp Leu Pro Glu Ile Pro Gly
385                 390                 395                 400
Ala Ile Pro Val Gln Gly Glu Val Phe Gly Thr Ile Leu Asp Gln Gln
                    405                 410                 415
Glu Thr Leu Gly Met Ser Gly Ser Val Val Pro Asp Leu Pro Val Phe
                    420                 425                 430
Leu Pro Val Pro Pro Asn Pro Ile Ala Thr Phe Asn Ala Pro Ser Lys
            435                 440                 445
Trp Pro Glu Pro Gln Ser Thr Val Ser Tyr Gly Leu Ala Val Gln Gly
            450                 455                 460
Ala Ile Gln Ile Leu Pro Leu Gly Ser Gly His Thr Pro Gln Ser Ser
465                 470                 475                 480
Ser Asn Ser Glu Lys Asn Ser Leu Pro Pro Val Met Ala Ile Ser Asn
                    485                 490                 495
Val Glu Asn Glu Lys Gln Val His Ile Ser Phe Leu Pro Ala Asn Thr
            500                 505                 510
```

```
Gln Gly Phe Pro Leu Ala Pro Glu Arg Gly Leu Phe His Ala Ser Leu
            515                 520                 525

Gly Ile Ala Gln Leu Ser Gln Ala Gly Pro Ser Lys Ser Asp Arg Gly
    530                 535                 540

Ser Ser Gln Val Ser Val Thr Ser Thr Val His Val Val Asn Thr Thr
545                 550                 555                 560

Val Val Thr Met Pro Val Pro Met Val Ser Thr Ser Ser Ser Ser Tyr
                565                 570                 575

Thr Thr Leu Leu Pro Thr Leu Glu Lys Lys Arg Lys Arg Cys Gly
                580                 585                 590

Val Cys Glu Pro Cys Gln Gln Lys Thr Asn Cys Gly Glu Cys Thr Tyr
        595                 600                 605

Cys Lys Asn Arg Lys Asn Ser His Gln Ile Cys Lys Lys Arg Lys Cys
        610                 615                 620

Glu Glu Leu Lys Lys Lys Pro Ser Val Val Val Pro Leu Glu Val Ile
625                 630                 635                 640

Lys Glu Asn Lys Arg Pro Gln Arg Glu Lys Lys Pro Lys Val Leu Lys
                645                 650                 655

Ala Asp Phe Asp Asn Lys Pro Val Asn Gly Pro Lys Ser Glu Ser Met
                660                 665                 670

Asp Tyr Ser Arg Cys Gly His Gly Glu Glu Gln Lys Leu Glu Leu Asn
        675                 680                 685

Pro His Thr Val Glu Asn Val Thr Lys Asn Glu Asp Ser Met Thr Gly
        690                 695                 700

Ile Glu Val Glu Lys Trp Thr Gln Asn Lys Lys Ser Gln Leu Thr Asp
705                 710                 715                 720

His Val Lys Gly Asp Phe Ser Ala Asn Val Pro Glu Ala Glu Lys Ser
                725                 730                 735

Lys Asn Ser Glu Val Asp Lys Lys Arg Thr Lys Ser Pro Lys Leu Phe
                740                 745                 750

Val Gln Thr Val Arg Asn Gly Ile Lys His Val His Cys Leu Pro Ala
        755                 760                 765

Glu Thr Asn Val Ser Phe Lys Lys Phe Asn Ile Glu Glu Phe Gly Lys
        770                 775                 780

Thr Leu Glu Asn Asn Ser Tyr Lys Phe Leu Lys Asp Thr Ala Asn His
785                 790                 795                 800

Lys Asn Ala Met Ser Ser Val Ala Thr Asp Met Ser Cys Asp His Leu
                805                 810                 815

Lys Gly Arg Ser Asn Val Leu Val Phe Gln Gln Pro Gly Phe Asn Cys
                820                 825                 830

Ser Ser Ile Pro His Ser Ser His Ser Ile Ile Asn His His Ala Ser
        835                 840                 845

Ile His Asn Glu Gly Asp Gln Pro Lys Thr Pro Glu Asn Ile Pro Ser
        850                 855                 860

Lys Glu Pro Lys Asp Gly Ser Pro Val Gln Pro Ser Leu Leu Ser Leu
865                 870                 875                 880

Met Lys Asp Arg Arg Leu Thr Leu Glu Gln Val Val Ala Ile Glu Ala
                885                 890                 895

Leu Thr Gln Leu Ser Glu Ala Pro Ser Glu Asn Ser Ser Pro Ser Lys
        900                 905                 910

Ser Glu Lys Asp Glu Glu Ser Glu Gln Arg Thr Ala Ser Leu Leu Asn
        915                 920                 925
```

-continued

```
Ser Cys Lys Ala Ile Leu Tyr Thr Val Arg Lys Asp Leu Gln Asp Pro
930                 935                 940

Asn Leu Gln Gly Glu Pro Pro Lys Leu Asn His Cys Pro Ser Leu Glu
945                 950                 955                 960

Lys Gln Ser Ser Cys Asn Thr Val Val Phe Asn Gly Gln Thr Thr Thr
                965                 970                 975

Leu Ser Asn Ser His Ile Asn Ser Ala Thr Asn Gln Ala Ser Thr Lys
                980                 985                 990

Ser His Glu Tyr Ser Lys Val Thr Asn Ser Leu Ser Leu Phe Ile Pro
                995                 1000                1005

Lys Ser Asn Ser Ser Lys Ile Asp Thr Asn Lys Ser Ile Ala Gln
    1010                1015                1020

Gly Ile Ile Thr Leu Asp Asn Cys Ser Asn Asp Leu His Gln Leu
    1025                1030                1035

Pro Pro Arg Asn Asn Glu Val Glu Tyr Cys Asn Gln Leu Leu Asp
    1040                1045                1050

Ser Ser Lys Lys Leu Asp Ser Asp Asp Leu Ser Cys Gln Asp Ala
    1055                1060                1065

Thr His Thr Gln Ile Glu Glu Asp Val Ala Thr Gln Leu Thr Gln
    1070                1075                1080

Leu Ala Ser Ile Ile Lys Ile Asn Tyr Ile Lys Pro Glu Asp Lys
    1085                1090                1095

Lys Val Glu Ser Thr Pro Thr Ser Leu Val Thr Cys Asn Val Gln
    1100                1105                1110

Gln Lys Tyr Asn Gln Glu Lys Gly Thr Ile Gln Gln Lys Pro Pro
    1115                1120                1125

Ser Ser Val His Asn Asn His Gly Ser Ser Leu Thr Lys Gln Lys
    1130                1135                1140

Asn Pro Thr Gln Lys Lys Thr Lys Ser Thr Pro Ser Arg Asp Arg
    1145                1150                1155

Arg Lys Lys Lys Pro Thr Val Val Ser Tyr Gln Glu Asn Asp Arg
    1160                1165                1170

Gln Lys Trp Glu Lys Leu Ser Tyr Met Tyr Gly Thr Ile Cys Asp
    1175                1180                1185

Ile Trp Ile Ala Ser Lys Phe Gln Asn Phe Gly Gln Phe Cys Pro
    1190                1195                1200

His Asp Phe Pro Thr Val Phe Gly Lys Ile Ser Ser Ser Thr Lys
    1205                1210                1215

Ile Trp Lys Pro Leu Ala Gln Thr Arg Ser Ile Met Gln Pro Lys
    1220                1225                1230

Thr Val Phe Pro Pro Leu Thr Gln Ile Lys Leu Gln Arg Tyr Pro
    1235                1240                1245

Glu Ser Ala Glu Glu Lys Val Lys Val Glu Pro Leu Asp Ser Leu
    1250                1255                1260

Ser Leu Phe His Leu Lys Thr Glu Ser Asn Gly Lys Ala Phe Thr
    1265                1270                1275

Asp Lys Ala Tyr Asn Ser Gln Val Gln Leu Thr Val Asn Ala Asn
    1280                1285                1290

Gln Lys Ala His Pro Leu Thr Gln Pro Ser Ser Pro Asn Gln
    1295                1300                1305

Cys Ala Asn Val Met Ala Gly Asp Asp Gln Ile Arg Phe Gln Gln
    1310                1315                1320

Val Val Lys Glu Gln Leu Met His Gln Arg Leu Pro Thr Leu Pro
```

```
                1325                1330                1335
Gly Ile Ser His Glu Thr Pro Leu Pro Glu Ser Ala Leu Thr Leu
            1340                1345                1350
Arg Asn Val Asn Val Val Cys Ser Gly Gly Ile Thr Val Val Ser
            1355                1360                1365
Thr Lys Ser Glu Glu Glu Val Cys Ser Ser Phe Gly Thr Ser
            1370                1375                1380
Glu Phe Ser Thr Val Asp Ser Ala Gln Lys Asn Phe Asn Asp Tyr
            1385                1390                1395
Ala Met Asn Phe Phe Thr Asn Pro Thr Lys Asn Leu Val Ser Ile
            1400                1405                1410
Thr Lys Asp Ser Glu Leu Pro Thr Cys Ser Cys Leu Asp Arg Val
            1415                1420                1425
Ile Gln Lys Asp Lys Gly Pro Tyr Tyr Thr His Leu Gly Ala Gly
            1430                1435                1440
Pro Ser Val Ala Ala Val Arg Glu Ile Met Glu Asn Arg Tyr Gly
            1445                1450                1455
Gln Lys Gly Asn Ala Ile Arg Ile Glu Ile Val Val Tyr Thr Gly
            1460                1465                1470
Lys Glu Gly Lys Ser Ser His Gly Cys Pro Ile Ala Lys Trp Val
            1475                1480                1485
Leu Arg Arg Ser Ser Asp Glu Glu Lys Val Leu Cys Leu Val Arg
            1490                1495                1500
Gln Arg Thr Gly His His Cys Pro Thr Ala Val Met Val Val Leu
            1505                1510                1515
Ile Met Val Trp Asp Gly Ile Pro Leu Pro Met Ala Asp Arg Leu
            1520                1525                1530
Tyr Thr Glu Leu Thr Glu Asn Leu Lys Ser Tyr Asn Gly His Pro
            1535                1540                1545
Thr Asp Arg Arg Cys Thr Leu Asn Glu Asn Arg Thr Cys Thr Cys
            1550                1555                1560
Gln Gly Ile Asp Pro Glu Thr Cys Gly Ala Ser Phe Ser Phe Gly
            1565                1570                1575
Cys Ser Trp Ser Met Tyr Phe Asn Gly Cys Lys Phe Gly Arg Ser
            1580                1585                1590
Pro Ser Pro Arg Arg Phe Arg Ile Asp Pro Ser Ser Pro Leu His
            1595                1600                1605
Glu Lys Asn Leu Glu Asp Asn Leu Gln Ser Leu Ala Thr Arg Leu
            1610                1615                1620
Ala Pro Ile Tyr Lys Gln Tyr Ala Pro Val Ala Tyr Gln Asn Gln
            1625                1630                1635
Val Glu Tyr Glu Asn Val Ala Arg Glu Cys Arg Leu Gly Ser Lys
            1640                1645                1650
Glu Gly Arg Pro Phe Ser Gly Val Thr Ala Cys Leu Asp Phe Cys
            1655                1660                1665
Ala His Pro His Arg Asp Ile His Asn Met Asn Asn Gly Ser Thr
            1670                1675                1680
Val Val Cys Thr Leu Thr Arg Glu Asp Asn Arg Ser Leu Gly Val
            1685                1690                1695
Ile Pro Gln Asp Glu Gln Leu His Val Leu Pro Leu Tyr Lys Leu
            1700                1705                1710
Ser Asp Thr Asp Glu Phe Gly Ser Lys Glu Gly Met Glu Ala Lys
            1715                1720                1725
```

-continued

```
Ile Lys Ser Gly Ala Ile Glu Val Leu Ala Pro Arg Arg Lys Lys
    1730                1735                1740

Arg Thr Cys Phe Thr Gln Pro Val Pro Arg Ser Gly Lys Lys Arg
    1745                1750                1755

Ala Ala Met Met Thr Glu Val Leu Ala His Lys Ile Arg Ala Val
    1760                1765                1770

Glu Lys Lys Pro Ile Pro Arg Ile Lys Arg Lys Asn Asn Ser Thr
    1775                1780                1785

Thr Thr Asn Asn Ser Lys Pro Ser Ser Leu Pro Thr Leu Gly Ser
    1790                1795                1800

Asn Thr Glu Thr Val Gln Pro Glu Val Lys Ser Glu Thr Glu Pro
    1805                1810                1815

His Phe Ile Leu Lys Ser Ser Asp Asn Thr Lys Thr Tyr Ser Leu
    1820                1825                1830

Met Pro Ser Ala Pro His Pro Val Lys Glu Ala Ser Pro Gly Phe
    1835                1840                1845

Ser Trp Ser Pro Lys Thr Ala Ser Ala Thr Pro Ala Pro Leu Lys
    1850                1855                1860

Asn Asp Ala Thr Ala Ser Cys Gly Phe Ser Glu Arg Ser Ser Thr
    1865                1870                1875

Pro His Cys Thr Met Pro Ser Gly Arg Leu Ser Gly Ala Asn Ala
    1880                1885                1890

Ala Ala Ala Asp Gly Pro Gly Ile Ser Gln Leu Gly Glu Val Ala
    1895                1900                1905

Pro Leu Pro Thr Leu Ser Ala Pro Val Met Glu Pro Leu Ile Asn
    1910                1915                1920

Ser Glu Pro Ser Thr Gly Val Thr Glu Pro Leu Thr Pro His Gln
    1925                1930                1935

Pro Asn His Gln Pro Ser Phe Leu Thr Ser Pro Gln Asp Leu Ala
    1940                1945                1950

Ser Ser Pro Met Glu Glu Asp Glu Gln His Ser Glu Ala Asp Glu
    1955                1960                1965

Pro Pro Ser Asp Glu Pro Leu Ser Asp Asp Pro Leu Ser Pro Ala
    1970                1975                1980

Glu Glu Lys Leu Pro His Ile Asp Glu Tyr Trp Ser Asp Ser Glu
    1985                1990                1995

His Ile Phe Leu Asp Ala Asn Ile Gly Gly Val Ala Ile Ala Pro
    2000                2005                2010

Ala His Gly Ser Val Leu Ile Glu Cys Ala Arg Arg Glu Leu His
    2015                2020                2025

Ala Thr Thr Pro Val Glu His Pro Asn Arg Asn His Pro Thr Arg
    2030                2035                2040

Leu Ser Leu Val Phe Tyr Gln His Lys Asn Leu Asn Lys Pro Gln
    2045                2050                2055

His Gly Phe Glu Leu Asn Lys Ile Lys Phe Glu Ala Lys Glu Ala
    2060                2065                2070

Lys Asn Lys Lys Met Lys Ala Ser Glu Gln Lys Asp Gln Ala Ala
    2075                2080                2085

Asn Glu Gly Pro Glu Gln Ser Ser Glu Val Asn Glu Leu Asn Gln
    2090                2095                2100

Ile Pro Ser His Lys Ala Leu Thr Leu Thr His Asp Asn Val Val
    2105                2110                2115
```

Thr Val Ser Pro Tyr Ala Leu Thr His Val Ala Gly Pro Tyr Asn
    2120                2125                2130

His Trp Val
    2135

<210> SEQ ID NO 6
<211> LENGTH: 719
<212> TYPE: PRT
<213> ORGANISM: Homo sapiens

<400> SEQUENCE: 6

Glu Leu Pro Thr Cys Ser Cys Leu Asp Arg Val Ile Gln Lys Asp Lys
1               5                   10                  15

Gly Pro Tyr Tyr Thr His Leu Gly Ala Gly Pro Ser Val Ala Ala Val
            20                  25                  30

Arg Glu Ile Met Glu Asn Arg Tyr Gly Gln Lys Gly Asn Ala Ile Arg
        35                  40                  45

Ile Glu Ile Val Val Tyr Thr Gly Lys Glu Gly Lys Ser Ser His Gly
    50                  55                  60

Cys Pro Ile Ala Lys Trp Val Leu Arg Arg Ser Ser Asp Glu Glu Lys
65                  70                  75                  80

Val Leu Cys Leu Val Arg Gln Arg Thr Gly His His Cys Pro Thr Ala
                85                  90                  95

Val Met Val Val Leu Ile Met Val Trp Asp Gly Ile Pro Leu Pro Met
            100                 105                 110

Ala Asp Arg Leu Tyr Thr Glu Leu Thr Glu Asn Leu Lys Ser Tyr Asn
        115                 120                 125

Gly His Pro Thr Asp Arg Arg Cys Thr Leu Asn Glu Asn Arg Thr Cys
    130                 135                 140

Thr Cys Gln Gly Ile Asp Pro Glu Thr Cys Gly Ala Ser Phe Ser Phe
145                 150                 155                 160

Gly Cys Ser Trp Ser Met Tyr Phe Asn Gly Cys Lys Phe Gly Arg Ser
                165                 170                 175

Pro Ser Pro Arg Arg Phe Arg Ile Asp Pro Ser Ser Pro Leu His Glu
            180                 185                 190

Lys Asn Leu Glu Asp Asn Leu Gln Ser Leu Ala Thr Arg Leu Ala Pro
        195                 200                 205

Ile Tyr Lys Gln Tyr Ala Pro Val Ala Tyr Gln Asn Gln Val Glu Tyr
    210                 215                 220

Glu Asn Val Ala Arg Glu Cys Arg Leu Gly Ser Lys Glu Gly Arg Pro
225                 230                 235                 240

Phe Ser Gly Val Thr Ala Cys Leu Asp Phe Cys Ala His Pro His Arg
                245                 250                 255

Asp Ile His Asn Met Asn Asn Gly Ser Thr Val Val Cys Thr Leu Thr
            260                 265                 270

Arg Glu Asp Asn Arg Ser Leu Gly Val Ile Pro Gln Asp Glu Gln Leu
        275                 280                 285

His Val Leu Pro Leu Tyr Lys Leu Ser Asp Thr Asp Glu Phe Gly Ser
    290                 295                 300

Lys Glu Gly Met Glu Ala Lys Ile Lys Ser Gly Ala Ile Glu Val Leu
305                 310                 315                 320

Ala Pro Arg Arg Lys Lys Arg Thr Cys Phe Thr Gln Pro Val Pro Arg
                325                 330                 335

Ser Gly Lys Lys Arg Ala Ala Met Met Thr Glu Val Leu Ala His Lys
            340                 345                 350

Ile Arg Ala Val Glu Lys Lys Pro Ile Pro Arg Ile Lys Arg Lys Asn
            355                 360                 365

Asn Ser Thr Thr Thr Asn Asn Ser Lys Pro Ser Ser Leu Pro Thr Leu
370                 375                 380

Gly Ser Asn Thr Glu Thr Val Gln Pro Glu Val Lys Ser Glu Thr Glu
385                 390                 395                 400

Pro His Phe Ile Leu Lys Ser Ser Asp Asn Thr Lys Thr Tyr Ser Leu
                405                 410                 415

Met Pro Ser Ala Pro His Pro Val Lys Glu Ala Ser Pro Gly Phe Ser
            420                 425                 430

Trp Ser Pro Lys Thr Ala Ser Ala Thr Pro Ala Pro Leu Lys Asn Asp
            435                 440                 445

Ala Thr Ala Ser Cys Gly Phe Ser Glu Arg Ser Ser Thr Pro His Cys
            450                 455                 460

Thr Met Pro Ser Gly Arg Leu Ser Gly Ala Asn Ala Ala Ala Ala Asp
465                 470                 475                 480

Gly Pro Gly Ile Ser Gln Leu Gly Glu Val Ala Pro Leu Pro Thr Leu
                485                 490                 495

Ser Ala Pro Val Met Glu Pro Leu Ile Asn Ser Glu Pro Ser Thr Gly
            500                 505                 510

Val Thr Glu Pro Leu Thr Pro His Gln Pro Asn His Gln Pro Ser Phe
            515                 520                 525

Leu Thr Ser Pro Gln Asp Leu Ala Ser Ser Pro Met Glu Glu Asp Glu
            530                 535                 540

Gln His Ser Glu Ala Asp Glu Pro Pro Ser Asp Glu Pro Leu Ser Asp
545                 550                 555                 560

Asp Pro Leu Ser Pro Ala Glu Glu Lys Leu Pro His Ile Asp Glu Tyr
                565                 570                 575

Trp Ser Asp Ser Glu His Ile Phe Leu Asp Ala Asn Ile Gly Gly Val
            580                 585                 590

Ala Ile Ala Pro Ala His Gly Ser Val Leu Ile Glu Cys Ala Arg Arg
            595                 600                 605

Glu Leu His Ala Thr Thr Pro Val Glu His Pro Asn Arg Asn His Pro
            610                 615                 620

Thr Arg Leu Ser Leu Val Phe Tyr Gln His Lys Asn Leu Asn Lys Pro
625                 630                 635                 640

Gln His Gly Phe Glu Leu Asn Lys Ile Lys Phe Glu Ala Lys Glu Ala
                645                 650                 655

Lys Asn Lys Lys Met Lys Ala Ser Glu Gln Lys Asp Gln Ala Ala Asn
            660                 665                 670

Glu Gly Pro Glu Gln Ser Ser Glu Val Asn Glu Leu Asn Gln Ile Pro
            675                 680                 685

Ser His Lys Ala Leu Thr Leu Thr His Asp Asn Val Val Thr Val Ser
            690                 695                 700

Pro Tyr Ala Leu Thr His Val Ala Gly Pro Tyr Asn His Trp Val
705                 710                 715

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
gtgccaatgg tcagtacctc                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic construct

<400> SEQUENCE: 8
ctgtagtcca tggattctga                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
ctggatgcgc aagctgcaca                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
ccatgctcat gcttttcagc                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
gtgtaccacc accatcacca                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
agcgcgcatg aagccagttg                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13
gttccgagta cctgaagatc                                              20

<210> SEQ ID NO 14
<211> LENGTH: 20
<212> TYPE: DNA

```
<213> ORGANISM: Artificial Sequence
<220> FEATURE:
<223> OTHER INFORMATION: Synthetic construct

<400> SEQUENCE: 14
gtgttgtcgt tgatgtcaag                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
tagggacgga caaagagctg                                                  20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
ttggatgtcc tccattcccc                                                  20

<210> SEQ ID NO 17
<211> LENGTH: 19
<212> TYPE: DNA
<213> ORGANISM: Artificial Sequence
<220> FEATURE:
<223> OTHER INFORMATION: Synthetic construct

<400> SEQUENCE: 17
ggagccagag aggccgatg                                                   19

<210> SEQ ID NO 18
<211> LENGTH: 21
<212> TYPE: DNA
<213> ORGANISM: Artificial Sequence
<220> FEATURE:
<223> OTHER INFORMATION: Synthetic construct

<400> SEQUENCE: 18
atggcgttgg tatgagctgt g                                                21

<210> SEQ ID NO 19
<211> LENGTH: 20
<212> TYPE: DNA
<213> ORGANISM: Artificial Sequence
<220> FEATURE:
<223> OTHER INFORMATION: Synthetic construct

<400> SEQUENCE: 19
tgctggcgat cctgaacaag                                                  20

<210> SEQ ID NO 20
<211> LENGTH: 20
<212> TYPE: DNA
<213> ORGANISM: Artificial Sequence
<220> FEATURE:
<223> OTHER INFORMATION: Synthetic construct

<400> SEQUENCE: 20
aagatcctgg aatgctcctc                                                  20
```

<210> SEQ ID NO 21
<211> LENGTH: 20
<212> TYPE: DNA
<213> ORGANISM: Artificial Sequence
<220> FEATURE:
<223> OTHER INFORMATION: Synthetic construct

<400> SEQUENCE: 21
ccttacaggg atcagtgtca                                           20

<210> SEQ ID NO 22
<211> LENGTH: 20
<212> TYPE: DNA
<213> ORGANISM: Artificial Sequence
<220> FEATURE:
<223> OTHER INFORMATION: Synthetic construct

<400> SEQUENCE: 22
caacttgcgg atcatatcag                                           20

<210> SEQ ID NO 23
<211> LENGTH: 20
<212> TYPE: DNA
<213> ORGANISM: Artificial Sequence
<220> FEATURE:
<223> OTHER INFORMATION: Synthetic construct

<400> SEQUENCE: 23
atctctgccc cctctgctga                                           20

<210> SEQ ID NO 24
<211> LENGTH: 20
<212> TYPE: DNA
<213> ORGANISM: Artificial Sequence
<220> FEATURE:
<223> OTHER INFORMATION: Synthetic construct

<400> SEQUENCE: 24
gatgaccttg cccacagcct                                           20

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
gtgccaatgg tcagtacctc                                           20

<210> SEQ ID NO 26
<211> LENGTH: 20
<212> TYPE: DNA
<213> ORGANISM: Artificial Sequence
<220> FEATURE:
<223> OTHER INFORMATION: Synthetic construct

<400> SEQUENCE: 26
gacactagaa gtgtctctgc                                           20

<210> SEQ ID NO 27
<211> LENGTH: 20
<212> TYPE: DNA
<213> ORGANISM: Artificial Sequence
<220> FEATURE:

<223> OTHER INFORMATION: Synthetic construct

<400> SEQUENCE: 27
tgcgattaca ggtgtgagtc                                          20

<210> SEQ ID NO 28
<211> LENGTH: 20
<212> TYPE: DNA
<213> ORGANISM: Artificial Sequence
<220> FEATURE:
<223> OTHER INFORMATION: Synthetic construct

<400> SEQUENCE: 28
ctgtagtcca tggattctga                                          20

<210> SEQ ID NO 29
<211> LENGTH: 20
<212> TYPE: DNA
<213> ORGANISM: Artificial Sequence
<220> FEATURE:
<223> OTHER INFORMATION: Synthetic construct

<400> SEQUENCE: 29
gcctcactcc ttttgcagac                                          20

<210> SEQ ID NO 30
<211> LENGTH: 20
<212> TYPE: DNA
<213> ORGANISM: Artificial Sequence
<220> FEATURE:
<223> OTHER INFORMATION: Synthetic construct

<400> SEQUENCE: 30
gatgaccttg cccacagcct                                          20

<210> SEQ ID NO 31
<211> LENGTH: 18
<212> TYPE: DNA
<213> ORGANISM: Artificial Sequence
<220> FEATURE:
<223> OTHER INFORMATION: Synthetic construct

<400> SEQUENCE: 31
gtcggtaggg tttttcgc                                            18

<210> SEQ ID NO 32
<211> LENGTH: 19
<212> TYPE: DNA
<213> ORGANISM: Artificial Sequence
<220> FEATURE:
<223> OTHER INFORMATION: Synthetic construct

<400> SEQUENCE: 32
cccaactcac cgctaaccg                                           19

<210> SEQ ID NO 33
<211> LENGTH: 21
<212> TYPE: DNA
<213> ORGANISM: Artificial Sequence
<220> FEATURE:
<223> OTHER INFORMATION: Synthetic construct

<400> SEQUENCE: 33
gagttggtag gtgttttttg t                                        21

```
<210> SEQ ID NO 34
<211> LENGTH: 19
<212> TYPE: DNA
<213> ORGANISM: Artificial Sequence
<220> FEATURE:
<223> OTHER INFORMATION: Synthetic construct

<400> SEQUENCE: 34
cccaactcac cactaacca                                                  19

<210> SEQ ID NO 35
<211> LENGTH: 20
<212> TYPE: DNA
<213> ORGANISM: Artificial Sequence
<220> FEATURE:
<223> OTHER INFORMATION: Synthetic construct

<400> SEQUENCE: 35
attcgttttt gttgggcgtc                                                 20

<210> SEQ ID NO 36
<211> LENGTH: 21
<212> TYPE: DNA
<213> ORGANISM: Artificial Sequence
<220> FEATURE:
<223> OTHER INFORMATION: Synthetic construct

<400> SEQUENCE: 36
gcaacgaata caacgttaac g                                               21

<210> SEQ ID NO 37
<211> LENGTH: 22
<212> TYPE: DNA
<213> ORGANISM: Artificial Sequence
<220> FEATURE:
<223> OTHER INFORMATION: Synthetic construct

<400> SEQUENCE: 37
ggatttgttt ttgttgggtg tt                                              22

<210> SEQ ID NO 38
<211> LENGTH: 23
<212> TYPE: DNA
<213> ORGANISM: Artificial Sequence
<220> FEATURE:
<223> OTHER INFORMATION: Synthetic construct

<400> SEQUENCE: 38
ccacaacaaa tacaacatta aca                                             23

<210> SEQ ID NO 39
<211> LENGTH: 19
<212> TYPE: DNA
<213> ORGANISM: Artificial Sequence
<220> FEATURE:
<223> OTHER INFORMATION: Synthetic construct

<400> SEQUENCE: 39
gatcggttta ggttgcggc                                                  19

<210> SEQ ID NO 40
<211> LENGTH: 21
<212> TYPE: DNA
<213> ORGANISM: Artificial Sequence
<220> FEATURE:
<223> OTHER INFORMATION: Synthetic construct
```

<400> SEQUENCE: 40
aacaactaaa cataacgcgc g                                        21

<210> SEQ ID NO 41
<211> LENGTH: 20
<212> TYPE: DNA
<213> ORGANISM: Artificial Sequence
<220> FEATURE:
<223> OTHER INFORMATION: Synthetic construct

<400> SEQUENCE: 41
ggattggttt aggttgtggt                                          20

<210> SEQ ID NO 42
<211> LENGTH: 23
<212> TYPE: DNA
<213> ORGANISM: Artificial Sequence
<220> FEATURE:
<223> OTHER INFORMATION: Synthetic construct

<400> SEQUENCE: 42
aaaacaacta aacataacac aca                                      23

<210> SEQ ID NO 43
<211> LENGTH: 20
<212> TYPE: DNA
<213> ORGANISM: Artificial Sequence
<220> FEATURE:
<223> OTHER INFORMATION: Synthetic construct

<400> SEQUENCE: 43
ggcgattaac gggtcgtttc                                          20

<210> SEQ ID NO 44
<211> LENGTH: 21
<212> TYPE: DNA
<213> ORGANISM: Artificial Sequence
<220> FEATURE:
<223> OTHER INFORMATION: Synthetic construct

<400> SEQUENCE: 44
aaaatttcca aacccgactc g                                        21

<210> SEQ ID NO 45
<211> LENGTH: 22
<212> TYPE: DNA
<213> ORGANISM: Artificial Sequence
<220> FEATURE:
<223> OTHER INFORMATION: Synthetic construct

<400> SEQUENCE: 45
gtggtgatta atgggttgtt tt                                       22

<210> SEQ ID NO 46
<211> LENGTH: 22
<212> TYPE: DNA
<213> ORGANISM: Artificial Sequence
<220> FEATURE:
<223> OTHER INFORMATION: Synthetic construct

<400> SEQUENCE: 46
caaaatttcc aacccaact ca                                        22

<210> SEQ ID NO 47
<211> LENGTH: 24

```
<212> TYPE: DNA
<213> ORGANISM: Artificial Sequence
<220> FEATURE:
<223> OTHER INFORMATION: Synthetic construct

<400> SEQUENCE: 47 ttgtttttttt attgtggatt tttg                                           24

<210> SEQ ID NO 48
<211> LENGTH: 19
<212> TYPE: DNA
<213> ORGANISM: Artificial Sequence
<220> FEATURE:
<223> OTHER INFORMATION: Synthetic construct

<400> SEQUENCE: 48
aacccacccc taaaacaac                                                  19

<210> SEQ ID NO 49
<211> LENGTH: 61
<212> TYPE: DNA
<213> ORGANISM: Artificial Sequence
<220> FEATURE:
<223> OTHER INFORMATION: Synthetic construct

<400> SEQUENCE: 49
cggaattcgc caccatggat tacaaggatg acgacgataa gtacccatac gatgttccag     60
a                                                                     61

<210> SEQ ID NO 50
<211> LENGTH: 48
<212> TYPE: DNA
<213> ORGANISM: Artificial Sequence
<220> FEATURE:
<223> OTHER INFORMATION: Synthetic construct

<400> SEQUENCE: 50
gctctagatt agtggtgatg gtgatgatgg acccaatggt tatagggc                  48

<210> SEQ ID NO 51
<211> LENGTH: 4
<212> TYPE: PRT
<213> ORGANISM: Unknown
<220> FEATURE:
<223> OTHER INFORMATION: CXXC domain
<220> FEATURE:
<221> NAME/KEY: misc_feature
<222> LOCATION: (2)..(3)
<223> OTHER INFORMATION: Xaa can be any naturally occurring amino acid

<400> SEQUENCE: 51

Cys Xaa Xaa Cys
1
```

TUMOR SUPPRESSOR TET1 AND USES THEREOF

RELATED APPLICATIONS

This application claims priority to U.S. Provisional Patent Application No. 62/511,630, filed May 26, 2017, the contents of which are hereby incorporated in the entirety for all purposes.

REFERENCE TO A "SEQUENCE LISTING" SUBMITTED AS ASCII TEXT FILES VIA EFS-WEB

The Sequence Listing written in file 080015-022210US-1088068_SequenceListing.txt created on Aug. 14, 2018, 55,934 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

Cancer is one of the leading causes of morbidity and mortality worldwide, with approximately 15 million new cases diagnosed in each year of this decade. The number of new cases is expected to rise by about 70% over the next 2 decades. The second leading cause of death globally, cancer was responsible for 8.8 million deaths in 2015. The cost for treating cancer is extremely high: for example, in the year of 2014, approximately 88 billion US dollars was spent for cancer treatment in this country alone.

Diagnosis of cancer can be challenging. Although family history may provide useful implications for diagnosis, a significant percentage of cancer occurs in people with little or no genetic risk. Depending on the specific type, symptoms of cancer may not be detectable until the disease has developed to an advanced stage or even has already spread from the primary location to secondary locations (i.e., metastasized). Such delay in diagnosis can make treatment of cancer difficult or even completely ineffective, resulting in poor prognosis.

Because of the high prevalence of cancer and the vital importance of early diagnosis on patients' life expectancy, there exists an urgent need for new and more effective methods to diagnose, monitor, and treat cancer. This invention fulfills this and other related needs.

BRIEF SUMMARY OF THE INVENTION

The present inventors have identified TET1 as a novel tumor suppressor and diagnostic/prognostic marker for multiple types of human cancer, for example, nasopharyngeal cancer (NPC), esophageal cancer (ESCC), lung cancer, hepatocellular cancer (HCC), cervical cancer, renal cancer, and prostate cancer, as well as blood malignancies such as leukemias and lymphomas. More specifically, the inventors show that, compared with normal individuals, CpG islands of the TET1 gene (especially in the promoter region) are hypermethylated in biological samples of cancer tissues from cancer patients. Such hypermethylation leads to TET1 silencing at both mRNA and protein levels.

As such, in the first aspect, the present invention provides a method for assessing the risk for cancer in a subject, i.e., the likelihood of cancer being present in the subject and/or the likelihood of the subject developing cancer at a later time. The method includes the steps of: (a) treating DNA from a biological sample taken from the subject with an agent that differentially modifies methylated and unmethylated DNA; (b) determining number of methylated CpGs in a genomic sequence, which is SEQ ID NO:1 or 2, or a fragment thereof comprising at least 5 CpGs, and (c) comparing the number of methylated CpGs determined in step (b) with the number of methylated CpGs in the same genomic sequence from a non-cancer biological sample of the same type and processed through steps (a) and (b); and (d) determining the subject, whose sample contains more methylated CpGs in the genomic sequence determined in step (b) compared to the number of methylated CpGs in the genomic sequence from the non-cancer sample and processed through steps (a) to (b), as having an increased risk for cancer compared with a healthy subject not diagnosed with cancer.

In some embodiments, the biological sample is a tissue sample, such as a nasopharyngeal sample (testing for nasopharyngeal carcinoma, NPC), esophageal tissue sample (testing for esophageal squamous cell carcinoma, ESCC), lung tissue sample, hepatocellular tissue sample (testing for hepatocellular carcinoma, HCC), breast tissue sample, cervical tissue sample, renal tissue sample, or prostate tissue sample. In some cases, the sample is a nasal or oral swab. In other cases, the sample is a blood sample, for example, an all blood cell sample, a white blood cell sample, or a platelet cell sample. In some embodiments, the agent that differentially modifies methylated DNA and unmethylated DNA is an enzyme that preferentially cleaves methylated DNA, an enzyme that preferentially cleaves unmethylated DNA, or the agent may comprise a bisulfite. In some embodiments, step (b) comprises an amplification reaction, such as a polymerase chain reaction (PCR). In some embodiments, step (b) comprises a polynucleotide sequencing reaction. In some embodiments, step (b) comprises a polynucleotide hybridization assay.

In some embodiments, the CpG-containing genomic sequence being at least a segment of SEQ ID NO:1 or SEQ ID NO:2 and comprising at least 1, 2, 3, 4, 5, 10, 15, 20, 25, 30, 35, or more and up to 39 CpG pairs. When the presence of at least one, or at least 5, or at least 12 methylated CpGs (for example, at least 50% of total CpGs), is detected in the CpG-containing genomic sequence, it indicates that the subject may have cancer or is at an increased risk of developing cancer, especially in the organ or tissue corresponding to the test sample. For example, if methylation is detected in a breast tissue sample, the increased risk of breast cancer is detected. In some cases, the number of methylated CpGs is compared with a control number, e.g., the number of methylated CpGs in the same genomic sequence determined following the same process described above using a sample of the same type from non-cancerous tissue originated from a healthy control subject who has been determined as having no cancer or no known risk for cancer. When the number of methylated CpGs is higher in the test subject compared to the control number, the test subject is determined as having cancer or having an increased risk for cancer; otherwise the test subject is determined as not having cancer or not having any elevated risk for developing cancer.

In some embodiments, the CpG-containing genomic sequence contains at least five and optionally more CpGs (e.g., 10, 15, 20, 25, 30, or 35 CpGs), and when at least 50% of all CpGs being highly methylated (for example, at least 20 of the 39 CpGs in SEQ ID NO:1 being highly or nearly 100% methylated) or when at least 90% of all CpGs being at least 50% methylated (for example, at least 35 of the 39

CpGs in SEQ ID NO:1 being moderately or 50-100% methylated), the subject is indicated as having or at an increased risk for cancer. In some cases, the CpG-containing genomic sequence is a segment of at least 15, 20, 50, 100, 125, 150, 200, 250, 300, or more contiguous nucleotides of SEQ ID NO:1. In other cases, the CpG-containing genomic sequence is SEQ ID NO:1. In one embodiment of the claimed method, the CpG-containing genomic sequence is SEQ ID NO:2, a segment of SEQ ID NO:1, and when at least 5, 10, 12, 15, 20, or more of all CpGs in this CpG-containing genomic sequence are methylated (at least 50% and up to 100% methylated), the subject is indicated as having cancer or having an increased risk for cancer.

In some embodiments, the agent used in the claimed method to differentially modify methylated DNA and unmethylated DNA is an enzyme that preferentially cleaves methylated DNA, an enzyme that preferentially cleaves unmethylated DNA, or a bisulfite (e.g., sodium bisulfite). In other embodiments, step (b) of the method involves an amplification reaction; or step (b) may involve sequencing of a DNA molecule.

In a second aspect, the present invention provides a kit for assessing cancer risk in a subject. The kit comprises (1) two oligonucleotide primers capable of specifically amplifying a genomic sequence of human TET1 gene, such as SEQ ID NO:1 (+151 to +534 of TET1 genomic sequence, +1 denoting translation start) or SEQ ID NO:2 (+221 to +393 of TET1 genomic sequence) or a fragment thereof comprising at least 5 CpGs; and (2) an agent that differentially modifies methylated DNA and unmethylated DNA. In some embodiments, the agent in (2) is an enzyme that preferentially cleaves methylated DNA, an enzyme that preferentially cleaves unmethylated DNA, or a bisulfite. In some embodiments, the genomic sequence is a fragment of SEQ ID NO:1 comprising at least 10, 15, 20, 25, 30, or 35 CpGs, or the genomic sequence is SEQ ID NO:1. In some embodiments, the kit further comprises an oligonucleotide probe for specifically hybridizing with at least a fragment of SEQ ID NO:1 comprising at least 5, 10, 15, 20, 25, 30, or 35 CpGs or the complement thereof, for example, the probe may specifically hybridize with a fragment or the full length of SEQ ID NO:1 in the unmethylated version after bisulfite treatment; or the probe may specifically hybridize with a fragment or the full length of SEQ ID NO:1 in the methylated version after bisulfite treatment. The probe is labeled with a detectable moiety for ready detection. Typically, the kit will further include an instruction manual.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) Representative methylome data. TET1 gene structure, promoter and exon 1 (NCBI database GRCh37.p13) are shown on the top panel. E1: exon 1. Positive methylation signal peaks identified by MeDIP-chip are shown in pink shadow for: NPC xenografts (C15, C18) and primary tumor (OCT83), ESCC cell lines (KYSE140, KYSE510), HCC cell lines (HuH7, HepG2) and primary tumor (HCC418T), NKTCL cell lines (SNK6, NK-YS) and primary tumor (NK1). (FIG. 1B) Expression of TET family genes (TET1, -2, -3) in human normal adult and fetal tissues. Semi-quantitative RT-PCR detected the expression of all TET genes in adult tissues, with GAPDH as a control. Sk.M., skeleton muscle.

FIGS. 2A-2E TET1 is downregulated and methylated in multiple cancers. (FIG. 2A) Structure of the TET1 promoter CpG island (CGI). CpG sites are shown as short vertical lines. MSP primer sites and BGS region analyzed are also indicated. (FIG. 2B) TET1 methylation was not detected in not-bisulfited DNA samples, indicating that the MSP system is specific. m4/m8 represents specific MSP primer set of TET1 methylation detection. (FIGS. 2C, 2D) TET1 was frequently silenced and methylated in multiple carcinoma and lymphoma cell lines, detected by semi-quantitative RT-PCR and MSP, but expressed and unmethylated in immortalized but non-transformed normal epithelial cell lines (with names green underlined). M, methylated; U, unmethylated. (FIG. 2E) Abundant expression of TET2 and TET3 in TET1-downregulated tumor cell lines. Ca, carcinoma; NPC, nasopharyngeal carcinoma; ESCC, esophageal squamous cell carcinoma; CRC, colorectal cancer; RCC, renal cancer; NKTCL, nasal NK/T-cell lymphoma.

(FIG. 3A) Detection of TET1 methylation in multiple tumor cell lines and normal cell lines by BGS. (FIG. 3B) Treatment with Aza or combined with TSA (A+T) demethylated TET1 promoter in silenced cell lines of multiple tissue types. Expression and methylation changes were detected by semi-quantitative RT-PCR and MSP. (FIG. 3C) BGS analysis of TET1 promoter in cell lines with or without treatment. NPC, nasopharyngeal carcinoma; ESCC, esophageal squamous cell carcinoma; CRC, colorectal cancer; BrCa, breast cancer; RCC, renal cancer; Ca, carcinoma.

FIGS. 4A-4E Frequent methylation of TET1 in multiple primary tumors. TET1 promoter methylation in (FIG. 4A) multiple primary tumors and (FIG. 4B) nose swab samples from NPC patients, detected by MSP. (FIG. 4C) TET1 methylation is barely seen in normal tissues by MSP analysis. (FIG. 4D) Representative BGS analysis of TET1 promoter methylation in primary tumors and normal tissues. Circles, CpG sites analyzed; row of circles, an individual promoter allele that was cloned, randomly selected and sequenced; filled circle, methylated CpG site; open circle, unmethylated site. (FIG. 4E) Levels of TET1 mRNA expression in representative paired tumor (T)/normal (N) tissues, and primary tumor tissues (NPC), measured by semi-quantitative RT-PCR. Ca, carcinoma; NPC, nasopharyngeal carcinoma; CRC, colorectal cancer; RCC, renal cancer; GsCa, gastric cancer; Sk. muscle, skeleton muscle; S. intestine, small intestine.

FIGS. 5A-5C Gene mutation analysis of TET1 in human cancers. Somatic mutations of TET1 gene in human cancers were analyzed using the COSMIC database. (FIG. 5A) Frequencies and (FIG. 5B) distributions of TET1 mutations. (FIG. 5C) Diagram displaying complete TET1 mutation spectrum identified and their distribution in the coding region of TET1.

(FIG. 6A) Structure and functional domains of the human TET1 protein, containing a C-terminal CD domain including the Cys-rich and DSBH regions, and a CXXC domain (SEQ ID NO:51). The positions of three nuclear localization sequences (NLS) are shown. TET1 catalytic domain (TET1-CD) containing the Cys-rich and DSBH regions and TET1 mutant (TET1-CD-mut) with two amino acid substitutions (H1672A; D1674A) in the catalytic domain are also shown. (FIG. 6B) Ectopic expression of TET1-CD inhibited tumor cell growth of multiple tissue types. Representative colony formation assays of TET1-CD- and TET1-CD-mut-expressing tumor cells of nasopharyngeal, esophageal, gastric, colon, and breast cancers are shown. Quantitative analyses of colony numbers are shown as values of mean±S.D. (lower panel), ***p<0.001. NPC, nasopharyngeal carcinoma; ESCC, esophageal squamous cell carcinoma; GsCa, gastric cancer; CRC, colorectal cancer; BrCa, breast cancer. (FIG. 6C) Ectopic expression of TET1-CD induced tumor cell apoptosis. TET1-CD, TET1-CD-mut, and vector-expressing NPC tumor cells (HONE1) were analyzed by TUNEL assays. (FIG. 6D) TET1-CD upregulated multiple TSGs expression in tumor cells, as examined by semi-quantitative RT-PCR. (FIG. 6E) TET1-CD upregulated multiple TSGs expression as measured by qRT-PCR in NPC (HNE1) cells. Fold changes of TSGs expression in TET1-CD and TET1-CD-mut-transcfected cells were calculated by normalizing towards vector-expressing cells (set 1.0). GAPDH was used as an internal control. Data are shown as mean±SD of three independent experiments. *p<0.05; p<0.01; *p<0.001. (FIG. 6F) Detection of promoters methylation of HOXA9, SLIT2 and ZNF382 genes by MSP in TET1-CD and TET1-CD-mut-expressing tumor cells.

FIGS. 8A-8B TET1 methylation in other tumor cell lines. (FIG. 8A) TET2 and TET3 are readily expressed in multiple carcinoma, non-Hodgkin (NHL) and nasal NK/T-cell (NKTCL) lymphoma cell lines except for two, detected by semi-quantitative RT-PCR with same cDNA samples as used in FIG. 2. (FIG. 8B) Examination of TET1 expression and methylation in hepatocellular, bladder, prostate cancer cell lines, and melanoma cell lines. Ca, carcinoma; NPC, nasopharyngeal carcinoma; ESCC, esophageal squamous cell carcinoma; CRC, colorectal cancer; HCC, hepatocellular carcinoma; CxCa, cervical cancer; RCC, renal cancer.

(FIGS. 11A, 11B) TET1 deletion was examined by multiplex differential genomic DNA-PCR using primers targeting two regions spanning exon 2 or exon 4, with GAPDH as an internal control. TET1 expression and methylation status in each sample is shown in bottom panels. Red-colored cell lines are considered as with hemizygous deletions. +, expressed; d, downregulated or silenced; M, methylated; U, unmethylated. (FIG. 11C) Alterations of TET1 DNA copy number in human cancers, analyzed using the Oncomine database. NPC, nasopharyngeal carcinoma; ESCC, esophageal squamous cell carcinoma; GsCa, gastric cancer; CRC, colorectal cancer; BrCa, breast cancer; CxCa, cervical cancer; RCC, renal cancer; NHL, non-Hodgkin lymphoma; HL, Hodgkin lymphoma; NKTCL, nasal NK/T-cell lymphoma; HNSCC, head and neck squamous cell carcinoma; HCC, hepatocellular carcinoma; Ca, carcinoma.

DEFINITIONS

Figure 1A:
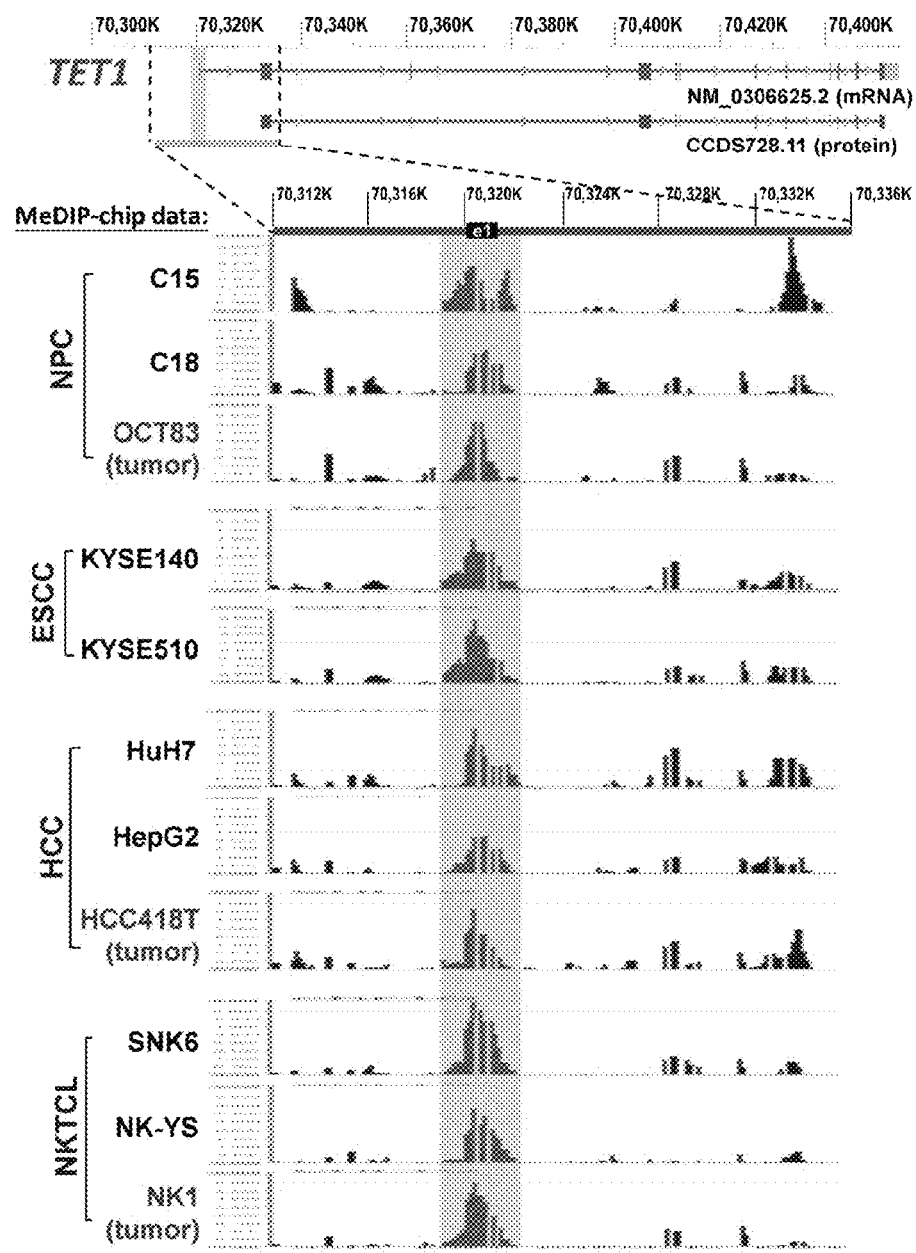
FIGS. 1A-1B CpG methylome study identified TET1 as a methylated target in multiple cancers.

The term "TET1 gene," as used herein, refers to any naturally occurring variants or mutants, interspecies homologs or orthologs, or man-made variants of human TET1 gene. The DNA sequence for a human wild-type TET1 mRNA is set forth in GenBank Accession No. NM_030625.2 (provided herein as SEQ ID NO:3), which translate to a coding sequence (provided herein as SEQ ID NO:4) for a 2136-amino acid TET1 protein (set forth in GenBank Accession No. NP_085128.2, provided herein as SEQ ID NO:5), wherein the catalytic domain of TET1 is the 1418 to 2136 fragment of SEQ ID NO:5, the actual sequence set forth in SEQ ID NO:6. A TET1 protein within the meaning of this application typically has at least 80%, or 90%, or 95% or higher sequence identity to the human wild-type TET1 protein (e.g., SEQ ID NO:5).

In this disclosure the term "or" is generally employed in its sense including "and/or" unless the content clearly dictates otherwise.

As used herein, the term "gene expression" is used to refer to the transcription of a DNA to form an RNA molecule encoding a particular protein (e.g., human TET1 protein) or the translation of a protein encoded by a polynucleotide sequence. In other words, both mRNA level and protein level encoded by a gene of interest (e.g., human TET1 gene) are encompassed by the term "gene expression level" in this disclosure.

In this disclosure the term "biological sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, white blood cells, all blood cells, and the like), sputum or saliva, lymph and tongue tissue, cultured cells, e.g., primary cultures, explants, and transformed cells, stool, urine, or tumor biopsy tissue etc. A biological sample is typically obtained from a eukaryotic organism, which may be a mammal, may be a primate and may be a human subject.

In this disclosure the term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, prostate, kidney, bladder, lymph node, liver, bone marrow, blood cells, etc.) among other factors. Representative biopsy techniques include, but are not limited to, excisional biopsy, incisional biopsy, needle biopsy, surgical biopsy, and bone marrow biopsy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form.

Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a variant TET1 protein such as its catalytic domain used in the method of this invention (e.g., for treating cervical cancer) has at least 80% sequence identity, preferably 85%, 90%, 91%, 92%, 93, 94%, 95%, 96%, 97%, 98%, 99%, or 100% identity, to a reference sequence, e.g., a wild-type human TET1 protein catalytic domain), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25:3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that reacts differentially with methylated and unmethylated DNA in a process through which distinguishable products or quantitatively distinguishable results (e.g. degree of binding or precipitation) are generated from methylated and non-methylated DNA, thereby allowing the identification of the DNA methylation status. Such processes may include, but are not limited to, chemical reactions (such as an unmethylated C→U conversion by bisulfite), enzymatic treatment (such as cleavage by a methylation-dependent endonuclease), binding, and precipitation. Thus, an enzyme that preferentially cleaves methylated DNA is one capable of cleaving a DNA molecule at a much higher efficiency when the DNA is methylated, whereas an enzyme that preferentially cleaves unmethylated DNA exhibits a significantly higher efficiency when the DNA is not methylated. In the context of the present invention, a reagent that "differentially modifies" methylated and unmethylated DNA also refers to any reagent that exhibits differential ability in its binding to DNA sequences or precipitation of DNA sequences depending on their methylation status. One class of such reagents consists of methylated DNA binding proteins.

A "CpG-containing genomic sequence" as used herein refers to a segment of DNA sequence at a defined location in the genome of an individual. Typically, a "CpG-containing genomic sequence" is at least 15 contiguous nucleotides in length and contains at least one CpG pair. In some cases, it can be at least 18, 20, 25, 30, 50, 80, 100, 150, 180, 200, 250, 300, 350, or 380 contiguous nucleotides in length and contains at least 2, 3, 4, 5, 6, 7, 8, 9, 10, 15, 20, 25, 30, or 35 CpG pairs. For any one "CpG-containing genomic sequence" at a given location, e.g., within a region of the human TET1 genomic sequence (such as the region containing the promoter and exon 1, e.g., sequence segments shown in FIG. 2A), nucleotide sequence variations may exist from individual to individual and from allele to allele even for the same individual. Furthermore, a "CpG-containing genomic sequence" may encompass a nucleotide sequence transcribed or not transcribed for protein production, and the nucleotide sequence can be a protein-coding sequence, a non protein-coding sequence (such as a transcription promoter), or a combination thereof.

As used in this application, an "increase" or a "decrease" refers to a detectable positive or negative change in quantity from a comparison control, e.g., an established standard control (such as an average expression level of TET1 mRNA or TET1 protein or an average number of methylated CpGs in a given genomic sequence of TET1 found in non-cancerous tissue). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for human TET1 or a portion thereof. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table 1 of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

"Standard control" as used herein refers to a predetermined amount or concentration of a polynucleotide sequence or polypeptide, e.g., TET1 mRNA or protein, or a predetermined level of DNA methylation in TET1 gene, that is present in an established normal disease-free tissue sample, e.g., a normal epithelial tissue sample. The standard control value is suitable for the use of a method of the present invention, to serve as a basis for comparing the amount of TET1 mRNA or protein or methylation level of TET1 genomic sequence that is present in a test sample. An established sample serving as a standard control provides an average amount of TET1 mRNA or TET1 protein or average level of TET1 genomic sequence methylation that is typical for a tissue sample, such as blood or epithelial tissue sample (e.g., an oral or nasal swab) of an average, healthy human without any tumor especially cancer as conventionally defined. A standard control value may vary depending on the nature of the sample as well as other factors such as the gender, age, ethnicity of the subjects based on whom such a control value is established.

The term "average," as used in the context of describing a human who is healthy, free of any type of cancer as conventionally defined, refers to certain characteristics, especially the amount of human TET1 mRNA or protein or the level of methylation in the TET1 genomic sequence, found in the person's tissue, e.g., epithelial tissue or mucosa, that are representative of a randomly selected group of healthy humans who are free of any malignant diseases (especially cancer). This selected group should comprise a sufficient number of humans such that the average amount of TET1 mRNA or protein or TET1 genomic sequence methylation level in the type of tissue among these individuals reflects, with reasonable accuracy, the corresponding amount of TET1 mRNA/protein or TET1 genomic methylation level in the general population of healthy humans. In addition, the selected group of humans generally have a similar age to that of a subject whose tissue sample is tested for indication of cancer. Moreover, other factors such as gender, ethnicity, medical history are also considered and preferably closely matching between the profiles of the test subject and the selected group of individuals establishing the "average" value.

The term "amount" as used in this application refers to the quantity of a polynucleotide of interest or a polypeptide of interest, e.g., human TET1 mRNA or TET1 protein, or the level of methylation in a predetermined genomic region of the TET1 gene, present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an polynucleotide encoding TET1 catalytic domain is the amount of said polynucleotide to achieve an increased level of TET1 protein biological activity, such that the symptoms of cancer are reduced, reversed, eliminated, prevented, or delayed of the onset in a patient who has been given the polynucleotide for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, cancer. Subjects also include individuals currently undergoing therapy that seek manipulation of the therapeutic regimen. Subjects or individuals in need of treatment include those that demonstrate symptoms of cancer or are at risk of suffering from cancer or its symptoms. For example, a subject in need of treatment includes individuals with a genetic predisposition or family history for cancer, those that have suffered relevant symptoms in the past, those that have been exposed to a triggering substance or event, as well as those suffering from chronic or acute symptoms of the condition. A "subject in need of treatment" may be at any age of life.

"Inhibitors," "activators," and "modulators" of TET1 protein are used to refer to inhibitory, activating, or modulating molecules, respectively, identified using in vitro and in vivo assays for TET1 protein binding or signaling, e.g., ligands, agonists, antagonists, and their homologs and mimetics. The term "modulator" includes inhibitors and activators. Inhibitors are agents that, e.g., partially or totally block carbohydrate binding, decrease, prevent, delay activation, inactivate, desensitize, or down regulate the activity of TET1 protein. In some cases, the inhibitor directly or indirectly binds to TET1 protein, such as a neutralizing antibody. Inhibitors, as used herein, are synonymous with inactivators and antagonists. Activators are agents that, e.g., stimulate, increase, facilitate, enhance activation, sensitize or up regulate the activity of TET1 protein. One example of TET1 activator is the catalytic domain of the TET1 protein (e.g., a polypeptide having the amino acid sequence set forth in SEQ ID NO:6). Modulators include TET1 protein ligands or binding partners, including modifications of naturally-occurring ligands and synthetically-designed ligands, antibodies and antibody fragments, antagonists, agonists, small molecules including carbohydrate-containing molecules, siRNAs, RNA aptamers, and the like.

DETAILED DESCRIPTION OF THE INVENTION

I. Introduction

The present inventors discovered for the first time that expression of TET1, both at the mRNA and protein levels, is suppressed in multiple types of cancer cells (nasopharyngeal carcinoma, esophageal squamous carcinoma, cervical cancer, renal cancer and lymphomas) due to hypermethylation in TET1 genomic sequence. This suppressed expression of TET1 protein is due to increased or higher than normal level of methylation in the TET1 promoter region, which leads to decreased transcription of TET1 mRNA. This discovery provides important means for detecting, monitoring, and treating a variety of cancers. Generally, a lower than normal TET1 mRNA/protein level seen in a test subject, who may or may not exhibit any signs of tumor or cancer, indicates a high likelihood that the subject already has or will later develop cancer, especially in the corresponding tissue/organ. Similarly, a higher than normal level of methylation in the TET1 promoter sequence, indicates a high likelihood that the subject already has or will later develop cancer, especially in the corresponding tissue/organ type (e.g., a higher risk of nasopharyngeal cancer is determined in a patient when higher level of TET1 methylation is detected in the patient's nasopharyngeal tissue sample).

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human TET1 gene, and synthetic oligonucleotides (e.g., primers) can be verified using, e.g., the chain termination method for sequencing double-stranded templates of Wallace et al., *Gene* 16:21-26 (1981).

III. Acquisition of Tissue Samples and Analysis of TET1 mRNA or DNA

The present invention relates to measuring the amount of TET1 mRNA or analyzing the methylation pattern of TET1 genomic DNA found in a person's tissue sample as a means to detect the presence, to assess the risk of developing, and/or to monitor the progression or treatment efficacy of a variety of cancers, depending on the type of tissue sample analyzed. Thus, the first steps of practicing this invention are to obtain a tissue sample from a test subject and extract mRNA or DNA from the sample, with the tissue sample generally corresponding to the organ/tissue for which cancer status is to be assessed (e.g., a nasopharyngeal tissue sample is analyzed to assess for the presence or risk of nasopharyngeal cancer in an individual, or a blood sample is analyzed to assess for the presence of risk of cancers of the blood cells, such as leukemia or lymphoma).

A. Acquisition and Preparation of Tissue Samples

A tissue sample is obtained from a person to be tested or monitored for cancer using a method of the present invention. Collection of various types of tissue sample, e.g., epithelial tissue sample, from an individual is performed in accordance with the standard protocol hospitals or clinics generally follow, such as during an endoscopy. An appropriate amount of tissue sample is collected from a chosen organ or anatomic site and may be stored according to standard procedures prior to further preparation.

The analysis of TET1 mRNA or DNA found in a patient's tissue sample according to the present invention may be performed using routine methodologies. The methods for preparing tissue samples for nucleic acid extraction are well known among those of skill in the art. For example, a subject's mucosa tissue sample should be first treated to disrupt cellular membrane so as to release nucleic acids contained within the cells.

B. Extraction and Quantitation of RNA

There are numerous methods for extracting mRNA from a biological sample. The general methods of mRNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of mRNA Level

Once mRNA is extracted from a sample, the amount of human TET1 mRNA may be quantified. The preferred method for determining the mRNA level is an amplification-based method, e.g., by polymerase chain reaction (PCR), especially reverse transcription-polymerase chain reaction (RT-PCR).

Prior to the amplification step, a DNA copy (cDNA) of the human TET1 mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention. One of skill in the art will recognize, however, that amplification of an mRNA species in a tissue sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA in a sample. For a review of branched- DNA signal amplification for direct quantitation of nucleic acid sequences in clinical samples, see Nolte, *Adv. Clin. Chem.* 33:201-235, 1998.

2. Other Quantitative Methods

The TET1 mRNA can also be detected using other standard techniques, well known to those of skill in the art. Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well-known techniques (see, e.g., Sambrook and Russell, supra), the presence of a band of the same size as the standard comparison is an indication of the presence of a target mRNA, the amount of which may then be compared to the control based on the intensity of the band. Alternatively, oligonucleotide probes specific to TET1 mRNA can be used to detect the presence of such mRNA species and indicate the amount of mRNA in comparison to the standard comparison, based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^{3}$H, $^{125}$I, $^{35}$S, $^{14}$C, or $^{32}$P, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255:137-149, 1983.

C. Detection of Methylation in TET1 Genomic Sequence

Methylation status of a segment of TET1 genomic sequence containing one or more CpG (cytosine-guanine dinucleotide) pairs is investigated to provide indication as to whether a test subject is suffering from cancer, whether the subject is at risk of developing cancer, or whether the subject's cancer is worsening or improving/cancer risk is increasing or decreasing.

Typically a segment of the TET1 genomic sequence that includes the 5' untranslated region (such as the promoter region) and includes one or more CpG nucleotide pairs is analyzed for methylation pattern. For example, SEQ ID NO:1 or a portion thereof (e.g., SEQ ID NO:2) can be used to determine how many of the CpG pairs within the sequence are methylated and how many are not methylated. The sequence being analyzed should be long enough to contain at least 1 CpG dinucleotide pair and detection of methylation at this CpG site is typically adequate indication of the presence of cancer cells. The length of the sequence being analyzed is usually at least 15 or 20 contiguous nucleotides, and may be longer with at least 25, 30, 50, 75, 100, 150, 170, 180, or up to 200 contiguous nucleotides. At least one, typically 2 or more, often 3, 4, 5, 6, 7, 8, 9, 10, 20, 25, 30, 50 or more, CpG nucleotide pairs are present within the sequence. In the cases of multiple (2 or more) CpG sites are analyzed for methylation status (which may be 100% methylated or at least 50% methylated), when at least 50% of the CpG pairs within the analyzed genomic sequence are shown to be methylated, subject being tested is deemed to have cancer or have an elevated risk of developing cancer. As an example, SEQ ID NO:1 (+151 to +534 in relation to the transcription start site) and SEQ ID NO:2 (+221 to +393 in relation to the transcription start site, a portion of SEQ ID NO:1) are TET1 genomic sequence segments that can be chosen as target sequences for the analysis. Some or majority of the CpG pairs in this region are found to be methylated in established cancer cell lines and samples taken from cancerous tissue, whereas non-cancerous cells showed very few, if any at all, methylated CpG sites (see, e.g., FIG. 2). For example, the presence of cancer or an increased risk for later developing cancer is established when at least 90% (or at least 36 CpG sites) of the 39 CpG sites within the region are found to be at least 50% methylated or when at least 50% (or at least 20 CpG sites) of the 39 CpG sites are found to be 100% methylated. For the purpose of determining the methylation pattern of a TET1 genomic sequence, bisulfite treatment followed by DNA sequencing is particularly useful, since bisulfite converts an unmethylated cytosine (C) to a uracil (U) while leaving methylated cytosines unchanged, allowing immediate identification through a DNA sequencing process. Optionally, an amplification process such as PCR is included after the bisulfite conversion and before the DNA sequencing.

1. DNA Extraction and Treatment

Methods for extracting DNA from a biological sample are well known and routinely practiced in the art of molecular biology, see, e.g., Sambrook and Russell, supra. RNA contamination should be eliminated to avoid interference with DNA analysis. The DNA is then treated with a reagent capable of modifying DNA in a methylation differential manner, i.e., different and distinguishable chemical structures will result from a methylated cytosine (C) residue and an unmethylated C residue following the treatment. Typically, such a reagent reacts with the unmethylated C residue(s) in a DNA molecule and converts each unmethylated C residue to a uracil (U) residue, whereas the methylated C residues remain unchanged. This unmethylated C→U conversion allows detection and comparison of methylation status based on changes in the primary sequence of the nucleic acid. An exemplary reagent suitable for this purpose is bisulfite, such as sodium bisulfite. Methods for using bisulfite for chemical modification of DNA are well known in the art (see, e.g., Herman et al., *Proc. Natl. Acad. Sci. USA* 93:9821-9826, 1996).

As a skilled artisan will recognize, any other reagents that are unnamed here but have the same property of chemically (or through any other mechanism) modifying methylated and unmethylated DNA differentially can be used for practicing the present invention. methods for detecting DNA methylation include, for example, methylation-specific PCR (MSP), methylation-sensitive single nucleotide primer extension (Ms-SnuPE), high resolution melting (HRM) analysis, bisulifte sequencing, pyrosequencing, methylation-specific melting curve analysis (MS-MCA), methylation-specific denaturing high-performance liquid chromatography (MS-DHPLC), methylation-specific microarray (MSO). These assays can be either PCR analysis, quantitative analysis with fluorescence labelling or Southern blot analysis.

2. Optional Amplification and Sequence Analysis

Following the modification of DNA in a methylation-differential manner, the treated DNA is then subjected to sequence-based analysis, such that the methylation status of the TET1 genomic sequence may be determined. An amplification reaction is optional prior to the sequence analysis after methylation specific modification. A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

Although PCR amplification is typically used in practicing the present invention, one of skill in the art will recognize that amplification of the relevant genomic sequence may be accomplished by any known method, such as the ligase chain reaction (LCR), transcription-mediated amplification, and self-sustained sequence replication or nucleic acid sequence-based amplification (NASBA), each of which provides sufficient amplification.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes (e.g., C→U) in a polynucleotide sequence for practicing the methods of the present invention include but are not limited to mass spectrometry, primer extension, polynucleotide hybridization, real-time PCR, melting curve analysis, high resolution melting analysis, heteroduplex analysis, pyrosequencing, and electrophoresis.

IV. Establishing a Standard Control

In order to establish a standard control for practicing the method of this invention, a group of healthy persons free of any tumor especially any form of cancer as conventionally defined is first selected. These individuals are within the appropriate parameters, if applicable, for the purpose of screening for and/or monitoring cancer using the methods of the present invention. Optionally, the individuals are of same gender, similar age, or similar ethnic background.

The healthy status of the selected individuals is confirmed by well established, routinely employed methods including but not limited to general physical examination of the individuals and general review of their medical history.

Furthermore, the selected group of healthy individuals must be of a reasonable size, such that the average amount/concentration of human TET1 mRNA or TET1 protein or average level of TET1 methylation in the tissue sample obtained from the group can be reasonably regarded as representative of the normal or average level among the general population of healthy people. Preferably, the selected group comprises at least 10 human subjects.

Once an average value for the TET1 mRNA or protein or average level of TET1 methylation (e.g., a certain number of methylated CpG islands within a pre-determined segment of TET1 genomic sequence) is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gender, or ethnic background.

V. Treatment and Prevention of Cancer

By illustrating the correlation of suppressed expression of TET1 protein and cancer, the present invention further provides a means for treating patients suffering from cancer: by way of increasing TET1 protein expression or biological activity, for example, by overexpression of TET1 protein's catalytic domain. As used herein, treatment of cancer encompasses reducing, reversing, lessening, or eliminating one or more of the symptoms of cancer, as well as preventing or delaying the onset of one or more of the relevant symptoms.

Upon detecting suppressed expression of TET1 at mRNA/protein level cue to increased methylation level of TET1, especially at the promoter/exon 1 region (e.g., SEQ ID NO:1 or 2), one may establish the presence of cancer in a patient or an increased risk of later developing the disease in the patient. As a result of this determination, the patient may be subject to subsequent therapies or preventive/monitoring measures, especially those fitting certain profiles, such as those with a family history of cancer, such that the symptoms of cancer may be prevented, eliminated, ameliorated, reduced in severity and/or frequency, or delayed in their onset. For example, a physician may prescribe both pharmacological and non-pharmacological treatments such as lifestyle modification (e.g., reduce body weight by 5% or more, assume a healthier life style including following a high fibre diet and maintaining a higher level of physical activities such as walking for at least 150 minutes weekly, and undergo routine screening/examination such as regular colonoscopy every 5 years). In some cases, when the presence of cancer is confirmed by way of other diagnostic means (e.g., biopsy of the relevant tissue), aggressive treatment may be used such as surgical intervention as well as radio- and/or chemo-therapy.

VI. Kits and Devices

The invention provides compositions and kits for practicing the methods described herein to assess the level of methylation in TET1 genomic DNA (e.g., in the segment of genomic sequence set forth in SEQ ID NO:1 or 2) in a subject, which can be used for various purposes such as detecting or diagnosing the presence of various forms of cancer, determining the risk of developing the cancer, and monitoring the progression of the cancer in a patient, including assessing the likelihood of mortality from the cancer.

Kits for carrying out assays for determining TET1 gene methylation level typically include an agent that can differentially modify methylated and unmethylated DNA (such as a bisulfite), a pair of oligonucleotide primers useful for specific hybridization with at least one segment of the TET1 coding sequence or its complementary sequence so as to allow amplification of a genomic sequence segment comprising at least 5 CpGs, e.g., SEQ ID NO:1 or 2 (the +151 to +534 segment or the +221 to +393 segment). Optionally, an oligonucleotide probe is included in the kit. This oligonulcoetide probe is labeled with a detectable moiety and specifically hybridizes to the polynucleotide sequence corresponding to the methylated version of the genomic sequence or the unmethylated version following treatment by the agent that differentially modifies methylated and unmethylated DNA. In some cases, the kits may include at least two or possibly more different oligonucleotide probes that each specifically hybridizes to a methylated or unmethylated version of TET1 genomic sequence after treatment by the agent differentially modifying methylated and unmethylated DNA, particularly after amplification such as by PCR. In addition, the kits of this invention may provide instruction manuals to guide users in analyzing test samples and assessing the presence, risk, or state of cancer in a test subject.

In a further aspect, the present invention can also be embodied in a device or a system comprising one or more such devices, which is capable of carrying out all or some of the method steps described herein. For instance, in some cases, the device or system performs the following steps upon receiving a tissue sample, e.g., a mucosa tissue sample or blood sample taken from a subject being tested for detecting cancer or a blood malignancy, assessing the risk of developing a cancer of epithelium or blood in origin, or monitored for progression of the condition: (a) determining in sample the level of TET1 genomic sequence methylation (which may be measured by the number of CpGs in a pre-determined genomic region, e.g., SEQ ID NO:1 or 2, that are at least 50% methylated or at least 90% methylated; (b) comparing the level with a standard control value; and (c) providing an output indicating whether cancer is present in the subject or whether the subject is at risk of developing cancer, or whether there is a change, i.e., worsening or improvement, in the subject's cancer condition. In other cases, the device or system of the invention performs the task of steps (b) and (c), after step (a) has been performed and the amount or concentration from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Introduction

DNA methylation at the C5 position of cytosine (5-methylcytosine, 5-mC), known as the "fifth base," is a key epigenetic modification at CpG dinucleotides, playing critical roles in normal development and disease pathogenesis including tumorigenesis[1]. Regional promoter CpG methylation together with genome-wide hypomethylation, as a fundamental epigenetic hallmark of cancers, lead to the silencing of tumor suppressor genes (TSG) and activation of oncogenes, contributing to cancer initiation and progression. Recently, various whole-genome sequencing studies of virtually all human cancers also demonstrate that the most commonly mutated genes are epigenetic modifiers including CpG methylation machinery components across diverse cancers[2-5], highlighting the direct and crucial involvement of epigenetic programming dysregulation in tumorigenesis.

DNA methylation is a reversible process, through either passive or active demethylation. Passive demethylation has been well-documented owing to reduction in activities or absence of DNA methyltransferases (DNMTs) during DNA replication. The newly identified 5-hydroxymethylcytosine (5hmC) in mammalian genomic DNA[6], as an intermediate of active DNA demethylation, has been recognized as the "sixth base," which provides us new insight into the regulation of CpG methylation dynamics via active demethylation. 5hmC is readily expressed in human normal tissues and embryonic stem cells, but becomes greatly decreased in multiple cancer tissues[7-9]. 5hmC modification is relatively stable, not just as a transient intermediate[10], arising as a novel epigenetic hallmark of tumors[11].

The ten-eleven translocation (TET) family of DNA hydroxylases, including TET1, TET2, and TET3, mediates the initial conversion of 5mC to 5hmC and final DNA demethylation through sequential oxidation reactions, thus as key executers for establishing 5hmC pattern and maintaining a hypomethylated genome state[12,13]. TET1 was firstly identified as a fusion partner of MLL in acute myeloid leukemia (AML)[6]. Inactive mutations or deletions of TET2 with impaired catalytic activity were frequently detected in hematopoietic malignancies[14], along with decreased 5hmC levels[4,15,16], while no somatic TET1 or TET3 mutation was found in myeloid and lymphoid tumors. The biological functions of TET family members or 5hmC on the reprogramming and development of embryotic stem cells have been extensively studied[17-21]. Recent reports also demonstrate that TET gene expression are reduced in some solid tumors, associated with 5hmC depletion and gene downregulation, thus playing critical functional roles in tumor initiation and metastasis[22-26]. Some mechanisms have been proposed to mediate TET disruption in cancers, including post-transcriptional regulation by miR-22[27], post-translational modification by cellular proteolytic system[28], and nuclear exclusion of TET proteins[29,30]. However, a systematic study of the expression and transcriptional regulation of TET members in most human cancers is still needed.

Here, the present inventors have studied the expression and transcriptional regulation of TET family genes in a large collection of human normal and tumor samples. They examined the epigenetic and genetic alterations of TET1 through analyzing cancer methylomes previously established by the inventors[31] and also online genomics database of common tumors. Frequent promoter methylation of TET1 was discovered in a large set of tumor cell lines and primary tumors, confirming its tumor suppressive functions and demethylation activity in tumor cells.

Results and Discussion

Epigenomic Identification of TET1 as a Methylated Target in Multiple Cancers

During the analysis of whole-genome CpG methylation profiles (methylomes) of multiple tumor cell lines and primary tumors[31], the promoter of one of the CpG demethylases, TET1, turned out to be a target in multiple methylomes (FIG. 1A). Bioinformatics analysis of the methylome data showed significant positive enrichment of CpG methylation (Cut off=2) at the TET1 promoter and exon 1 region in multiple tumors, including nasopharyngeal carcinoma (NPC) xenografts (C15, C18) and primary tumor (OCT83), esophageal squamous cell carcinoma (ESCC) cell lines (KYSE140, KYSE510), hepatocellular carcinoma (HCC) cell lines (HuH7, HepG2) and primary tumor (418T), as well as nasal NK/T-cell lymphoma (NKTCL) cell lines (SNK6, NK-YS) and primary tumor (NK1) (FIG. 1A). The TET1 promoter and exon 1 region contain a typical CpG island (FIG. 2A), indicating that CpG methylation most likely regulates its expression in human cells.

Figure 1B:
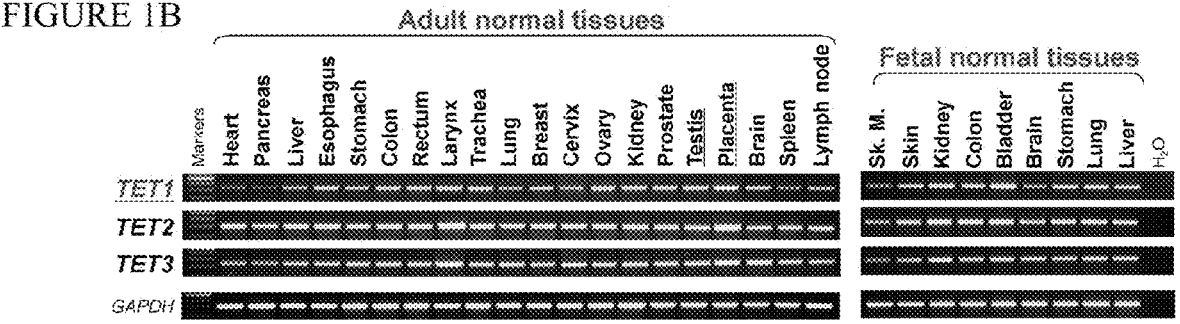

The expression and methylation profiles of TET1 was thus further examined in multiple cancers. Results showed that, although all three TET genes (TET1, -2, -3) were ubiquitously expressed in a series of human normal adult and fetal tissues (FIG. 1B), only TET1 neither TET2 nor TET3, was frequently downregulated or totally silenced in a variety of tumor cell lines including multiple carcinomas (nasopharyngeal, esophageal, lung, gastric, colon, breast, cervical, renal) and lymphomas (Hodgkin, non-Hodgkin and NKTCL), while TET1 is readily expressed in all immortalized normal epithelial cell lines of different tissue origins (FIG. 2).

Methylation-specific PCR (MSP) primers for TET1 was tested for not amplifying any not-bisulfited DNA, confirming the detection specificity of TET1 methylation in our study (FIG. 2B). Then by MSP, we detected TET1 promoter methylation in virtually all downregulated cell lines of nasopharyngeal, esophageal, lung, gastric, colon, breast, cervical and renal carcinomas, as well as Hodgkin (HL), non-Hodgkin (NHL) and NKTCL lymphomas, but not in immortalized normal epithelial cell lines (FIG. 2C, D; Table 1). Moreover, TET1 downregulation and methylation were infrequently detected in hepatocellular (HCC) and prostate cancer cell lines but not in the bladder and melanoma cell lines examined (FIG. 8B).

Figure 3A:
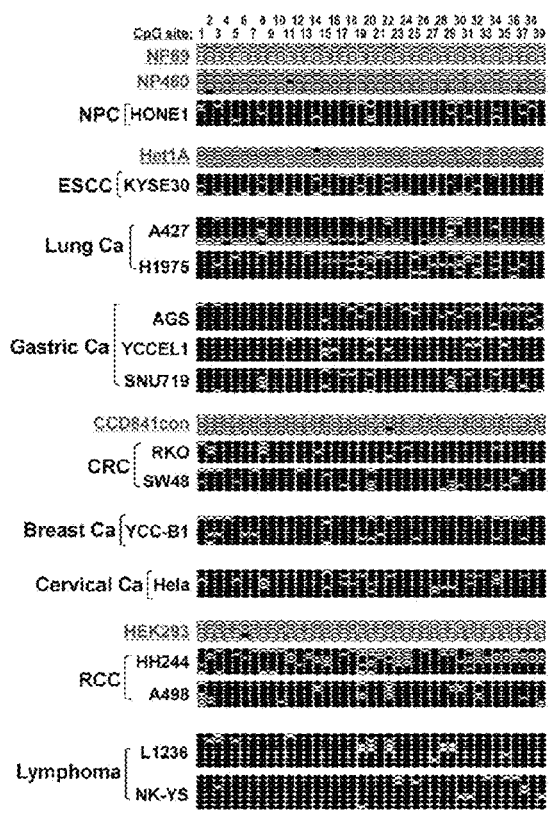
FIGS. 3A-3C Demethylation treatment could reactivate TET1 expression in silenced tumor cell lines.

The detailed methylation profile of TET1 promoter was further studied by bisulfate genomic sequencing (BGS). A 384-bp region (+151-bp to +534-bp) spanning TET1 promoter and exon 1, containing 39 CpG sites was analyzed (FIG. 2A). BGS results showed heavily methylated alleles in representative cell lines, including NPC, ESCC, lung, gastric, colon, breast, cervical and renal carcinomas, as well as lymphomas, while barely present in immortalized normal cell lines of nasopharyngeal (NP69, NP460), esophageal (Het-1A), colon (CCD841con) and kidney (HEK293) epithelial cells, consistent with the MSP data (FIG. 3A). Thus, TET1 silencing by promoter CpG methylation is a common event in multiple tumors.

Figure 3B:
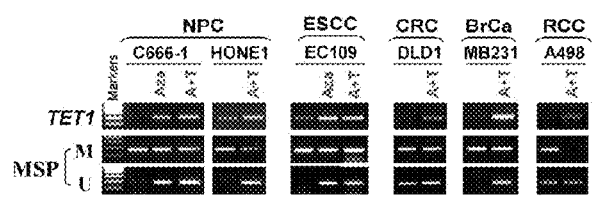
Figure 3C:
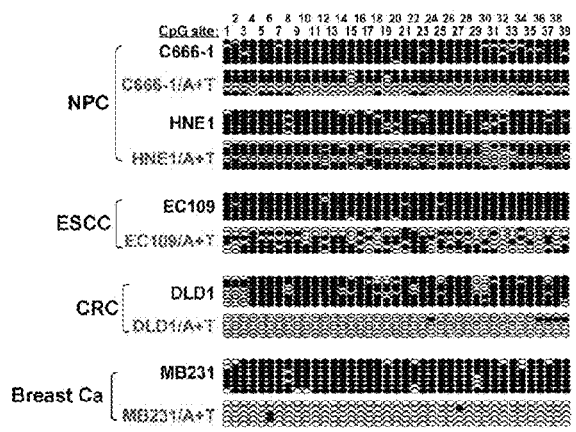

It was further investigated whether TET1 promoter methylation directly mediates its repression. DNA methyltransferase inhibitor 5-aza-dC (Aza) was used or in combination with histone deacetylase (HDAC) inhibitor to treat tumor cell lines of nasopharyngeal, esophageal, colon, breast and renal, all with methylated and downregulated TET1. After the treatment, restoration of TET1 expression was observed, along with increased unmethylated promoter alleles as detected by MSP (FIG. 3B). Demethylation of the TET1 promoter was confirmed by BGS analysis, which shows dramatically demethylated CpG sites (FIG. 3C), indicating that CpG methylation directly mediates TET1 silencing in tumor cells.

In this study, epigenetic silencing was demonstrated as a common regulatory mechanism for TET1 inactivation at the transcriptional level in multiple human cancers. Additional alternative mechanisms regulating expression and activities of TET family members have been reported[32]. For examples, high mobility group AT-hook 2 (HMGA2), a chromatin remodeling factor, suppresses TET1 expression by directly binding to its promoter or indirectly through other components in breast cancer cells[24]. Polycomb repressive complex 2 (PRC2) mediates Tet1 downregulation through H3K27me3 histone mark deposition[33]. PARP activity increases TET1 expression levels through maintaining a permissive chromatin state[34]. miR-22 suppresses TET expression levels in breast cancer cells through directly targeting the 3'-untranslated regions (UTRs) of TET mRNAs[27]. As direct substrates of calpains (calcium-activated cysteine proteases), TET proteins also undergo calpain-mediated degradation[28]. Nuclear exclusion of TET1 and TET2 is significantly correlated with loss of 5mC in glioma and colon cancer[29,30]. Thus, TET expression could be regulated at multiple levels of transcription, post-transcription or post-translation in different cell context, although TET1 silencing through promoter CpG methylation appears to be more common and predominant in multiple tumors.

Frequent Silencing of TET1 by Promoter Methylation in Primary Tumors

Figure 9:
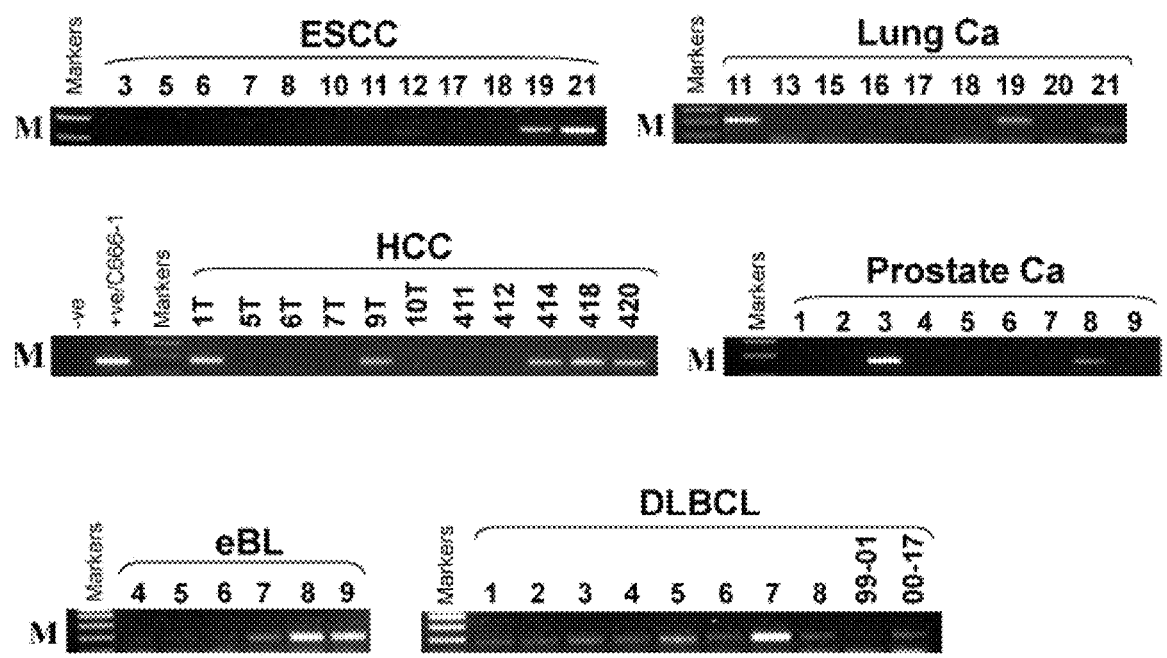
FIG. 9. Detection of TET1 methylation by MSP in primary tumors of esophageal (ESCC), lung, hepatocellular (HCC), prostate, endemic Burkitt lymphoma (eBL), and diffuse large B-cell lymphoma (DLBCL). Ca, carcinoma.
Figure 10A:
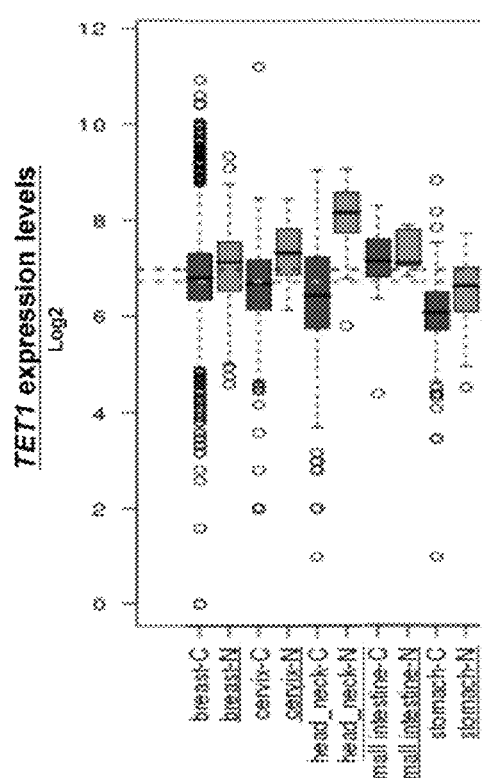
FIGS. 10A-10B TET1 expression was broadly reduced in multiple human cancers. Analysis of TET1 mRNA expression using (FIG. 10A) the GENT and (FIG. 10B) the Oncomine databases. TET1 was found to be significantly downregulated in different types of tumors, compared to normal controls. Ca, carcinoma; CRC, colon cancer; ccRCC, clear cell renal cell carcinoma; CxCa, cervical cancer; OvCa, ovarian cancer; CLL, chronic lymphocytic leukemia.
Figure 10B:
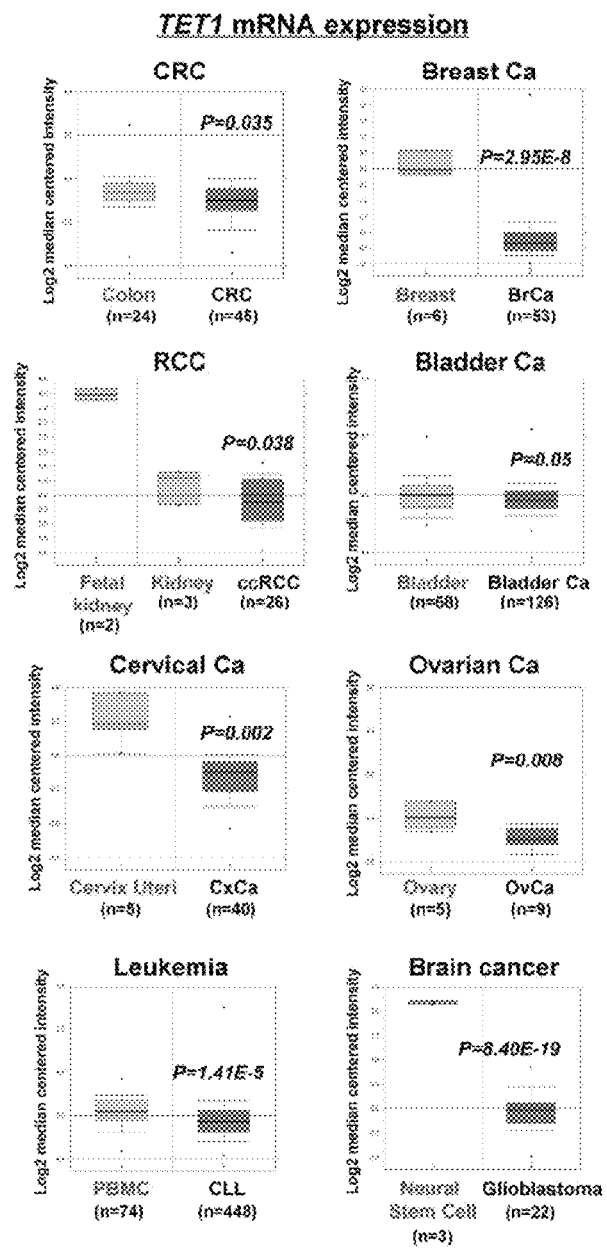

As promoter CpG methylation in tumor cell lines might be derived from cell culture-induced secondary effect, TET1 methylation and expression was further examined in primary tumor samples. Frequent TET1 methylation was detected in multiple tumors, including 55% (31/56) of NPC, 55% (30/55) of gastric, 27% (3/11) of colon, 42% (5/12) of hepatocellular, 36% (18/50) of breast and 28% (13/46) of renal tumor samples, as well as 78% of primary Hodgkin and 83% (10/12) of NKTCL lymphoma samples (FIG. 4A, FIG. 9, Table 1), but infrequently in primary ESCC, lung, prostate tumors and other non-Hodgkin lymphomas (FIG. 9, Table 1). TET1 methylation could even be detected in 50% of 16 nose swab samples from suspected NPC patients (FIG. 4B). In contrast, TET1 methylation was not detected in a panel of human normal adult and fetal tissues except for being barely seen in normal small intestine and colon (FIG. 4C). Further detailed BGS methylation analysis confirmed the presence of methylated promoter alleles in primary tumors but not normal tissues (FIG. 4D). TET1 downregulation was also detected in paired primary tumors of several tissue types (lung, stomach, colon, rectum, breast and kidney) and primary NPC tumors (FIG. 4E). Furthermore, through online GENT and Oncomine database analysis, we found that TET1 mRNA levels were significantly reduced in multiple solid tumors and leukemia, compared with their corresponding normal tissues (FIG. 10). These results clearly demonstrate that TET1 silencing by promoter CpG methylation is a common event for multiple tumors of epithelial and lymphoid origins.

Several studies have shown that TET genes are readily expressed in normal esophageal, gastric, colon, liver and breast tissues by PCR or immunohistochemistry[22,23,25], but decreased in tumor cell lines and primary tumors to varied grades, with TET1 as the most significantly downregulated member. A previous report through analyzing Cancer Genome Atlas TCGA database found that TET1 is downregulated in primary tumors of colorectal, breast and lung since early stage, and associated with patient poor survival[23]. TET1 is significantly decreased at mRNA and protein levels in gastric primary tumors compared to surgical margins and associated with tumor localization and TNM grades[35]. DNA methylation and bivalent histone marks at the CpG island 3'-shore mediate TET1 silencing in gastric cancer[36]. Reduced TET1 expression or 5hmC level in breast cancer tissues could be biomarkers for breast cancer progression[37]. TET1 methylation in colorectal cancer tissues, not TET2 and TET3[38], has been found as an early event in CRC tumorigenesis, thus as a valuable biomarker for metastasis prediction[39]. The results here are consistent with these previous studies. TET1 methylation appears to be tumor-specific and thus could serve as a potential epigenetic biomarker for cancer detection.

Genetic Alteration of TET1 is Uncommon in Human Cancers

Figure 11A:
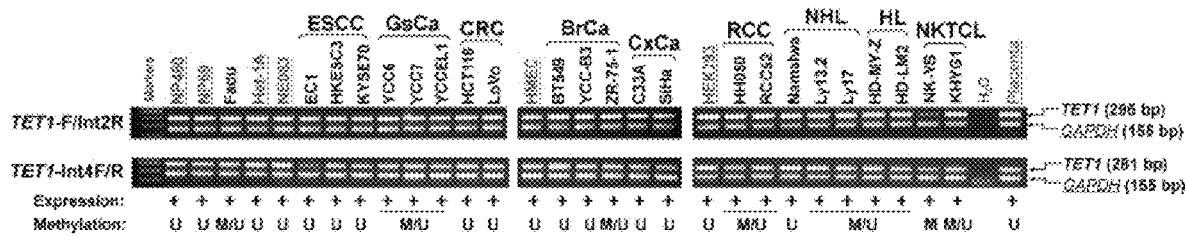
FIGS. 11A-11C Genetic deletion analysis of TET1 in multiple tumor cell lines.
Figure 11B:
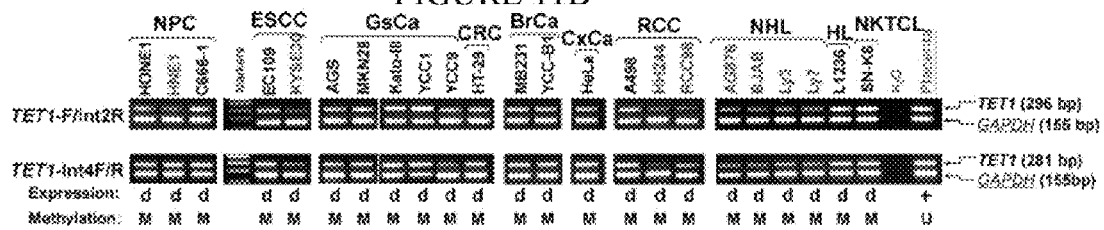
Figure 11C:
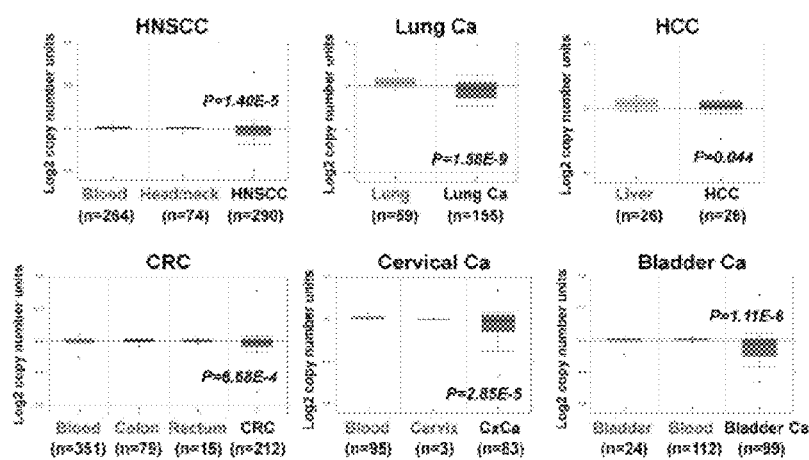

As alterations of cancer gene are through either genetic or epigenetic mechanisms, possible genetic alterations of TET1 were further investigated in cancers. Somatically acquired mutations of TET1 in human cancers were analyzed using the COSMIC database. Only <1% of tumor cases (most cases with ≤0.25%) had detectable TET1 mutations (FIG. 5A), consisting of 80% of missense mutations, 10% of nonsense and 10% of synonymous mutations (FIG. 5B), with most of the mutations located in coding regions (FIG. 5C). Hemizygous deletion of TET1 was also detected in some tumor cell lines with TET1 silencing and methylation, but not in TET1-expresssing cells (FIG. 11A, B). Consistently, TET1 gene deletion was also observed in solid tumors by analyzing DNA copy number alterations using the Oncomine database (FIG. 11C). These results demonstrate that TET1 mutation is uncommon in human cancers, although TET1 deletion is indeed present in some tumor samples.

TET1 Functions as a Tumor Suppressor Which Requires its Catalytic Activity

Figure 6A:
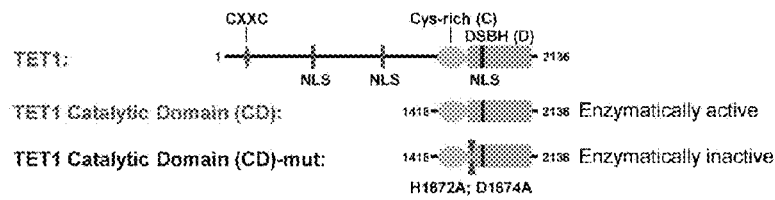
FIGS. 6A-6F TET1 functions as a tumor suppressor in multiple tumor cells.
Figure 6B:
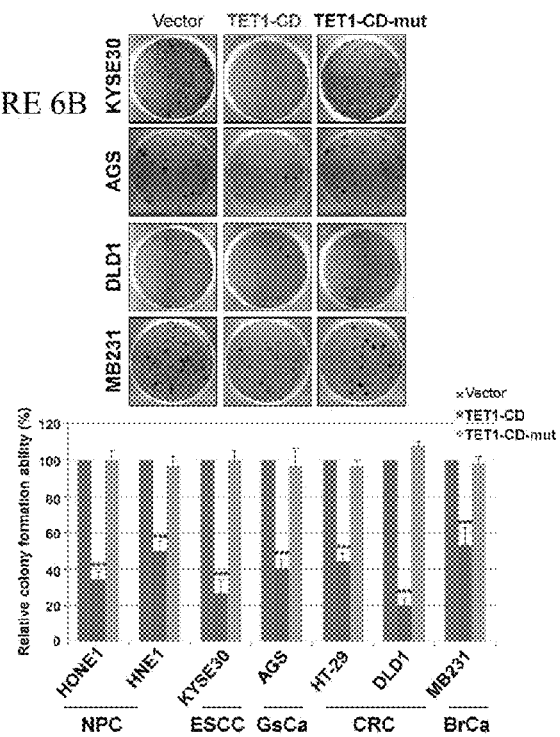
Figure 6D:
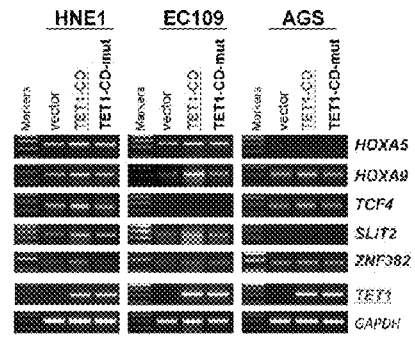
Figure 6E:
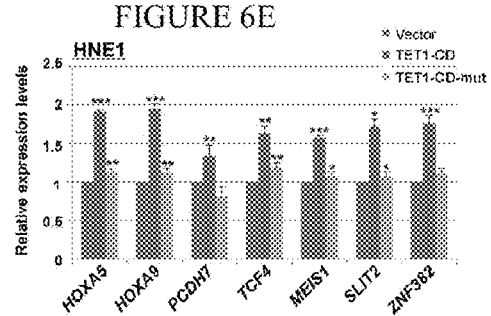
Figure 6C:
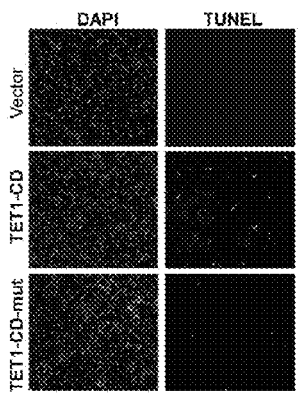

The TEM catalytic domain (CD) (containing the Cys-rich and DSBH regions) remains intact hydroxylase activity in embryonic development and reprogramming[6,13], displaying ability to induce 5hmC formation, demethylation and gene transcription in differentiated cells[33]. It was tested whether the catalytic activity of TET1 was required for its possible tumor suppression functions, using TET1-CD and its enzymatic dead mutant (TET1-CD-mut) (FIG. 6A). Ectopic expression of TET1-CD significantly suppressed tumor cell clonogenicity (to ~40-50% of control cells) in colony formation assays of NPC, ESCC, gastric, colon and breast tumor cells, while the TET1-CD-mut lost this ability (FIG. 6B). TUNEL assay showed significantly increased numbers of apoptotic cells in TET1-CD expressing-tumor cells, compared with vector or TET1-CD-mut controls (FIG. 6C). These results demonstrate that TET1 possesses bona fide tumor suppressive functions in tumor cells of multiple types.

Consistent with the above results, several recent studies have shown similar tumor-suppressive functions of TET1 in cancer cells. TET1 inhibits proliferation and invasion of colon[23], breast[24,25], renal[40] and prostate[25] cancer cells in vivo and in vitro. TET1 deficiency promotes B-lineage differentiation, leading eventually to B-cell lymphoma[41]. TET1 suppression as a key event of the RAS programming is required for KRAS-induced cellular transformation[26]. Thus, loss of function of TET1 is a common event during multiple tumorigenesis of solid tumors or hematologic malignancies.

TET1 Induces TSG Promoter Demethylation in Tumor Cells

Figure 6F:
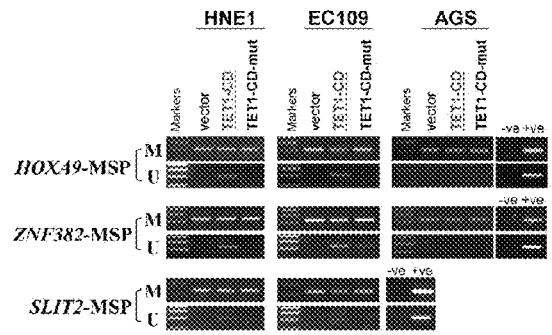

Several studies identified TET1 target genes in mouse ES cells and some tumor cells, using RNA- or ChIP-sequencing or hydroxymethylated DNA immunoprecipitation sequencing (hMeDIP-seq)[12,24,26,27,33,42-45]. A series of TET1-targeted genes including TSGs have been identified, such as TIMP[25], HOXA9 and HOXA7[24], and Wnt signaling antagonists DKK3 and DKK4[23]. To further explore the molecular mechanism of TET1 in tumor suppression, some known and potential target TSGs were examined to assess the demethylase activity of TET1 in tumor cells. Mild upregulation of HOXA9, HOXA5, PCDH7, TCF4, MEIS1, SLIT2 and ZNF382 at mRNA levels was observed in TET1-CD-expressing carcinoma cells by semi-quantitative RT-PCR (FIG. 6D) and qRT-PCR (FIG. 6E). Meanwhile, decreased methylated alleles of HOXA9, SLIT2 and ZNF382 promoters were also detected in TET1-CD-expressing tumor cells, but not in TET1-CD-mut-expressing cells, with increased unmethylated promoter alleles observed concurrently, suggesting that TET1 indeed functions as a CpG demethylase to demethylase and reactivate multiple TSGs in tumor cells (FIG. 6F). In addition to HOXA9, it was also found that TSGs like SLIT2, ZNF382, PCDH7, TCF4, MEIS1 and HOXA5 as TET1 target genes which could be demethylated and reactivated by TET1 in tumor cells. Other mechanisms besides demethylase activity could also be involved in regulating target genes by TET1, such as recruiting PRC2[42], PRDM14[43], Sin3A co-repressor complex[44] and MBD3/NURD complex[45]. Further studies on TET1-targeted gene regulation in human cancers would help better understand its role in cancer development.

Figure 7:
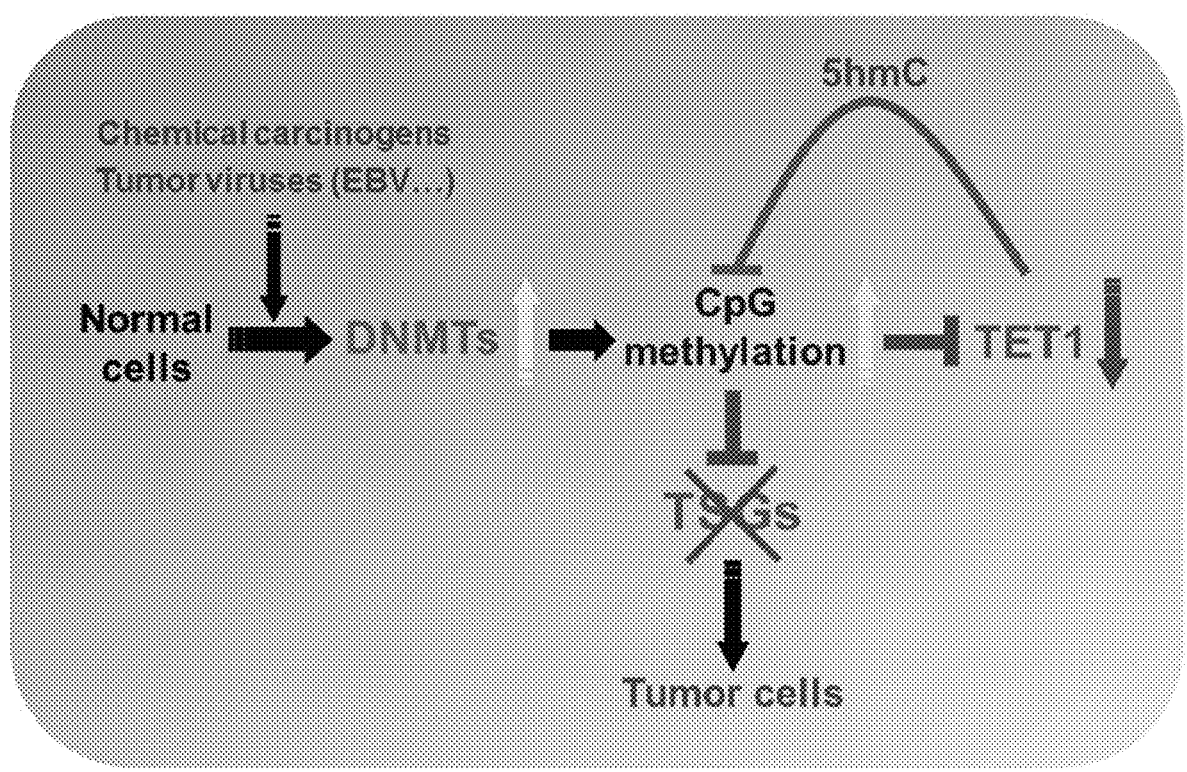
FIG. 7. Proposed model of a DNA methylation feedback loop mediated by DNMTs/CpG methylation and TET1 during human tumorigenesis. When normal cells are exposed to carcinogens (chemical carcinogens, tumor viruses, . . . etc), DNA methyltransferases (DNMTs) are induced, upregulated or overactivated, which further generates higher levels of DNA CpG methylation (5mC). Elevated level of 5mC on tumor suppressor gene (TSG) promoters lead to TSGs silencing and functional inactivation, ultimately to tumorigenesis. Ten-eleven-translocation (TET) proteins catalyze DNA CpG demethylation through converting 5mC to 5-hydroxymethylcytosine (5hmC), maintaining a delicate balance between CpG methylation and demethylation in normal cells. While in premalignant or tumor cells, CpG demethylation by TET would induce TSG promoter demethylation and functional restoration for further tumor suppression. Thus unlike normal cells where TET proteins are abundant, loss of TET1 expression through promoter CpG methylation frequently occurs in tumor cells, which in turn, increases 5mC levels and promotes TSG inactivation in tumor pathogenesis.

The discovery of TET enzymes, in addition to DNMTs, establishes a fundamental etiologic role of CpG methylation in human cancers. In response to environment carcinogens[46-48] like chemical carcinogens and tumor viruses, DNMT activities and expression levels are induced and increased in cells, displaying stronger maintenance and de novo methylation capacity, leading to specific gene CpG island hypermethylation. The epigenetic alterations, especially promoter CpG methylation of TSGs, facilitate genome instability, disrupted cellular signaling and even further genetic mutations, thus are crucial to tumor initiation and progression[1,49]. Remarkably, promoter CpG methylation-mediated silencing of the CpG demethylase TET1 in human cancers, which in turn, further leads to increased 5mC levels in tumor cells, thus forming a DNA methylation feedback loop mediated by DNMT/CpG methylation and TET1 (FIG. 7).

In summary, this study comprehensively examined TET1 expression and methylation status in multiple tumors, and demonstrated that promoter CpG methylation is a predominant mechanism for TET1 inactivation in human cancers. The tumor-specific methylation of TET1 could serve as a valuable, non-invasive epigenetic tumor biomarker. TET1 as a tumor suppressor and CpG demethylase in tumor cells requires its intact catalytic domain, which provides new insight into the epigenetic master role of TET1 in tumor pathogenesis. These findings provide the mechanistic elucidation of the importance of CpG methylation in human cancers.

Materials and Methods

Cell Lines and Tissue Samples

Human tumor cell lines of multiple tissue types were used[50-55], including nasopharyngeal (NPC), esophageal squamous cell (ESCC), lung, gastric, colorectal (CRC), hepatocellular (HCC), breast, cervical, renal (RCC), bladder and prostate carcinomas, melanoma, as well as non-Hodgkin (NHL), Hodgkin (HL) and nasal natural killer (NK)/T-cell (NKTCL) lymphomas. Immortalized, non-transformed normal epithelial cell lines were used as "normal" controls. Cell lines were obtained from either American Type Culture Collection or collaborators. When needed, cell lines were treated with 10 μmol/L 5-aza-2'-deoxycytidine (Aza) (Sigma-aldrich, St Louis, Mo.) for 3 days, without or with further treatment with 100 nmol/trichostatin A (TSA) (Cayman Chemical Co., Ann Arbor, Mich.) for additional ~16 h as previously[50,53]. Normal adult and fetal tissue RNA and DNA samples were purchased commercially (Stratagene, La Jolla, Calif.; Millipore-Chemicon, Billerica, Mass.). DNA samples of primary carcinomas, nose swab from suspected NPC patients, as well as surgical margin normal tissues, have been described previously[31,51,52].

Establishment of Tumor Methylation by MeDIP-Chip

Methylated DNA immunoprecipitation (MeDIP) coupled with promoter microarray hybridization was performed as previously[31]. Briefly, immunoprecipitation of methylated DNA was performed using monoclonal antibody against 5-methylcytidine (33D3, Diagenode, Seraing, Belgium) labeled with magnetic beads. Total input and immunoprecipitated DNA were labeled with Cy3 or Cy5, respectively, and hybridized to NimbleGen™ HG18 Meth (385K CGI plus) promoter arrays or HG19 (2.1M) Deluxe Promoter arrays (Array Star, Inc., MD). Normal epithelial cell lines and normal tissues were used as controls. Bioinformatics analysis of methylome data was performed as previously[31].

Semi-Quantitative RT-PCR and Quantitative Real-Time PCR (qRT-PCR)

Semi-quantitative RT-PCR and quantitative real-time PCR were performed as described before[50,53], with GAPDH as a control for all the samples shown in previous publications[31,51,52]. qRT-PCR was carried out according to the manufacturer's protocol (HT7900 system; applied Biosystems), with SYBR Green master mix (applied Biosystems) used. Primers used are listed in Table 2.

Bisulfite Treatment of DNA Samples and Promoter Methylation Analysis

CpG island (CGI) analysis for TET1 promoter and exon 1 was performed using CpG island Searcher (http//ccnt.hs-c.usc.edu/cpgislands2). Bisulfite modification of genomic DNA was carried out as described previously[56,57]. For MSP analysis, approximately 50 ng of bisulfited DNA for each sample was amplified with methylation- or unmethylation-specific primer set, according to previously reported MSP protocol[58]. Bisulfite-treated DNA was also amplified using a set of BGS primers, then cloned into pCR4-TOPO vector (Invitrogen, Carlsbad, Calif.), with 8-10 clones randomly picked and sequenced. MSP and BGS primers used are shown in Table 2. Unmethylated gene alleles for these treated samples have been detected in our previous publications, which shows the good quality of these DNA samples[31,51,52].

Genetic Deletion Analysis of TET1

Homozygous deletion of TET1 coding exons 2 and 4 was examined using multiplex genomic DNA PCR, as previously described[51]. Primer sequences are shown in Table 2.

Colony Formation Assay of Tumor Cells

Human TET1 catalytic domain (TET1-CD) cDNA and its catalytic domain mutant (TET1-CD-mut) clones (Addgene, Cambridge, Mass.) were used as templates to generate TET1 constructs with an N-terminal Flag tag, and subcloned into pcDNA3.1 vector (Invitrogen, Carlsbad, Calif.). Cells were cultured overnight in a 12-well plate and transfected with empty vector or TET1-CD, TET1-CD-mut-expressing plasmids using Lipofectamine 2000 (Invitrogen, Carlsbad, Calif.). Forty-eight hours later, transfectants were replated in triplicate and cultured for 10-15 days in complete medium containing G418. Surviving colonies were stained with crystal violet (0.5% w/v) after methanol fixation, with visible colonies (≥50 cells) counted.

TUNEL Assay

Cells cultured on coverslips were fixed with 4% paraformaldehyde, and permeabilized with 0.1% triton X-100. TUNEL (Terminal deoxynucleotidyl transferase dUTP nick end labeling) staining was performed using the In Situ Cell Death Detection Kit (Roche, Mannheim, Germany).

Statistical Analysis

Fisher's exact test and t-tests were performed. All reported p-values were two-sided, and $p<0.05$ was considered statistically significant.

All patents, patent applications, and other publications, including GenBank Accession Numbers, cited in this application are incorporated by reference in the entirety for all purposes.

```
Informal sequence listing

SEQ ID NO: 1 Human TET1 genomic sequence (+151 to +534)
(+151-5'-
TGCCTCTCCACTGTGGACCTTTGGGAACCGACTCCTCACCTCGGGGGCTCGGGCCTTGACTGTGCTGGGAGCCGGTA
GGCGTCCTCCGCGACCCGCCCGCGCCCTCGCGCCCGCCGGGGCCCCGGGCTCCAAAGTTGTGGGGACCGGCGCGAG
TTGGAAAGTTTGCCCGAGGGCTGGTGCAGGCTTGGAGCTGGGGGCCGTGCGCTGCCCTGGGAATGTGACCCGGCCAG
CGGTGAGTTGGGGCCGGGGCAGAGGGCAGGGGTGCGGGGAGCGAGGACTCCGACGCCGAGGCCCGAGGGGGGTCCGG
GAGGCGGCGCTCGGCGCGGGCTGGATGTGGCCGGGGCTCTGCGTCCTTGGCTCTCCCGCTGCCTCAGGGGTGGGCT-
+534)

SEQ ID NO: 2 Human TET1 genomic sequence (+221 to +393)
5'-
GCCGGTAGGCGTCCTCCGCGACCCGCCCGCGCCCCTCGCGCCCGCCGGGGCCCCGGGC
TCCAAAGTTGTGGGGACCGGCGCGAGTTGGAAAGTTTGCCCGAGGGCTGGTGCAGGCTT
GGAGCTGGGGGCCGTGCGCTGCCCTGGGAATGTGACCCGGCCAGCGGTGAGTTGGG-3'

SEQ ID NO: 3 Human TET1 mRNA (9601 nt)
      1    agacactgct gctccggggg gctgacctgg cggggagtgg ccgcgcagtc tgctccggcg 61    ccgctttgtg cgcgcagccg ctggcccctc tactcccggg tctgccccc  gggacacccc 121    tctgcctcgc ccaagtcatg cagccctacc tgcctctcca ctgtggacct ttgggaaccg
```

| Informal sequence listing | | | | |
|---|---|---|---|---|
| 181 | actcctcacc | tcgggggctc | gggccttgac | tgtgctggga gccggtaggc gtcctccgcg |
| 241 | acccgcccgc | gcccctcgcg | cccgccgggg | ccccgggctc caaagttgtg gggaccggcg |
| 301 | cgagttggaa | agtttgcccg | agggctggtg | caggcttgga gctggggggcc gtgcgctgcc |
| 361 | ctgggaatgt | gacccggcca | gcgaccaaaa | ccttgtgtga ctgagctgaa gagcagtgca |
| 421 | tccagattct | cctcagaagt | gagactttcc | aaaggaccaa tgactctgtt cctgcgccc |
| 481 | tttcattttt | tcctactctg | tagctatgtc | tcgatcccgc catgcaaggc cttccagatt |
| 541 | agtcaggaag | gaagatgtaa | acaaaaaaaa | gaaaacagc caactacgaa agacaaccaa |
| 601 | gggagccaac | aaaaatgtgg | catcagtcaa | gactttaagc cctggaaaat taaagcaatt |
| 661 | aattcaagaa | agagatgtta | agaaaaaaac | agaacctaaa ccacccgtgc cagtcagaag |
| 721 | ccttctgaca | agagctggag | cagcacgcat | gaatttggat aggactgagg ttcttttttca |
| 781 | gaacccagag | tccttaacct | gcaatgggtt | tacaatggcg ctacgaagca cctctcttag |
| 841 | caggcgactc | tcccaacccc | cactggtcgt | agccaaatcc aaaaaggttc cactttctaa |
| 901 | gggtttagaa | aagcaacatg | attgtgatta | taagatactc cctgctttgg gagtaaagca |
| 961 | ctcagaaaat | gattcggttc | caatgcaaga | cacccaagtc cttcctgata tagagactct |
| 1021 | aattggtgta | caaaatccct | ctttacttaa | aggtaagagc caagagacaa ctcagttttg |
| 1081 | gtcccaaaga | gttgaggatt | ccaagatcaa | tatccctacc cacagtggcc ctgcagctga |
| 1141 | gatccttcct | gggccactgg | aagggacacg | ctgtggtgaa ggactattct ctgaagagac |
| 1201 | attgaatgat | accagtggtt | ccccaaaaat | gtttgctcag gacacagtgt gtgctccttt |
| 1261 | tccccaaaga | gcaaccccca | aagttacctc | tcaaggaaac cccagcattc agttagaaga |
| 1321 | gttgggttca | cgagtagaat | ctcttaagtt | atctgattct tacctggatc ccattaaaag |
| 1381 | tgaacatgat | tgctacccca | cctccagtct | taataaggtt atacctgact tgaaccttag |
| 1441 | aaactgcttg | gctcttggtg | ggtctacgtc | tcctacctct gtaataaaat tcctcttggc |
| 1501 | aggctcaaaa | caagcgaccc | ttggtgctaa | accagatcat caagaggcct tcgaagctac |
| 1561 | tgcaaatcaa | caggaagttt | ctgataccac | ctctttccta ggacaggcct ttggtgctat |
| 1621 | cccacatcaa | tgggaacttc | ctggtgctga | cccagttcat ggtgaggccc tgggtgagac |
| 1681 | cccagatcta | ccagagattc | ctggtgctat | tccagtccaa ggagaggtct ttggtactat |
| 1741 | tttagaccaa | caagaaactc | ttggtatgag | tgggagtgtt gtcccagact tgcctgtctt |
| 1801 | ccttcctgtt | cctccaaatc | caattgctac | ctttaatgct ccttccaaat ggcctgagcc |
| 1861 | ccaaagcact | gtctcatatg | gacttgcagt | ccagggtgct atacagattt tgcctttggg |
| 1921 | ctcaggacac | actcctcaat | catcatcaaa | ctcagagaaa aattcattac ctccagtaat |
| 1981 | ggctataagc | aatgtagaaa | atgagaagca | ggttcatata agcttcctgc cagctaacac |
| 2041 | tcaggggttc | ccattagccc | ctgagagagg | actcttccat gcttcactgg gtatagccca |
| 2101 | actctctcag | gctggtccta | gcaaatcaga | cagagggagc tcccaggtca gtgtaaccag |
| 2161 | cacagttcat | gttgtcaaca | ccacagtggt | gactatgcca gtgccaatgg tcagtacctc |
| 2221 | ctcttcttcc | tataccactt | tgctaccgac | tttggaaaag aagaaaagaa agcgatgtgg |
| 2281 | ggtctgtgaa | ccctgccagc | agaagaccaa | ctgtggtgaa tgcacttact gcaagaacag |
| 2341 | aaagaacagc | catcagatct | gtaagaaaag | aaaatgtgag gagctgaaaa agaaaccatc |
| 2401 | tgttgttgtg | cctctggagg | ttataaagga | aaacaagagg ccccagaggg aaaagaagcc |
| 2461 | caaagtttta | aaggcagatt | ttgacaacaa | accagtaaat ggccccaagt cagaatccat |

| | Informal sequence listing |
|---|---|
| 2521 | ggactacagt agatgtggtc atggggaaga acaaaaattg gaattgaacc cacatactgt |
| 2581 | tgaaaatgta actaaaaatg aagacagcat gacaggcatc gaggtggaga agtggacaca |
| 2641 | aaacaagaaa tcacagttaa ctgatcacgt gaaaggagat tttagtgcta atgtcccaga |
| 2701 | agctgaaaaa tcgaaaaact ctgaagttga caagaaacga accaaatctc caaaattgtt |
| 2761 | tgtacaaacc gtaagaaatg gcattaaaca tgtacactgt ttaccagctg aaacaaatgt |
| 2821 | ttcatttaaa aaattcaata ttgaagaatt cggcaagaca ttggaaaaca attcttataa |
| 2881 | attcctaaaa gacactgcaa accataaaaa cgctatgagc tctgttgcta ctgatatgag |
| 2941 | ttgtgatcat ctcaagggga gaagtaacgt tttagtattc cagcagcctg gctttaactg |
| 3001 | cagttccatt ccacattctt cacactccat cataaatcat catgctagta tacacaatga |
| 3061 | aggtgatcaa ccaaaaactc ctgagaatat accaagtaaa gaaccaaaag atggatctcc |
| 3121 | cgttcaacca gtctcttat cgttaatgaa agataggaga ttaacattgg agcaagtggt |
| 3181 | agccatagag gccctgactc aactctcaga agccccatca gagaattcct ccccatcaaa |
| 3241 | gtcagagaag gatgaggaat cagagcagag aacagccagt ttgcttaata gctgcaaagc |
| 3301 | tatcctctac actgtaagaa aagacctcca agacccaaac ttacagggag agccaccaaa |
| 3361 | acttaatcac tgtccatctt tggaaaaaca aagttcatgc aacacggtgg ttttcaatgg |
| 3421 | gcaaactact acccttttcca actcacatat caactcagct actaaccaag catccacaaa |
| 3481 | gtcacatgaa tattcaaaag tcacaaattc attatctctt tttataccaa aatcaaattc |
| 3541 | atccaagatt gacaccaata aaagtattgc tcaagggata attactcttg acaattgttc |
| 3601 | caatgatttg catcagttgc caccaagaaa taatgaagtg gagtattgca accagttact |
| 3661 | ggacagcagc aaaaaattgg actcagatga tctatcatgt caggatgcaa cccatacca |
| 3721 | aattgaggaa gatgttgcaa cacagttgac acaacttgct tcgataatta agatcaatta |
| 3781 | tataaaacca gaggacaaaa aagttgaaag tacaccaaca agccttgtca catgtaatgt |
| 3841 | acagcaaaaa tacaatcagg agaagggcac aatacaacag aaaccacctt caagtgtaca |
| 3901 | caataatcat ggttcatcat taacaaaaca aaagaaccca acccagaaaa agacaaaatc |
| 3961 | caccccatca agagatcggc ggaaaaagaa gcccacagtt gtaagttatc aagaaaatga |
| 4021 | tcggcagaag tgggaaaagt tgtcctatat gtatggcaca atatgcgaca tttggatagc |
| 4081 | atcgaaattt caaaattttg ggcaattttg tccacatgat tttcctactg tatttgggaa |
| 4141 | aatttcttcc tcgaccaaaa tatggaaacc actggctcaa acgaggtcca ttatgcaacc |
| 4201 | caaaacagta tttccaccac tcactcagat aaaattacag agatatcctg aatcagcaga |
| 4261 | ggaaaaggtg aaggttgaac cattggattc actcagctta tttcatctta aaacggaatc |
| 4321 | caacgggaag gcattcactg ataaagctta taattctcag gtacagttaa cggtgaatgc |
| 4381 | caatcagaaa gcccatcctt gacccagcc ctcctctcca cctaaccagt gtgctaacgt |
| 4441 | gatggcaggc gatgaccaaa tacggtttca gcaggttgtt aaggagcaac tcatgcatca |
| 4501 | gagactgcca acattgcctg gtatctctca tgaaacaccc ttaccggagt cagcactaac |
| 4561 | tctcaggaat gtaaatgtag tgtgttcagg tggaattaca gtggtttcta ccaaaagtga |
| 4621 | agaggaagtc tgttcatcca gttttggaac atcagaattt tccacagtgg acagtgcaca |
| 4681 | gaaaaatttt aatgattatg ccatgaactt ctttactaac cctacaaaaa acctagtgtc |
| 4741 | tataactaaa gattctgaac tgcccacctg cagctgtctt gatcgagtta tacaaaagaa |

-continued

| | Informal sequence listing |
|---|---|
| 4801 | caaaggccca tattatacac accttggggc aggaccaagt gttgctgctg tcagggaaat |
| 4861 | catggagaat aggtatggtc aaaaaggaaa cgcaataagg atagaaatag tagtgtacac |
| 4921 | cggtaaagaa gggaaaagct ctcatgggtg tccaattgct aagtgggttt taagaagaag |
| 4981 | cagtgatgaa gaaaaagttc tttgtttggt ccggcagcgt acaggccacc actgtccaac |
| 5041 | tgctgtgatg gtggtgctca tcatggtgtg ggatggcatc cctcttccaa tggccgaccg |
| 5101 | gctatacaca gagctcacag agaatctaaa gtcatacaat gggcacccta ccgacagaag |
| 5161 | atgcaccctc aatgaaaatc gtacctgtac atgtcaagga attgatccag agacttgtgg |
| 5221 | agcttcattc tcttttggct gttcatggag tatgtacttt aatggctgta agtttggtag |
| 5281 | aagcccaagc cccagaagat ttagaattga tccaagctct cccttacatg aaaaaaacct |
| 5341 | tgaagataac ttacagagtt tggctacacg attagctcca atttataagc agtatgctcc |
| 5401 | agtagcttac caaaatcagg tggaatatga aaatgttgcc cgagaatgtc ggcttggcag |
| 5461 | caaggaaggt cgtcccttct ctggggtcac tgcttgcctg gacttctgtg ctcatcccca |
| 5521 | cagggacatt cacaacatga ataatggaag cactgtggtt tgtaccttaa ctcgagaaga |
| 5581 | taaccgctct ttgggtgtta ttcctcaaga tgagcagctc catgtgctac ctctttataa |
| 5641 | gctttcagac acagatgagt ttggctccaa ggaaggaatg gaagccaaga tcaaatctgg |
| 5701 | ggccatcgag gtcctggcac cccgccgcaa aaaagaacg tgtttcactc agcctgttcc |
| 5761 | ccgttctgga agaagaggg ctgcgatgat gacagaggtt cttgcacata agataagggc |
| 5821 | agtggaaaag aaacctattc cccgaatcaa gcggaagaat aactcaacaa caacaaacaa |
| 5881 | cagtaagcct tcgtcactgc caaccttagg gagtaacact gagaccgtgc aacctgaagt |
| 5941 | aaaaagtgaa accgaacccc attttatctt aaaaagttca gacaacacta aacttattc |
| 6001 | gctgatgcca tccgctcctc acccagtgaa agaggcatct ccaggcttct cctggtcccc |
| 6061 | gaagactgct tcagccacac cagctcccact gaagaatgac gcaacagcct catgcgggtt |
| 6121 | ttcagaaaga agcagcactc cccactgtac gatgccttcg ggaagactca gtggtgccaa |
| 6181 | tgcagctgct gctgatggcc ctggcatttc acagcttggc gaagtggctc ctctccccac |
| 6241 | cctgtctgct cctgtgatgg agcccctcat taattctgag ccttccactg gtgtgactga |
| 6301 | gccgctaacg cctcatcagc caaaccacca gccctccttc ctcacctctc tcaagacct |
| 6361 | tgcctcttct ccaatggaag aagatgagca gcattctgaa gcagatgagc ctccatcaga |
| 6421 | cgaaccccta tctgatgacc ccctgtcacc tgctgaggag aaattgcccc acattgatga |
| 6481 | gtattggtca gacagtgagc acatcttttt ggatgcaaat attggtgggg tggccatcgc |
| 6541 | acctgctcac ggctcggttt tgattgagtg tgcccggcga gagctgcacg ctaccactcc |
| 6601 | tgttgagcac cccaaccgta atcatccaac ccgcctctcc cttgtctttt accagcacaa |
| 6661 | aaacctaaat aagccccaac atggttttga actaaacaag attaagtttg aggctaaaga |
| 6721 | agctaagaat aagaaaatga aggcctcaga gcaaaaagac caggcagcta atgaaggtcc |
| 6781 | agaacagtcc tctgaagtaa atgaattgaa ccaaattcct tctcataaag cattaacatt |
| 6841 | aacccatgac aatgttgtca ccgtgtcccc ttatgctctc acacacgttg cggggcccta |
| 6901 | taaccattgg gtctgaaggc ttttctcccc ctcttaatgc ctttgctagt gcagtgtatt |
| 6961 | ttttcaaggt gctgttaaaa gaaagtcatg ttgtcgttta ctatcttcat ctcacccatt |
| 7021 | tcaagtctga ggtaaaaaaa taataatgat aacaaaacgg ggtgggtatt cttaactgtg |
| 7081 | actatatttt gacaattggt agaaggtgca cattttaagc aaaaataaaa gttttatagt |

| | Informal sequence listing |
|---|---|
| 7141 | tttaaataca taaagaaatg tttcagttag gcattaacct tgatagaatc actcagtttg |
| 7201 | gtgctttaaa ttaagtctgt ttactatgaa acaagagtca tttttagagg attttaacag |
| 7261 | gttcatgttc tatgatgtaa aatcaagaca cacagtgtta actctacaca gcttctggtg |
| 7321 | cttaaccaca tccacacagt taaaaataag ctgaattatt atttcatggt gccattgttc |
| 7381 | caacatcttc caatcattgc tagaaaattg gcatattcct ttgaaataaa cttatgaaat |
| 7441 | gttttctctc ttaaaatatt tctcctgtgt aaaataaatc attgttgtta gtaatggttg |
| 7501 | gaggctgttc ataaattgta aatatatatt ttaaaagcac tttctatttt taaaagtaac |
| 7561 | ttgaaataat atagtataag aatcctattg tctattgttt gtgcatattt gcatacaaga |
| 7621 | gaaatcattt atccttgctg tgtagagttc catcttgtta actgcagtat gtattctaat |
| 7681 | catgtatatg gtttgtgttc ttttactgtg tcctctcaca ttcaagtatt agcaacttgc |
| 7741 | agtatataaa atagttagat aatgagaagt tgttaattat ctctaaaatt ggaattagga |
| 7801 | agcatatcac caatactgat taacattctc tttggaacta ggtaagagtg gtctcttctt |
| 7861 | attgaacaac ctcaatttag tttcatccca cctttctcag tataatccat gagaggtgtt |
| 7921 | tccaaaagga gatgagggaa caggataggt ttcagaagag tcaaatgctt ctaatgtctc |
| 7981 | aaggtgataa aatacaaaaa ctaagtagac agatatttgt actgaagtct gatacagaat |
| 8041 | tagaaaaaaa aaattcttgt tgaaatattt tgaaaacaaa ttccctacta tcatcacatg |
| 8101 | cctccccaac cccaagtcaa aaacaagagg aatggtacta caaacatggc tttgtccatt |
| 8161 | aagagctaat tcatttgttt atcttagcat actagatttg ggaaaatgat aactcatctt |
| 8221 | ttctgataat tgcctatgtt ctaggtaaca ggaaaacagg cattaagttt atttttagtct |
| 8281 | tcccattttc ttcctattac tttattgact cattttattg caaaacaaaa aggattaccc |
| 8341 | aaacaacatg tttcgaacaa ggagaatttt caatgaaata cttgattctg ttaaaatgca |
| 8401 | gaggtgctat aacattcaaa gtgtcagatt ccttgggagt atggaaaacc taatggtgct |
| 8461 | tctcccttgg aaatgccata ggaagcccac aaccgctaac acttacaatt ttggtgcaaa |
| 8521 | agcaaacagt tccagcaggc tctctaaaga aaaactcatt gtaacttatt aaaataatat |
| 8581 | ctggtgcaaa gtatctgttt tgagcttttg actaatccaa gtaaaggaat atgaagggat |
| 8641 | tgtaaaaaac aaaatgtcca ttgatagacc atcgtgtaca agtagatttc tgcttgttga |
| 8701 | atatgtaaaa tagggtaatt cattgacttg ttttagtatt ttgtgtgcct tagatttccg |
| 8761 | ttttaagaca tgtatatttt tgtgagccta aggtttctta tatacatata agtatataaa |
| 8821 | taagtgattg tttattgctt cagctgcttc aacaagatat ttactagtat tagactatca |
| 8881 | ggaatacacc cttgcgagat tatgttttag attttaggcc ttagctccca ctagaaatta |
| 8941 | tttcttcacc agatttaatg gataaagttt tatggctctt tatgcatcca ctcatctact |
| 9001 | cattcttcga gtctacactt attgaatgcc tgcaaaatct aagtatcact tttattttc |
| 9061 | tttggatcac cacctatgac atagtaaact tgaagaataa aaactaccct cagaaatatt |
| 9121 | tttaaaagaa gtagcaaatt atcttcagta taatccatgg taatgtatgc agtaattcaa |
| 9181 | attgatctct ctctcaatag gtttcttaac aatctaaact tgaaacatca atgttaattt |
| 9241 | ttggaactat tgggatttgt gacgcttgtt gcagtttacc aaaacaagta tttgaaaata |
| 9301 | tatagtatca actgaaatgt ttccattccg ttgttgtagt taacatcatg aatggacttc |
| 9361 | ttaagctgat taccccactg tgggaaccaa attggattcc tactttgttg gactctcttt |

| Informal sequence listing |
|---|
| 9421  cctgatttta acaatttacc atcccattct ctgccctgtg attttttta aaagcttatt |
| 9481  caatgttctg cagcattgtg attgtatgct ggctacactg cttttagaat gctctttctc |
| 9541  atgaagcaag gaaataaatt tgtttgaaat gacattttct ctcaaaaaaa aaaaaaaaaa |
| 9601  a |

SEQ ID NO: 4 sequence for coding region (6411 nt):
ATGTCTCGATCCCGCCATGCAAGGCCTTCCAGATTAGTCAGGAAGGAAGATGTAAACAAAAAAAGAAAA
ACAGCCAACTACGAAAGACAACCAAGGGAGCCAACAAAAATGTGGCATCAGTCAAGACTTTAAGCCCTGG
AAAATTAAAGCAATTAATTCAAGAAAGAGATGTTAAGAAAAAAACAGAACCTAAACCACCCGTGCCAGTC
AGAAGCTTCTGACAAGAGCTGGAGCAGCACGCATGAATTTGGATAGGACTGAGGTTCTTTTTCAGAACC
CAGAGTCCTTAACCTGCAATGGGTTTACAATGGCGCTACGAAGCACCTCTCTTAGCAGGCGACTCTCCCA
ACCCCCACTGGTCGTAGCCAAATCCAAAAAGGTTCCACTTTCTAAGGGTTTAGAAAAGCAACATGATTGT
GATTATAAGATACTCCCTGCTTTGGGAGTAAAGCACTCAGAAAATGATTCGGTTCCAATGCAAGACACCC
AAGTCCTTCCTGATATAGAGACTCTAATTGGTGTACAAAATCCCTCTTTACTTAAAGGTAAGAGCCAAGA
GACAACTCAGTTTTGGTCCCAAAGAGTTGAGGATTCCAAGATCAATATCCCTACCCACAGTGGCCCTGCA
GCTGAGATCCTTCCTGGGCACTGGAAGGGACACGCTGTGGTGAAGGACTATTCTCTGAAGAGACATTGA
ATGATACCAGTGGTTCCCCAAAAATGTTTGCTCAGGACACAGTGTGTGCTCCTTTTCCCAAAGAGCAAC
CCCCAAAGTTACCTCTCAAGGAAACCCCAGCATTCAGTTAGAAGAGTTGGGTTCACGAGTAGAATCTCTT
AAGTTATCTGATTCTTACCTGGATCCCATTAAAAGTGAACATGATTGCTACCCCACCTCCAGTCTTAATA
AGGTTATACCTGACTTGAACCTTAGAAACTGCTTGGCTCTTGGTGGGTCTACGTCTCCTACCTCTGTAAT
AAAATTCCTCTTGGCAGGCTCAAAACAAGCGACCCTTGGTGCTAAACCAGATCATCAAGAGGCCTTCGAA
GCTACTGCAAATCAACAGGAAGTTTCTGATACCACCTCTTTCCTAGGACAGGCCTTTGGTGCTATCCCAC
ATCAATGGGAACTTCCTGGTGCTGACCCAGTTCATGGTGAGGCCCTGGGTGAGACCCCAGATCTACCAGA
GATTCCTGGTGCTATTCCAGTCCAAGGAGAGGTCTTTGGTACTATTTTAGACCAACAAGAAACTCTTGGT
ATGAGTGGGAGTGTTGTCCCAGACTTGCCTGTCTTCCTTCCTGTTCCTCCAAATCCAATTGCTACCTTTA
ATGCTCCTTCCAAATGGCCTGAGCCCCAAAGCACTGTCTCATATGGACTTGCAGTCCAGGGTGCTATACA
GATTTTGCCTTTGGGCTCAGGACACACTCCTCAATCATCATCAAACTCAGAGAAAATTCATTACCTCCA
GTAATGGCTATAAGCAATGTAGAAAATGAGAAGCAGGTTCATATAAGCTTCCTGCCAGCTAACACTCAGG
GGTTCCCATTAGCCCCTGAGAGAGGACTCTTCCATGCTTCACTGGGTATAGCCCAACTCTCTCAGGCTGG
TCCTAGCAAATCAGACAGAGGGAGCTCCCAGGTCAGTGTAACCAGCACAGTTCATGTTGTCAACACCACA
GTGGTGACTATGCCAGTGCCAATGGTCAGTACCTCCTCTTCTTCCTATACCACTTTGCTACCGACTTTGG
AAAAGAAGAAAAGAAAGCGATGTGGGGTCTGTGAACCCTGCCAGCAGAAGACCAACTGTGGTGAATGCAC
TTACTGCAAGAACAGAAAAGAACAGCCATCAGATCTGTAAGAAAGAAAATGTGAGGAGCTGAAAAAGAAA
CCATCTGTTGTTGTGCCTCTGGAGGTTATAAAGGAAAACAAGAGGCCCCAGAGGGAAAAGAAGCCCAAAG
TTTTAAAGGCAGATTTTGACAACAAACCAGTAAATGGCCCCAAGTCAGAATCCATGGACTACAGTAGATG
TGGTCATGGGGAAGAACAAAAATTGGAATTGAACCCACATACTGTTGAAAATGTAACTAAAAATGAAGAC
AGCATGACAGGCATCGAGGTGGAGAAGTGGACACAAAACAAGAAATCACAGTTAACTGATCACGTGAAAG
GAGATTTTAGTGCTAATGTCCCAGAAGCTGAAAAATCGAAAAACTCTCAAGTTGACAAGAAACGAACCAA
ATCTCCAAAATTGTTTGTACAAACCGTAAGAAATGGCATTAAACATGTACACTGTTTACCAGCTGAAACA
AATGTTTCATTTAAAAAATTCAATATTGAAGAATTCGGCAAGACATTGGAAAACAATTCTTATAAATTCC
TAAAAGACACTGCAAACCATAAAAACGCTATGAGCTCTGTTGCTACTGATATGAGTTGTGATCATCTCAA
GGGGAGAAGTAACGTTTTAGTATTCCAGCAGCCTGGCTTTAACTGCAGTTCCATTCCACATTCTTCACAC
TCCATCATAAATCATCATGCTAGTATACACAATGAAGGTGATCAACCAAAAACTCCTGAGAATATACCAA
GTAAAGAACCAAAAGATGGATCTCCCGTTCAACCAAGTCTCTTATCGTTAATGAAAGATAGGAGATTAAC
ATTGGAGCAAGTGGTAGCCATAGAGGCCCTGACTCAACTCTCAGAAGCCCCATCAGAGAATTCCTCCCCA
TCAAAGTCAGAGAAGGATGAGGAATCAGAGCAGAGAACAGCCAGTTTGCTTAATAGCTGCAAAGCTATCC
TCTACACTGTAAGAAAAGACCTCCAAGACCCAAACTTACAGGGAGAGCCACCAAAACTTAATCACTGTCC
ATCTTTGGAAAAACAAAGTTCATGCAACACGGTGGTTTTCAATGGGCAAACTACTACCCTTTCCAACTCA
CATATCAACTCAGCTACTAACCAAGCATCCACAAAGTCACATGAATATTCAAAGTCACAAATTCATTAT
CTCTTTTTATACCAAAATCAAATTCATCCAAGATTGACACCAATAAAAGTATTGCTCAAGGGATAATTAC
TCTTGACAATTGTTCCAATGATTTGCATCAGTTGCCACCAAGAAATAATGAAGTGGAGTATTGCAACCAG
TTACTGGACAGCAGCAAAAATTGGACTCAGATGATCTATCATGTCAGGATGCAACCCATACCCAAATTG
AGGAAGATGTTGCAACACAGTTGACACAACTTGCTTCGATAATTAAGATCAATTATATAAAACCAGAGGA
CAAAAAGTTGAAAGTACACCAACAAGCCTTGTCACATGTAATGTACAGCAAAAATACAATCAGGAGAAG
GGCACAATACAACAGAAACCACCTTCAAGTGTACACAATAATCATGGTTCATCATTAACAAAACAAAAGA
ACCCAACCCAGAAAAGACAAAATCCACCCCATCAAGAGATCGGCGGAAAAAGAAGCCCACAGTTGTAAG
TTATCAAGAAAATGATCGGCAGAAGTGGGAAAAGTTGTCCTATATGTATGGCACAATATGCGACATTTGG
ATAGCATCGAAATTTCAAAATTTTGGGCAATTTTGTCCACATGATTTTCCTACTGTATTTGGGAAAATTT
CTTCCTCGACCAAAATATGGAAACCACTGGCTCAAACGAGGTCCATTATGCAACCCAAAACAGTATTTCC
ACCACTCACTCAGATAAAATTACAGAGATATCCTGAATCAGCAGAGGAAAAGGTGAAGGTTGAACCATTG
GATTCACTCAGCTTATTTCATCTTAAAACGGAATCCAACGGGAAGGCATTCACTGATAAAGCTTATAATT
CTCAGGTACAGTTAACGGTGAATGCCAATCAGAAAGCCCATCCTTTGACCCAGCCCTCCTCTCCACCTAA
CCAGTGTGCTAACGTGATGGCAGGCGATGACCAAATACGGTTTCAGCAGGTTGTTAAGGAGCAACTCATG
CATCAGAGACTGCCAACATTGCCTGGTATCTCTCATGAAACACCCTTACCGGAGTCAGCACTAACTCTCA
GGAATGTAAATGTAGTGTGTTCAGGTGGAATTACAGTGGTTTCTACCAAAAGTGAAGAGGAAGTCTGTTC
ATCCAGTTTGGAACATCAGATTTTCCACAGTGGACAGTGCACAGAAAAATTTTAATGATTATGCCATG
AACTTCTTTACTAACCCTACAAAAAACCTAGTGTCTATAACTAAAGATTCTGAACTGCCCACCTGCAGCT
GTCTTGATCGAGTTATACAAAAAGACAAAGGCCCATATTATACACACCTTGGGGCAGGACCAAGTGTTGC
TGCTGTCAGGGAAATCATGGAGAATAGGGTATGGTCAAAAAGGAAACGCAATAAGGATAGAAATAGTAGTG
TACACCGGTAAAGAAGGGAAAGCTCTCATGGGTGTCCAATTGCTAAGTGGGTTTTAAGAAGAAGCAGTG
ATGAAGAAAAGTTCTTTGTTTGGTCCGGCAGCGTACAGGCCACCACTGTCCAACTGCTGTGATGGTGGT
GCTCATCATGGTGTGGGATGGCATCCCTCTTCCAATGGCCGACCGGCTATACACAGAGCTCACAGAGAAT
CTAAAGTCATACAATGGGCACCCTACCGACAGAAGATGCACCCTCAATGAAAATCGTACCTGTACATGTC
AAGGAATTGATCCAGAGACTTGTGGAGCTTCATTCTCTTTTGGCTGTTCATGGAGTATGTACTTTAATGG

|                          Informal sequence listing                           |
| --- |

CTGTAAGTTTGGTAGAAGCCCAAGCCCCAGAAGATTTAGAATTGATCCAAGCTCTCCCTTACATGAAAAA
AACCTTGAAGATAACTTACAGAGTTTGGCTACACGATTAGCTCCAATTTATAAGCAGTATGCTCCAGTAG
CTTACCAAAATCAGGTGGAATATGAAAATGTTGCCCGAGAATGTCGGCTTGGCAGCAAGGAAGGTCGTCC
CTTCTCTGGGGTCACTGCTTGCCTGGACTTCTGTGCTCATCCCCACAGGGACATTCACAACATGAATAAT
GGAAGCACTGTGGTTTGTACCTTAACTCGAGAAGATAACCGCTCTTTGGGTGTTATTCCTCAAGATGAGC
AGCTCCATGTGCTACCTCTTTATAAGCTTTCAGACACAGATGAGTTTGGCTCCAAGGAAGGAATGGAAGC
CAAGATCAAATCTGGGGCCATCGAGGTCCTGGCACCCCGCCGCAAAAAAGAACGTGTTTCACTCAGCCT
GTTCCCCGTTCTGGAAAGAAGAGGGCTGCGATGATGACAGAGGTTCTTGCACATAAGATAAGGGCAGTGG
AAAAGAAACCTATTCCCCGAATCAAGCGGAAGAATAACTCAACAACAACAAACAACAGTAAGCCTTCGTC
ACTGCCAACCTTAGGGAGTAACACTGAGACCGTGCAACCTGAAGTAAAAAGTGAAACCGAACCCCATTTT
ATCTTAAAAAGTTCAGACAACACTAAAACTTATTCGCTGATGCCATCCGCTCCTCACCCAGTGAAAGAGG
CATCTCCAGGCTTCTCCTGGTCCCCGAAGACTGCTTCAGCCACACCAGCTCCACTGAAGAATGACGCAAC
AGCCTCATGCGGGTTTTCAGAAAGAAGCAGCACTCCCCACTGTACGATGCCTTGGGAAGACTCAGTGGT
GCCAATGCAGCTGCTGCTGATGGCCCTGGCATTTCACAGCTTGGCGAAGTGGCTCCTCTCCCCACCCTGT
CTGCTCCTGTGATGGAGCCCCTCATTAATTCTGAGCCTTCCACTGGTGTGACTGAGCCGCTAACGCCTCA
TCAGCCAAACCACCAGCCCTCCTTCCTCACCTCTCCTCAAGACCTTGCCTCTTCTCAATGGAAGAAGAT
GAGCAGCATTCTGAAGCAGATGAGCCTCCATCAGACGAACCCCTATCTGATGACCCCTGTCACCTGCTG
AGGAGAAATTGCCCCACATTGATGAGTATTGGTCAGACAGTGAGCACATCTTTTTGGATGCAAATATTGG
TGGGGTGGCCATCGCACCTGCTCACGGCTCGGTTTTGATTGAGTGTGCCCGGCGAGAGCTGCACGCTACC
ACTCCTGTTGAGCACCCCAACCGTAATCATCCAACCCGCCTCTCCCTTGTCTTTTACCAGCACAAAAACC
TAAATAAGCCCCAACATGGTTTTGAACTAAACAAGATTAAGTTTGAGGCTAAAGAAGCTAAGAATAAGAA
AATGAAGGCCTCAGAGCAAAAAGACCAGGCAGCTAATGAAGGTCCAGAACAGTCCTCTGAAGTAAATGAA
TTGAACCAAATTCCTTCTCATAAAGCATTAACATTAACCCATGACAATGTTGTCACCGTGTCCCCTTATG
CTCTCACACACGTTGCGGGGCCCTATAACCATTGGGTCTGA

SEQ ID NO: 5 human TET1 protein 2136-amino acid
MSRSRHARPSRLVRKEDVNKKKKNSQLRKTTKGANKNVASVKTLSPGKLKQLIQERDVKKKTEPKPPVPV
RSLLTRAGAARMNLDRTEVLFQNPESLTCNGFTMALRSTSLSRRLSQPPLVVAKSKKVPLSKGLEKQHDC
DYKILPALGVKHSENDSVPMQDTQVLPDIETLIGVQNPSLLKGKSQETTQFWSQRVEDSKINIPTHSGPA
AEILPGPLEGTRCGEGLFSEETLNDTSGSPKMFAQDTVCAPFPQRATPKVTSQGNPSIQLEELGSRVESL
KLSDSYLDPIKSEHDCYPTSSLNKVIPDLNLRNCLALGGSTSPTSVIKFLLAGSKQATLGAKPDHQEAFE
ATANQQEVSDTTSFLGQAFGAIPHQWELPGADPVHGEALGETPDLPEIPGAIPVQGEVFGTILDQQETLG
MSGSVVPDLPVFLPVPPNPIATFNAPSKWPEPQSTVSYGLAVQGAIQILPLGSGHTPQSSSNSEKNSLPP
VMAISNVENEKQVHISFLPANTQGFPLAPERGLFHASLGIAQLSQAGPSKSDRGSSQVSVTSTVHVVNTT
VVTMPVPMVSTSSSSYTTLLPTLEKKKRKRCGVCEPCQQKTNCGECTYCKNRKNSHQICKKRKCEELKKK
PSVVVPLEVIKENKRPQREKKPKVLKADFDNKPVNGPKSESMDYSRCGHGEEQKLELNPHTVENVTKNED
SMTGIEVEKWTQNKKSQLTDHVKGDFSANVPEAEKSKNSEVDKKRTKSPKLFVQTVRNGIKHVHCLPAET
NVSFKKFNIEEFGKTLENNSYKFLKDTANHKNAMSSVATDMSCDHLKGRSNVLVFQQPGFNCSSIPHSSH
SIINHHASIHNEGDQPKTPENIPSKEPKDGSPVQPSLLSLMKDRRLTLEQVVAIEALTQLSEAPSENSSP
SKSEKDEESEQRTASLLNSCKAILYTVRKDLQDPNLQGEPPKLNHCPSLEKQSSCNTVVFNGQTTTLSNS
HINSATNQASTKSHEYSKVTNSLSLFIPKSNSSKIDTNKSIAQGIITLDNCSNDLHQLPPRNNEVEYCNQ
LLDSSKKLDSDDLSCQDATHTQIEEDVATQLTQLASIIKINYIKPEDKKVESTPTSLVTCNVQQKYNQEK
GTIQQKPPSSVHNNHGSSLTKQKNPTQKKTKSTPSRDRRKKKPTVVSYQENDRQKWEKLSYMYGTICDIW
IASKFQNFGQFCPHDFPTVFGKISSSTKIWKPLAQTRSIMQPKTVFPPLTQIKLQRYPESAEEKVKVEPL
DSLSLFHLKTESNGKAFTDKAYNSQVQLTVNANQKAHPLTQPSSPPNQCANVMAGDDQIRFQQVVKEQLM
HQRLPTLPGISHETPLPESALTLRNVNVVCSGGITVVSTKSEEEVCSSSFGTSEFSTVDSAQKNFNDYAM
NFFTNPTKNLVSITKDSELPTCSCLDPVIQKDKGPYYTHLGAGPSVAAVPEIMENRYGQKGNAIRIEIVV
YTGKEGKSSHGCPIAKWVLRRSSDEEKVLCLVPQRTGHHCPTAVMVVLIMVWDGIPLPMADRLYTELTEN
LKSYNGHPTDRRCTLNENRTCTCQGIDPETCGASFSFGCSWSMYFNGCKFGRSPSPRRFRIDPSSPLHEK
NLEDNLQSLATRLAPIYKQYAPVAYQNQVEYENVARECRLGSKEGRPFSGVTACLDFCAHPHRDIHNMNN
GSTVVCTLTREDNPSLGVIPQDEQLHVLPLYKLSDTDEFGSKEGMEAKIKSGAIEVLAPRPKKRTCPTQP
VPRSGKKRAAMMTEVLAEKIPAVEKKPIPPIKRKNNSTTTNNSKPSSLPTLGSNTETVQPEVKSETEPHF
ILKSSDNTKTYSLMPSAPHPVKEASPGFSWSPKTASATPAPLKNDATASCGFSERSSTPHCTMPSGRLSG
ANAAAAADGPGISQLGEVAPLPTLSAPVMEPLINSEPSTGVTEPLTPHQPNHQPSFLTSPQDLASSPMEED
EQHSEADEPPSDEPLSDDPLSPAEEKLPHIDEYWSDSEHIFLDANIGGVAIAPAHGSVLIECARRELHAT
TPVEHPNRNHPTRLSLVFYQHKNLNKPQHGFELNKIKFEAKEAKNKKMKASEQKDQAANEGPEQSSEVNE
LNQIPSHKALTLTHDNVVTVSPYALTHVAGPYNHWV, SEQ ID NO: 6 TET1 catalytic domain, the 1418 to 2136 fragment of SEQ ID NO: 5
ELPTCSCLDRVIQKDKGPYYTHLGAGPSVAAVREIMENRYGQKGNAIRIEIVVYTGKEGKSSHGCPIAKWVLRRSSD
EEKVLCLVRQRTGHHCPTAVMVVLIMVWDGIPLPMADFLYTELTENLKSYNGRPTDRRCTLNENRTCTCQGIDPETC
GASFSFGCSWSMYFNGCKFGRSPSPRRFRIDPSSPLHEKNLEDNLQSLATRLAPIYKQYAPVAYQNQVEYENVAREC
RLGSKEGRPFSGVTACLDFCAHPHRDIHNMNNGSTVVCTLTREDNPSLGVIPQDEQLHVLPLYKLSDTDEFGSKEGM
EAKIKSGAIEVLAPRRKKPTCFTQPVPPSGKKRAAMMTEVLAKKTRAVEKKPIPRIKPKNNSTTTNNSKPSSLPTLG
SNTETVQPEVKSETEPHFILKSSDNTKTYSLMPSAPHPVKEASPGFSWSPKTASATPAPLKNDATASCGFSERSSTP
HCTMPSGRLSGANAAAADGPGISQLGEVAPLPTLSAPVMEPLINSEPSTGVTEPLTPHQPNHQPSFLTSPQDLASSP
MEEDEQHSEADEPPSDEPLSDDPLSPAEEKLPHIDEYWSDSEHIFLDANIGGVAIAPAHGSVLIECARRELHAT
TPVEHPNRNHPTRLSLVFYQHKNLNKPQHGFELNKIKFEAKEAKNKKMKASEQKDQAANEGPEQSSEVNE
LNQIPSHKALTLTHDNVVTVSPYALTHVAGPYNHWV

TABLE 1

Summary of TET1 methylation in tumor and normal tissues

| | | Cell lines (% methylated) | Primary tumors (% methylated) |
|---|---|---|---|
| Carcinomas | Nasopharyngeal (NPC) | 100% (5/5) | 55% (31/56) |
| | Esophageal (ESCC) | 50% (3 + 1w/8) | 18% (7/38) |
| | Lung | 80% (4/5) | 13% (2/16) |
| | Gastric | 92% (11 + 1w/16) | 55% (30/55) |
| | Hepatocellular (HCC) | 63% (5/8) | 42% (5/12) |
| | Colorectal (CRC) | 64% (6 + 1w/11) | 27% (3/11) |
| | Breast | 56% (4 + 1w/9) | 36% (18/50) |
| | Cervical | 75% (2 + 1w/4) | |
| | Renal | 78% (6 + 1w/9) | 28% (13/46) |
| | Prostate | 33% (1/3) | 22% (2/9) |
| Lymphomas | non-Hodgkin | 85% (11/13) | eBL, 50% (3/6) DLBCL, 20%(2/10) |
| | Hodgkin | 100% (8/8) | 78% (5 + 2w/9) |
| | Nasal, NK/T-cell (NKTCL) | 100% (4/4) | 83% (10/12) |
| Screen tissue | Nose swab from NPC patients | | 50% (8/16) |
| Immortalized normal epithelial cell lines | NP460, NP69, Het-1A, NE1, NE3, NE083, HMEC, HMEpC, CCD841-CoN, HEK293, RHEK-1, | 0 (0/11) | |
| Surgical margin tissues of tumors | breast tissues | | 20% (1/5) |
| Normal tissues | Normal nasopharynx (NPx) | | 0 (0/5) |
| | Normal breast tissues | | 0 (0/22) |

W, weak methylation;
NPC, nasopharyngeal carcinoma;
ESCC, esophageal squamous carcinoma;
HCC, hepatocellular carcinoma;
CRC, colorectal carcinoma;
eBL, endemic Burkitt lymphoma;
DLBCL, diffuse large B-cell lymphoma

TABLE 2

Sequences of primer used in this study

| PCR | Primers | Sequence (5'-3') | SEQ ID NO: | Product size | Annealing Temp.(° C.) | Cycles |
|---|---|---|---|---|---|---|
| RT-PCR | TET1F | GTGCCAATGGTCAGTACCTC | 7 | 329 bp | 55 | 32 |
| | TET1R | CTGTAGTCCATGGATTCTGA | 8 | | | |
| | HOXA5F | CTGGATGCGCAAGCTGCACA | 9 | 251 bp | 55 | 32 |
| | HOXA5R | CCATGCTCATGCTTTTCAGC | 10 | | | |
| | HOXA9F | GTGTACCACCACCATCACCA | 11 | 192 bp | 55 | 32 |
| | HOXA9R | AGCGCGCATGAAGCCAGTTG | 12 | | | |
| | PCDH7F | GTTCCGAGTACCTGAAGATC | 13 | 208 bp | 55 | 32 |
| | PCDH7R | GTGTTGTCGTTGATGTCAAG | 14 | | | |
| | TCF4F | TAGGGACGGACAAAGAGCTG | 15 | 168 bp | 55 | 32 |
| | TCF4R | TTGGATGTCCTCCATTCCCC | 16 | | | |
| | MEIS1F | GGAGCCAGAGAGGCCGATG | 17 | 192 bp | 55 | 32 |
| | MEIS1R | ATGGCGTTGGTATGAGCTGTG | 18 | | | |
| | SLIT2F | TGCTGGCGATCCTGAACAAG | 19 | 260 bp | 55 | 32 |
| | SLIT2R | AAGATCCTGGAATGCTCCTC | 20 | | | |
| | ZNF382F | CCTTACAGGGATCAGTGTCA | 21 | 173 bp | 55 | 32 |
| | ZNF382R | CAACTTGCGGATCATATCAG | 22 | | | |
| | GAPDH55 | ATCTCTGCCCCCTCTGCTGA | 23 | 303 bp | 55 | 23 |
| | GAPDH33 | GATGACCTTGCCCACAGCCT | 24 | | | |
| Multiplex | TET1F | GTGCCAATGGTCAGTACCTC | 25 | 296 bp (exon 2) | | |
| genomic | TET1Int2R | GACACTAGAAGTGTCTCTGC | 26 | | | |
| DNA-PCR | TET1Int4F | TGCGATTACAGGTGTGAGTC | 27 | 281 bp (exon 4) | | |
| | TET1R | CTGTAGTCCATGGATTCTGA | 28 | | | |
| | GAPDHInt7F | GCCTCACTCCTTTTGCAGAC | 29 | 155 bp | | |
| | GAPDH33 | GATGACCTTGCCCACAGCCT | 30 | | | |

TABLE 2-continued

Sequences of primer used in this study

| PCR | Primers | Sequence (5'-3') | SEQ ID NO: | Product size | Annealing Temp.(° C.) | Cycles |
|---|---|---|---|---|---|---|
| MSP | TET1m4 | GTCGGTAGGGTTTTTCGC | 31 | 173 bp | 60 | 40 |
| | TET1m8 | CCCAACTCACCGCTAACCG | 32 | | | |
| | TET1u4 | GAGTTGGTAGGTGTTTTTTGT | 33 | 175 bp | 58 | 40 |
| | TET1u8 | CCCAACTCACCACTAACCA | 34 | | | |
| | HOXA9m3 | ATTCGTTTTTGTTGGGCGTC | 35 | | | |
| | HOXA9m4 | GCAACGAATACAACGTTAACG | 36 | | 60 | 40 |
| | HOXA9u3 | GGATTTGTTTTTGTTGGGTGTT | 37 | | | |
| | HOXA9u4 | CCACAACAAATACAACATTAACA | 38 | | 58 | 40 |
| | SLIT2m5 | GATCGGTTTAGGTTGCGGC | 39 | | | |
| | SLIT2m7 | AACAACTAAACATAACGCGCG | 40 | | 60 | 40 |
| | SLIT2u5 | GGATTGGTTTAGGTTGTGGT | 41 | | | |
| | SLIT2u7 | AAAACAACTAAACATAACACACA | 42 | | 58 | 40 |
| | ZNF382m3 | GGCGATTAACGGGTCGTTTC | 43 | | | |
| | ZNF382m5 | AAAATTTCCAAACCCGACTCG | 44 | | 60 | 40 |
| | ZNF382u3 | GTGGTGATTAATGGGTTGTTTT | 45 | | | |
| | ZNF382u5 | CAAAATTTCCAAACCCAACTCA | 46 | | 58 | 40 |
| BGS | TET1BGS6 | TTGTTTTTTTATTGTGGATTTTTG | 47 | 384 bp | 60 | 40 |
| | TET1BGS2 | AACCCACCCCTAAAACAAC | 48 | | | |
| Cloning | TET1-CF | CGGAATTCGCCACCATGGATTACAAGGATGACGACGATAAGTACCCATACGATGTTCCAGA | 49 | 2266 bp | 58 | 18 |
| | TET1-CR | GCTCTAGATTAGTGGTGATGGTGATGATGGACCCAATGGTTATAGGGC | 50 | | | |

LIST OF REFERENCES

1 Jones, P. A. & Baylin, S. B. The epigenomics of cancer. *Cell* 128, 683-692, doi:10.1016/j.cell.2007.01.029 (2007).

2 Schubeler, D. Function and information content of DNA methylation. *Nature* 517, 321-326, doi:10.1038/nature14192 (2015).

3 You, J. S. & Jones, P. A. Cancer genetics and epigenetics: two sides of the same coin? *Cancer cell* 22, 9-20, doi:10.1016/j.ccr.2012.06.008 (2012).

4 Hamidi, T., Singh, A. K. & Chen, T. Genetic alterations of DNA methylation machinery in human diseases. *Epigenomics* 7, 247-265, doi:10.2217/epi.14.80 (2015).

5 Vogelstein, B. et al. Cancer genome landscapes. *Science* 339, 1546-1558, doi:10.1126/science.1235122 (2013).

6 Tahiliani, M. et al. Conversion of 5-methylcytosine to 5-hydroxymethylcytosine in mammalian DNA by MLL partner TET1. *Science* 324, 930-935, doi:10.1126/science.1170116 (2009).

7 Jin, S. G. et al. 5-Hydroxymethylcytosine is strongly depleted in human cancers but its levels do not correlate with IDH1 mutations. *Cancer research* 71, 7360-7365, doi:10.1158/0008-5472.CAN-11-2023 (2011).

8 Haffner, M. C. et al. Global 5-hydroxymethylcytosine content is significantly reduced in tissue stem/progenitor cell compartments and in human cancers. *Oncotarget* 2, 627-637 (2011).

9 Kudo, Y. et al. Loss of 5-hydroxymethylcytosine is accompanied with malignant cellular transformation. *Cancer science* 103, 670-676, doi:10.1111/j.1349-7006.2012.02213.x (2012).

10 Bachman, M. et al. 5-Hydroxymethylcytosine is a predominantly stable DNA modification. *Nature chemistry* 6, 1049-1055, doi:10.1038/nchem.2064 (2014).

11 Lian, C. G. et al. Loss of 5-hydroxymethylcytosine is an epigenetic hallmark of melanoma. *Cell* 150, 1135-1146, doi:10.1016/j.cell.2012.07.033 (2012).

12 Tan, L. & Shi, Y. G. Tet family proteins and 5-hydroxymethylcytosine in development and disease. *Development* 139, 1895-1902, doi:10.1242/dev.070771 (2012).

13 Guo, J. U., Su, Y., Zhong, C., Ming, G. L. & Song, H. Hydroxylation of 5-methylcytosine by TET1 promotes active DNA demethylation in the adult brain. *Cell* 145, 423-434, doi:10.1016/j.cell.2011.03.022 (2011).

14 Delhommeau, F. et al. Mutation in TET2 in myeloid cancers. *The New England journal of medicine* 360, 2289-2301, doi:10.1056/NEJMoa0810069 (2009).

15 Konstandin, N. et al. Genomic 5-hydroxymethylcytosine levels correlate with TET2 mutations and a distinct global gene expression pattern in secondary acute myeloid leukemia. *Leukemia* 25, 1649-1652, doi:10.1038/leu.2011.134 (2011).

16 Moran-Crusio, K. et al. Tet2 loss leads to increased hematopoietic stem cell self-renewal and myeloid transformation. *Cancer cell* 20, 11-24, doi:10.1016/j.ccr.2011.06.001 (2011).

17 Ito, S. et al. Role of Tet proteins in 5mC to 5hmC conversion, ES-cell self-renewal and inner cell mass specification. *Nature* 466, 1129-1133, doi:10.1038/nature09303 (2010).

18 Yamaguchi, S., Shen, L., Liu, Y., Sendler, D. & Zhang, Y. Role of Tet1 in erasure of genomic imprinting. *Nature* 504, 460-464, doi:10.1038/nature12805 (2013).

19 Wu, H. et al. Dual functions of Tet1 in transcriptional regulation in mouse embryonic stem cells. *Nature* 473, 389-393, doi:10.1038/nature09934 (2011).

20 Dawlaty, M. M. et al. Tet1 is dispensable for maintaining pluripotency and its loss is compatible with embryonic and postnatal development. *Cell Stem Cell* 9, 166-175, doi:10.1016/j.stem.2011.07.010 (2011).

21 Spruijt, C. G. et al. Dynamic readers for 5-(hydroxy)methylcytosine and its oxidized derivatives. *Cell* 152, 1146-1159, doi:10.1016/j.cell.2013.02.004 (2013).

22 Yang, H. et al. Tumor development is associated with decrease of TET gene expression and 5-methylcytosine hydroxylation. *Oncogene* 32, 663-669, doi:10.1038/onc.2012.67 (2013).

23 Neri, F. et al. TET1 is a tumour suppressor that inhibits colon cancer growth by derepressing inhibitors of the WNT pathway. *Oncogene*, doi:10.1038/onc.2014.356 (2014).

24 Sun, M. et al. HMGA2/TET1/HOXA9 signaling pathway regulates breast cancer growth and metastasis. *Proceedings of the National Academy of Sciences of the United States of America* 110, 9920-9925, doi:10.1073/pnas.1305172110 (2013).

25 Hsu, C. H. et al. TET1 suppresses cancer invasion by activating the tissue inhibitors of metalloproteinases. *Cell reports* 2, 568-579, doi:10.1016/j.celrep.2012.08.030 (2012).

26 Wu, B. K. & Brenner, C. Suppression of TET1-dependent DNA demethylation is essential for KRAS-mediated transformation. *Cell reports* 9, 1827-1840, doi:10.1016/j.celrep.2014.10.063 (2014).

27 Song, S. J. et al. MicroRNA-antagonism regulates breast cancer stemness and metastasis via TET-family-dependent chromatin remodeling. *Cell* 154, 311-324, doi:10.1016/j.cell.2013.06.026 (2013).

28 Wang, Y. & Zhang, Y. Regulation of TET1 protein stability by calpains. *Cell reports* 6, 278-284, doi:10.1016/j.celrep.2013.12.031 (2014).

29 Muller, T. et al. Nuclear exclusion of TET1 is associated with loss of 5-hydroxymethylcytosine in IDH1 wild-type gliomas. *The American journal of pathology* 181, 675-683, doi:10.1016/j.ajpath.2012.04.017 (2012).

30 Huang, Y. et al. Loss of nuclear localization of TET2 in colorectal cancer. *Clin Epigenetics* 8, 9, doi:10.1186/s13148-016-0176-7 (2016).

31 Li, L. et al. Characterization of the nasopharyngeal carcinoma methylome identifies aberrant disruption of key signaling pathways and methylated tumor suppressor genes. *Epigenomics* 7, 155-173, doi:10.2217/epi.14.79 (2015).

32 Huang, Y. & Rao, A. Connections between TET proteins and aberrant DNA modification in cancer. *Trends Genet* 30, 464-474, doi:10.1016/j.tig.2014.07.005 (2014).

33 Neri, F. et al. TET1 is controlled by pluripotency-associated factors in ESCs and downmodulated by PRC2 in differentiated cells and tissues. *Nucleic acids research*, doi:10.1093/nar/gkv392 (2015).

34 Ciccarone, F. et al. Poly(ADP-ribosyl)ation is involved in the epigenetic control of TET1 gene transcription. *Oncotarget* 5, 10356-10367, doi:10.18632/oncotarget. 1905 (2014).

35 Gambichler, T. et al. Decreased expression of ten-eleven translocation 2 protein is associated with progressive disease and death in patients with mucosis fungoides. *Br J Dermatol*, doi:10.1111/bjd.14174 (2015).

36 Park, J. L. et al. Decrease of 5hmC in gastric cancers is associated with TET1 silencing due to with DNA methylation and bivalent histone marks at TET1 CpG island 3'-shore. *Oncotarget* 6, 37647-37662, doi:10.18632/oncotarget.6069 (2015).

37 Tsai, K. W. et al. Reduction of global 5-hydroxymethylcytosine is a poor prognostic factor in breast cancer patients, especially for an ER/PR-negative subtype. *Breast Cancer Res Treat* 153, 219-234, doi:10.1007/s10549-015-3525-x (2015).

38 Rawluszko-Wieczorek, A. A. et al. Clinical significance of DNA methylation mRNA levels of TET family members in colorectal cancer. *Journal of cancer research and clinical oncology*, doi:10.1007/s00432-014-1901-2 (2015).

39 Ichimura, N. et al. Aberrant TET1 Methylation Closely Associated with CpG Island Methylator Phenotype in Colorectal Cancer. *Cancer Prev Res (Phila)* 8, 702-711, doi:10.1158/1940-6207.CAPR-14-0306 (2015).

40 Fan, M., He, X. & Xu, X. Restored expression levels of TET1 decrease the proliferation and migration of renal carcinoma cells. *Mol Med Rep*, doi:10.3892/mmr.2015.4058 (2015).

41 Cimmino, L. et al. TET1 is a tumor suppressor of hematopoietic malignancy. *Nat Immunol* 16, 653-662, doi:10.1038/ni.3148 (2015).

42 Neri, F. et al. Genome-wide analysis identifies a functional association of Tet1 and Polycomb repressive complex 2 in mouse embryonic stem cells. *Genome biology* 14, R91, doi:10.1186/gb-2013-14-8-r91 (2013).

43 Okashita, N. et al. PRDM14 promotes active DNA demethylation through the ten-eleven translocation (TET)-mediated base excision repair pathway in embryonic stem cells. *Development* 141, 269-280, doi:10.1242/dev.099622 (2014).

44 Williams, K. et al. TET1 and hydroxymethylcytosine in transcription and DNA methylation fidelity. *Nature* 473, 343-348, doi:10.1038/nature10066 (2011).

45 Yildirim, O. et al. Mbd3/NURD complex regulates expression of 5-hydroxymethylcytosine marked genes in embryonic stem cells. *Cell* 147, 1498-1510, doi:10.1016/j.cell.2011.11.054 (2011).

46 Li, H. P., Leu, Y. W. & Chang, Y. S. Epigenetic changes in virus-associated human cancers. *Cell Res* 15, 262-271, doi:10.1038/sj.cr.7290295 (2005).

47 Tsai, C. N., Tsai, C. L., Tse, K. P., Chang, H. Y. & Chang, Y. S. The Epstein-Barr virus oncogene product, latent membrane protein 1, induces the downregulation of E-cadherin gene expression via activation of DNA methyltransferases. *Proceedings of the National Academy of Sciences of the United States of America* 99, 10084-10089, doi:10.1073/pnas.152059399 (2002).

48 Ghoshal, K. et al. Inhibitors of histone deacetylase and DNA methyltransferase synergistically activate the methylated metallothionein I promoter by activating the transcription factor MTF-1 and forming an open chromatin structure. *Mol Cell Biol* 22, 8302-8319 (2002).

49 Baylin, S. B. & Ohm, J. E. Epigenetic gene silencing in cancer—a mechanism for early oncogenic pathway addiction? *Nat Rev Cancer* 6, 107-116, doi:10.1038/nrc1799 (2006).

50 Jin, H. et al. Epigenetic silencing of a Ca(2+)-regulated Ras GTPase-activating protein RASAL defines a new mechanism of Ras activation in human cancers. *Proceedings of the National Academy of Sciences of the United States of America* 104, 12353-12358, doi:10.1073/pnas.0700153104 (2007).

51 Li, L. et al. The human cadherin 11 is a pro-apoptotic tumor suppressor modulating cell stemness through Wnt/beta-catenin signaling and silenced in common carcinomas. *Oncogene* 31, 3901-3912, doi:10.1038/onc.2011.541 (2012).

52 Li, L. et al. Epigenetic identification of receptor tyrosine kinase-like orphan receptor 2 as a functional tumor suppressor inhibiting beta-catenin and AKT signaling but frequently methylated in common carcinomas. *Cellular and molecular life sciences: CMLS* 71, 2179-2192, doi:10.1007/s00018-013-1485-z (2014).

53 Ying, J. et al. Functional epigenetics identifies a protocadherin PCDH10 as a candidate tumor suppressor for nasopharyngeal, esophageal and multiple other carcinomas with frequent methylation. *Oncogene* 25, 1070-1080, doi: 10.1038/sj.onc.1209154 (2006).

54 Murray, P. G. et al. Epigenetic silencing of a proapoptotic cell adhesion molecule, the immunoglobulin superfamily member IGSF4, by promoter CpG methylation protects Hodgkin lymphoma cells from apoptosis. *The American journal of pathology* 177, 1480-1490, doi:10.2353/ajpath.2010.100052 (2010).

55 Wang, Z. et al. Epigenetic silencing of the 3p22 tumor suppressor DLEC1 by promoter CpG methylation in non-Hodgkin and Hodgkin lymphomas. *J Transl Med* 10, 209, doi:10.1186/1479-5876-10-209 (2012).

56 Tao, Q. et al. Methylation status of the Epstein-Barr virus major latent promoter C in iatrogenic B cell lymphoproliferative disease. Application of PCR-based analysis. *The American journal of pathology* 155, 619-625, doi:10.1016/S0002-9440(10)65157-7 (1999).

57 Tao, Q. et al. Defective de novo methylation of viral and cellular DNA sequences in ICF syndrome cells. *Human molecular genetics* 11, 2091-2102 (2002).

58 Tao, Q. Cancer research in an era when epigenetics is no longer "epi"—challenges and opportunities. *Chinese journal of cancer* 32, 1-2, doi:10.5732/cjc.012.10300 (2013).

---

What is claimed is:

1. A method for reducing risk of cancer in a subject, comprising the steps of:

(a) treating DNA from a biological sample taken from the subject with a bisulfite, wherein the sample is a nasopharyngeal, esophageal, lung, gastric, colon, rectum, liver, breast, cervical, renal, or blood sample;

(b) amplifying a genomic sequence of step (a) to determine the number of methylated CpGs in the genomic sequence, which is SEQ ID NO: 1 or SEQ ID NO: 2, or a fragment thereof comprising at least 5 CpGs;

(c) comparing the number of methylated CpGs determined in step (b) with the number of methylated CpGs in the same genomic sequence from a non-cancer biological sample of the same type and processed through steps (a) and (b);

(d) determining the subject, whose sample contains more methylated CpGs in the genomic sequence determined in step (b) compared to the number of methylated CpGs in the genomic sequence from the non-cancer sample and processed through steps (a) to (b), as having an increased risk for cancer compared with a healthy subject not diagnosed with cancer; and (d) administering to the subject having increased risk for cancer, a preventative treatment, chosen from the group consisting of modified lifestyle, regular screening, and regular examination.

2. The method of claim 1, wherein the biological sample is a tissue sample.

3. The method of claim 1, wherein the sample is a nasal or oral swab.

4. The method of claim 1, wherein the sample is an all blood cell sample, a white blood cell sample, or a platelet cell sample.

5. The method of claim 1, wherein the genomic sequence is a fragment of SEQ ID NO:1 comprising at least 10, 15, 20, 25, 30, or 35 CpGs.

6. The method of claim 1, wherein the genomic sequence is SEQ ID NO:1 or 2.

7. The method of claim 1, wherein step (b) comprises a polymerase chain reaction (PCR).

8. The method of claim 1, wherein step (b) comprises a polynucleotide sequencing reaction.

9. The method of claim 1, wherein step (b) comprises a polynucleotide hybridization assay.

* * * * *